(12) United States Patent
Bhagavatheeswaran et al.

(10) Patent No.: US 11,919,957 B2
(45) Date of Patent: Mar. 5, 2024

(54) METHODS OF TREATING TUMOR

(71) Applicant: Bristol-Myers Squibb Company, Princeton, NJ (US)

(72) Inventors: Prabhu Seshaiyer Bhagavatheeswaran, Hamden, CT (US); Nicholas Allan John Botwood, Princeton, NJ (US); Han Chang, West Windsor, NJ (US); William J. Geese, Pipersville, PA (US); Sabine Maier, Lawrenceville, NJ (US); Giovanni Selvaggi, Brooklyn, NY (US); Joseph Daniel Szustakowski, Pennington, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 18/047,216

(22) Filed: Oct. 17, 2022

(65) Prior Publication Data
US 2023/0295302 A1   Sep. 21, 2023

Related U.S. Application Data

(63) Continuation of application No. 16/756,157, filed as application No. PCT/US2018/055894 on Oct. 15, 2018, now abandoned.

(60) Provisional application No. 62/650,654, filed on Mar. 30, 2018, provisional application No. 62/572,514, filed on Oct. 15, 2017.

(51) Int. Cl.
*C12Q 1/6886* (2018.01)
*C07K 16/28* (2006.01)
*A61K 39/00* (2006.01)

(52) U.S. Cl.
CPC ........ *C07K 16/2818* (2013.01); *C12Q 1/6886* (2013.01); *A61K 2039/545* (2013.01); *C07K 2317/76* (2013.01); *C12Q 2600/106* (2013.01); *C12Q 2600/156* (2013.01)

(58) Field of Classification Search
CPC .................................................. C07K 16/2818
USPC ...................................................... 424/130.1
See application file for complete search history.

(56) References Cited

U.S. PATENT DOCUMENTS

| | | | |
|---|---|---|---|
| 5,821,337 A | 10/1998 | Carter et al. | |
| 5,977,318 A | 11/1999 | Linsley et al. | |
| 6,051,227 A | 4/2000 | Allison et al. | |
| 6,210,669 B1 | 4/2001 | Aruffo et al. | |
| 6,303,121 B1 | 10/2001 | Kwon | |
| 6,355,476 B1 | 3/2002 | Kwon et al. | |
| 6,362,325 B1 | 3/2002 | Kwon | |
| 6,569,997 B1 | 5/2003 | Kwon | |
| 6,682,736 B1 | 1/2004 | Hanson et al. | |
| 6,808,710 B1 | 10/2004 | Wood et al. | |
| 6,887,673 B2 | 5/2005 | Kunkel et al. | |
| 6,905,685 B2 | 6/2005 | Kwon | |
| 6,974,863 B2 | 12/2005 | Kwon | |
| 6,984,720 B1 | 1/2006 | Korman et al. | |
| 7,034,121 B2 | 4/2006 | Carreno et al. | |
| 7,214,493 B2 | 5/2007 | Kunkel et al. | |
| 7,288,638 B2 | 10/2007 | Jure-Kunkel et al. | |
| 7,488,802 B2 | 2/2009 | Collins et al. | |
| 7,595,048 B2 | 9/2009 | Honjo et al. | |
| 7,767,429 B2 | 8/2010 | Bookbinder et al. | |
| 7,812,135 B2 | 10/2010 | Smith et al. | |
| 7,943,743 B2 | 5/2011 | Korman et al. | |
| 8,008,449 B2 | 8/2011 | Korman et al. | |
| 8,168,179 B2 | 5/2012 | Honjo et al. | |
| 8,168,757 B2 | 5/2012 | Finnefrock et al. | |
| 8,217,149 B2 | 7/2012 | Irving et al. | |
| 8,354,509 B2 | 1/2013 | Carven et al. | |
| 8,388,967 B2 | 3/2013 | Smith et al. | |
| 8,399,623 B2 | 3/2013 | Terrett et al. | |

(Continued)

FOREIGN PATENT DOCUMENTS

JP           2008278814 A      11/2008
WO       WO-0037504 A2      6/2000

(Continued)

OTHER PUBLICATIONS

Aguiar, P. N., et al., "Immune Checkpoint Inhibitors for Advanced Non-small Cell Lung Cancer: Emerging Sequencing for New Treatment Targets," ESMO Open 2(3):e000200, BMJ, United Kingdom (Jul. 2017).

(Continued)

*Primary Examiner* — Sean E Aeder
(74) *Attorney, Agent, or Firm* — Sterne, Kessler, Goldstein & Fox P.L.L.C.

(57) ABSTRACT

The disclosure provides a method for treating a subject afflicted with a tumor derived from a small cell lung cancer (SCLC) having a high tumor mutational burden (TMB) status comprising administering to the subject a monotherapy comprising an anti-PD-1 antibody or a combination therapy comprising an anti-PD-1 antibody and an anti-CTLA-4 antibody. The present disclosure also provides a method for identifying a subject suitable for treatment with an anti-PD-1 antibody or a combination therapy comprising an anti-PD-1 antibody and an anti-CTLA-4 antibody comprising measuring a TMB status of a biological sample of the subject. A high TMB status identifies the patient as suitable for treatment with an anti-PD-1 antibody or antigen-binding portion thereof. The TMB status can be determined by sequencing nucleic acids in the tumor and identifying a genomic alteration, e.g., a somatic nonsynonymous mutation, in the sequenced nucleic acids.

13 Claims, 10 Drawing Sheets

Specification includes a Sequence Listing.

(56) References Cited

U.S. PATENT DOCUMENTS

| | | | |
|---|---|---|---|
| 8,709,424 B2 | 4/2014 | Schebye et al. |
| 8,728,474 B2 | 5/2014 | Honjo et al. |
| 8,779,105 B2 | 7/2014 | Korman et al. |
| 8,900,587 B2 | 12/2014 | Carven et al. |
| 9,067,999 B1 | 6/2015 | Honjo et al. |
| 9,073,994 B2 | 7/2015 | Honjo et al. |
| 9,084,776 B2 | 7/2015 | Korman et al. |
| 9,169,325 B2 | 10/2015 | Keler et al. |
| 9,212,224 B2 | 12/2015 | Cogswell et al. |
| 9,358,289 B2 | 6/2016 | Korman et al. |
| 9,387,247 B2 | 7/2016 | Korman et al. |
| 9,393,301 B2 | 7/2016 | Honjo et al. |
| 9,402,899 B2 | 8/2016 | Honjo et al. |
| 9,439,962 B2 | 9/2016 | Honjo et al. |
| 9,492,539 B2 | 11/2016 | Korman et al. |
| 9,492,540 B2 | 11/2016 | Korman et al. |
| 9,580,507 B2 | 2/2017 | Korman et al. |
| 9,856,320 B2 | 1/2018 | Cogswell et al. |
| 10,072,082 B2 | 9/2018 | Cogswell et al. |
| 10,138,299 B2 | 11/2018 | Cogswell et al. |
| 10,266,594 B1 | 4/2019 | Cogswell et al. |
| 10,266,595 B2 | 4/2019 | Cogswell et al. |
| 10,266,596 B1 | 4/2019 | Cogswell et al. |
| 10,308,714 B2 | 6/2019 | Cogswell et al. |
| 10,316,090 B2 | 6/2019 | Cogswell et al. |
| 10,316,091 B2 | 6/2019 | Cogswell et al. |
| 10,323,092 B2 | 6/2019 | Cogswell et al. |
| 10,323,093 B2 | 6/2019 | Cogswell et al. |
| 10,441,655 B2 | 10/2019 | Korman et al. |
| 10,577,423 B2 | 3/2020 | Cogswell et al. |
| 10,584,170 B2 | 3/2020 | Cogswell et al. |
| 10,604,575 B2 | 3/2020 | Cogswell et al. |
| 2005/0095244 A1 | 5/2005 | Jure-Kunkel et al. |
| 2009/0136494 A1 | 5/2009 | Ponath et al. |
| 2011/0150892 A1 | 6/2011 | Thudium et al. |
| 2013/0183321 A1 | 7/2013 | Smith et al. |
| 2014/0004112 A1 | 1/2014 | Wucherpfennig et al. |
| 2014/0065152 A1 | 3/2014 | Kwon |
| 2014/0072565 A1 | 3/2014 | Kwon |
| 2014/0072566 A1 | 3/2014 | Kwon |
| 2014/0093511 A1 | 4/2014 | Lonberg et al. |
| 2014/0220002 A1 | 8/2014 | Ponte et al. |
| 2014/0322208 A1 | 10/2014 | Kuhne et al. |
| 2014/0348841 A1 | 11/2014 | Schebye et al. |
| 2015/0079109 A1 | 3/2015 | Li et al. |
| 2016/0046716 A1 | 2/2016 | Wucherpfennig et al. |
| 2016/0272708 A1 | 9/2016 | Chen |
| 2017/0022275 A1 | 1/2017 | Wucherpfennig et al. |
| 2020/0138945 A1 | 5/2020 | Korman et al. |
| 2020/0239577 A1 | 7/2020 | Bhagavatheeswaran et al. |
| 2020/0308282 A1 | 10/2020 | Cogswell et al. |
| 2021/0032344 A1 | 2/2021 | Bhagavatheeswaran et al. |
| 2021/0101980 A1 | 4/2021 | Bhagavatheeswaran et al. |

FOREIGN PATENT DOCUMENTS

| | | |
|---|---|---|
| WO | WO-0100244 A2 | 1/2001 |
| WO | WO-2005003168 A2 | 1/2005 |
| WO | WO-2005009465 A1 | 2/2005 |
| WO | WO-2006003179 A1 | 1/2006 |
| WO | WO-2006072625 A2 | 7/2006 |
| WO | WO-2006072626 A1 | 7/2006 |
| WO | WO-2006105021 A2 | 10/2006 |
| WO | WO-2007042573 A2 | 4/2007 |
| WO | WO-2007113648 A2 | 10/2007 |
| WO | WO-2008084106 A1 | 7/2008 |
| WO | WO-2008156712 A1 | 12/2008 |
| WO | WO-2009009116 A2 | 1/2009 |
| WO | WO-2009073533 A2 | 6/2009 |
| WO | WO-2010065939 A1 | 6/2010 |
| WO | WO-2011028683 A1 | 3/2011 |
| WO | WO-2011066389 A1 | 6/2011 |
| WO | WO-2012071411 A2 | 5/2012 |
| WO | WO-2012122444 A1 | 9/2012 |
| WO | WO-2012145493 A1 | 10/2012 |
| WO | WO-2012160448 A2 | 11/2012 |
| WO | WO-2013039954 A1 | 3/2013 |
| WO | WO-2013079174 A1 | 6/2013 |
| WO | WO-2013173223 A1 | 11/2013 |
| WO | WO-2013181634 A2 | 12/2013 |
| WO | WO-2014055648 A1 | 4/2014 |
| WO | WO-2014151006 A2 | 9/2014 |
| WO | WO-2014179664 A1 | 11/2014 |
| WO | WO-2014194302 A2 | 12/2014 |
| WO | WO-2014206107 A1 | 12/2014 |
| WO | WO-2015026684 A1 | 2/2015 |
| WO | WO-2015031667 A2 | 3/2015 |
| WO | WO-2015035606 A1 | 3/2015 |
| WO | WO-2015042246 A1 | 3/2015 |
| WO | WO-2015085847 A1 | 6/2015 |
| WO | WO-2015103037 A2 | 7/2015 |
| WO | WO-2015112800 A1 | 7/2015 |
| WO | WO-2015112900 A1 | 7/2015 |
| WO | WO-2015184099 A1 | 12/2015 |
| WO | WO-2015187835 A2 | 12/2015 |
| WO | WO-2016077553 A1 | 5/2016 |
| WO | WO-2016081947 A2 | 5/2016 |
| WO | WO-2016106159 A1 | 6/2016 |
| WO | WO-2016149201 A2 | 9/2016 |
| WO | WO-2016176504 A1 | 11/2016 |
| WO | WO-2016196237 A1 | 12/2016 |
| WO | WO-2016197367 A1 | 12/2016 |
| WO | WO-2017019846 A1 | 2/2017 |
| WO | WO-2017020291 A1 | 2/2017 |
| WO | WO-2017020858 A1 | 2/2017 |
| WO | WO-2017024465 A1 | 2/2017 |
| WO | WO-2017024515 A1 | 2/2017 |
| WO | WO-2017025016 A1 | 2/2017 |
| WO | WO-2017025051 A1 | 2/2017 |
| WO | WO-2017034916 A1 | 3/2017 |
| WO | WO-2017040790 A1 | 3/2017 |
| WO | WO-2017087870 A1 | 5/2017 |
| WO | WO-2017106061 A1 | 6/2017 |
| WO | WO-2017123557 A1 | 7/2017 |
| WO | WO-2017132825 A1 | 8/2017 |
| WO | WO-2017132827 A1 | 8/2017 |
| WO | WO-2017133540 A1 | 8/2017 |
| WO | WO-2017151502 A1 | 9/2017 |
| WO | WO-2017151517 A1 | 9/2017 |
| WO | WO-2018013818 A2 | 1/2018 |
| WO | WO-2018068028 A1 | 4/2018 |
| WO | WO-2018183928 A1 | 10/2018 |
| WO | WO-2019075468 A1 | 4/2019 |
| WO | WO-2019191676 A1 | 10/2019 |

OTHER PUBLICATIONS

Alexandrov, L. B., et al., "Signatures of Mutational Processes in Human Cancer," Nature 500(7463):415-421, Nature Publishing Group, United Kingdom (Aug. 2013).

Anagnostou, V., et al., "Evolution of Neoantigen Landscape during Immune Checkpoint Blockade in Non-Small Cell Lung Cancer," Cancer Discovery 7(3):264-276, American Association for Cancer Research, United States (Mar. 2017).

Anonymous: "Archive History for NCT03091491: Randomised Phase 2 Study of Nivolumab Versus Nivolumab and Ipilimumab Combination in EGFR Mutant Non-small Cell Lung Cancer", Jul. 6, 2017 (Jul. 6, 2017), XP055598941, URL:https://clinicaltrials.gov/ct2/history/NCT03091491?V2=View#StudyPageTop.

Anonymous: Archive History for Study:NCT02477826 An Investigational Immuno-Therapy Trial of Nivolumab, or Nivolumab Plus Ipilimumab, or Nivolumab Plus Platinum-Doublet Chemotherapy, Compared to Platinum Doublet Chemotherapy in Patients With Stage IV Non-Small Cell Lung Cancer (NSCLC) (CheckMate 227), Feb. 12, 2018 (Feb. 12, 2018). XP055599605.

Anonymous: Archive History for Study:NCT02659059 Nivolumab in Combination With Ipilimumab (Part 1); Nivolumab Plus Ipilimumab in Combination With Chemotherapy (Part 2) as First Line Therapy in Stage IV Non-Small Cell Lung Cancer (CheckMate 568), Jan. 11, 2018 (Jan. 11, 2018). XP055599602.

(56) References Cited

OTHER PUBLICATIONS

Anonymous: "History of Changes for NCT02869789: An Investigational Immuno-therapy Study for Safety of Nivolumab in Combination With Ipilimumab to Treat Advanced Cancers (CheckMate 817)", Mar. 6, 2018 (Mar. 6, 2018), XP055600096, URL:https://clinicaltrials.gov/ct2/history/NCT02869789?V27=View#StudyPageTop.
Antonia, S., et al., "Safety and Antitumour Activity of Durvalumab Plus Tremelimumab in Non-Small Cell Lung Cancer: A Multicentre, Phase 1b Study, " The Lancet Oncology 17(3):299-308, Lancet Pub. Group, United Kingdom (Mar. 2016).
Antonia, S., et al. "Impact of Tumor Mutation Burden on the Efficacy of Nivolumab or Nivolumab+ Ipilimumab in Small Cell Lung Cancer: An Exploratory Analysis of CheckMate 032," World Conference on Lung Cancer, retrieved from the Internet: URL:https://library.iaslc.org/search-speaker?search_speaker=49424 on Jan. 9, 2019 (Oct. 2017).
Antonia, S. J., et al., "Nivolumab Alone and Nivolumab Plus Ipilimumab in Recurrent Small-Cell Lung Cancer (CheckMate 032): a Multicentre, Open-Label, Phase 1/2 Trial," The Lancet Oncology 17(7):883-895, Lancet Publishing Group, London. (Jul. 2016).
Asai, N., et al., "Relapsed Small Cell Lung Cancer: Treatment Options and Latest Developments," Therapeutic Advances in Medical Oncology 6(2):69-82, Sage, London. (Mar. 2014).
Atlas of Genetics and Cytogenetics in Oncology and Haematology, "Colon: Colorectal Adenocarcinoma," AtlasGeneticsOncology.org, accessed at http://atlasgeneticsoncology.org//Tumors/colonID5006.html on Nov. 21, 2017, 20 pages.
Balar, A. V., et al., "Atezolizumab as First-Line Treatment in Cisplatin-Ineligible Patients with Locally Advanced and Metastatic Urothelial Carcinoma: a Single-Arm, Multicentre, Phase 2 Trial," Lancet 389:(10064):67-76, Elsevier, London. (Jan. 2017).
Barlesi, F., et al., "Long-term Outcomes With Nivolumab (Nivo) Vs Docetaxel (Doc) in Patients (Pts) With Advanced (Adv) Nsclc: Checkmate 017 and Checkmate 057 2-y Update," Annals of Oncology 27(6):1215PD, (Oct. 2016).
Blank, C. U., et al., "Cancer Immunology. The "Cancer Immunogram"," Science 352(6286):658-660, American Association for the Advancement of Science, Washington. (May 2016).
Borghaei, H., et al., "Nivolumab Versus Docetaxel in Advanced Nonsquamous Non-small-cell Lung Cancer," The New England Journal of Medicine 373(17):1627-1639, Massachusetts Medical Society, United States (Oct. 2015).
Boutros, C., et al., "Safety Profiles of Anti-CTLA-4 and Anti-PD-1 Antibodies Alone and in Combination," Nature Reviews Clinical Oncology 13(8):473-486, Nature Publishing Group, United Kingdom (May 2016).
Brahmer, J., et al., "Nivolumab versus Docetaxel in Advanced Squamous-Cell Non-Small-Cell Lung Cancer," The New England Journal of Medicine 373(2):123-135, Massachusetts Medical Society, United States (Jul. 2015).
Brahmer, J.R., et al., "Safety and Activity of Anti-PD-L1 Antibody in Patients with Advanced Cancer," The New England Journal of Medicine 366(26):2455-2465, Massachusetts Medical Society, United States (Jun. 2012).
Brahmer., J.R., et al., "Phase I Study of Single-agent Anti-programmed Death-1 (MDX-1106) in Refractory Solid Tumors: Safety, Clinical Activity, Pharmacodynamics, and Immunologic Correlates," Journal of Clinical Oncology 28(19):3167-3175, American Society of Clinical Oncology, United States (Jul. 2010).
Bristol Myers Squibb Company, OPDIVO (Nivolumab) Prescribing Information, accessed at https://packageinserts.bms.com/pi/pi_opdivo.pdf on Mar. 2, 2021, 45 pages.
Byers, L.A and Rudin, C.M., "Small Cell Lung Cancer: Where Do We Go From Here?," Cancer, 121(5):664-672, Wiley, United States (Mar. 2015).
Campbell, B. B., et al., "Comprehensive Analysis of Hypermutation in Human Cancer," Cell 171(5):1042-1056.e10, Cell Press, United Sates (Nov. 2017).

Campesato, L. F., et al., "Comprehensive Cancer-Gene Panels can be Used to Estimate Mutational Load and Predict Clinical Benefit to PD-1 Blockade in Clinical Practice," Oncotarget 6(33):34221-34227, Impact Journals LLC, United States (2015).
Carbone, D.P., et al., "First-Line Nivolumab in Stage IV or Recurrent Non-Small-Cell Lung Cancer," The New England Journal of Medicine 376(25):2415-2426, Massachusetts Medical Society, United States (Jun. 2017).
Chalmers., et al., "Analysis of 100,000 Human Cancer Genomes Reveals the Landscape of Tumor Mutational Burden," Genome medicine 9(1):34, BioMed Central, United Kingdom (Apr. 2017).
Champiat, S., et al., "Exomics and Immunogenics: Bridging Mutational Load and Immune Checkpoints Efficacy," Oncoimmunology 3(1):e27817, Landes Bioscience, United States (2014).
Cheng, D. T., et al., "Comprehensive Detection of Germline Variants by MSK-IMPACT, a Clinical Diagnostic Platform for Solid Tumor Molecular Oncology and Concurrent Cancer Predisposition Testing," BMC Medical Genomics 10(1):33, BioMed Central Ltd., United Kingdom (May 2017).
Clinical Trials NCT02628067, "Study of Pembrolizumab (MK-3475) in Participants With Advanced Solid Tumors (MK-3475-158/KEYNOTE-158)," ClinicalTrials.gov, Merck Sharp & Dohme Corp., accessed at https://clinicaltrials.gov/ct2/show/NCT02628067, accessed on Jul. 9, 2020, 8 pages.
Columbus, G., "BMS Withdraws Nivolumab/Ipilimumab Application in TMB-HighNSCLC News/Bms-Withdraws-Nivolumabipilimumab-Application-in-Tmbhigh-Nsclc", Targeted Oncology, Jan. 25, 2019, XP055599089, URL:https://www.targetedonc.com/news/bms-withdraws-nivolumabipilimumab-application-intmbhigh-nsclc.
Condeelis, J. and Weissleder, R., "In Vivo Imaging in Cancer," Cold Spring Harbor Perspectives in Biology 2(12):a003848, Cold Spring Harbor Laboratory Press, United States (Dec. 2010).
Creelan, B.C., "Update on Immune Checkpoint Inhibitors in Lung Cancer," Cancer Control: Journal of the Moffitt Cancer Center 21(1):80-89, H. Lee Moffitt Cancer Center and Research Institute, United States (Jan. 2014).
Curran, M.A., et al., "PD-1 and CTLA-4 Combination Blockade Expands Infiltrating T Cells and Reduces Regulatory T and Myeloid Cells within B16 Melanoma Tumors," Proceedings of the National Academy of Sciences, USA 107(9):4275-4280, National Academy of Sciences, United States (2010).
Daniels, M., et al., "Whole Genome Sequencing for Lung Cancer," Journal of Thoracic Disease 4(2):155-163, AME Publishing Company, Hong Kong (2012).
Davis, A.A., et al., "Abstract 658: Association of tumor mutational burden (TMB) with DNA repair mutations and response to anti-PD-1/PD-L1 therapy in non-small cell lung cancer (NSCLC)," in: Proceedings of the American Association for Cancer Research Annual Meeting, Apr. 2017.
DEN170058: Evaluation of Automatic Class III Designation for MSK-IMPACT (Integrated Mutation Profiling of Actionable Cancer Targets): Decision Summary, United States Food and Drug Administration, accessed at https://www.accessdata.fda.gov/cdrh_docs/reviews/DEN170058.pdf, Nov. 2017, 57 pages.
Desai, A., et al., "Phase II Trial of Pembrolizumab (P) in Patients (pts) With Previously-treated Mesothelioma (MM)," Journal of Clinical Oncology 36(15_suppl):8565-8565, American Society of Clinical Oncology, United States of America (May 2018).
Drake, "Safety, Durable Clinical Benefit, and Remission Resulting from Nivolumanb (Anti-PD-1; BMS-936558; ONO-4538) in a Phase 1 Trial In Patients With Previously Treated Metastatic Renal Cell Carcinoma (mRCC); Long-Term Patient Follow-Up, Abstracts of the 12th International Kidney Cancer Symposium. Oct. 25-26, 2013. Chicago, Illinois, USA," Bju International 112 (Suppl 3):1-17, Blackwell Science, United Kingdom (Nov. 2013).
Drake, C.G., et al., "Survival, safety, and response duration results of nivolumab (Anti-PD-1; BMS-936558; ONO-4538) in a phase I trial in patients with previously treated metastatic renal cell carcinoma (mRCC): Long-term patient follow-up," Journal of Clinical Oncology 31(15_Suppl):4514, American Society of Clinical Oncology, United States (2013).

(56) References Cited

OTHER PUBLICATIONS

Eisenhauer, E.A., et al., "New Response Evaluation Criteria in Solid Tumours: Revised RECIST Guideline (Version 1.1)," European Journal of Cancer 45(2):228-247, (Jan. 2009).

Ettinger, D.S., et al., "NCCN Guidelines Insights: Non-Small Cell Lung Cancer, Version 4.2016.," Journal of the National Comprehensive Cancer Network 14(3):255-264, Harborside Press, United States (Mar. 2016).

Ettinger, D.S., et al., "Non-Small Cell Lung Cancer, Version 5.2017, NCCN Clinical Practice Guidelines in Oncology," Journal of the National Comprehensive Cancer Network : JNCCN 15(4):504-535, Jones and Bartlett Publishers, United States (Apr. 2017).

Fabrizio, D., et al., "Analytic Validation of a Next Generation Sequencing Assay to Identify Tumor Mutational Burden From Blood (bTMB) to Support Investigation of an Anti-PD-L1 Agent, Atezolizumab, in a First Line Non-Small Cell Lung Cancer Trial (BFAST)," Annals of Oncology 28(5):v27, Elsevier Ltd., on behalf of the European Society for Medical Oncology, United Kingdom (Sep. 2017).

Fisher, S., et al., "A Scalable, Fully Automated Process for Construction of Sequence-Ready Human Exome Targeted Capture Libraries," Genome Biology 12(1):R1, BioMed Central Ltd, United Kingdom (2011).

Flies, D.B., et al., "Blockade of the B7-H1/PD-1 Pathway for Cancer Immunotherapy," The Yale Journal of Biology and Medicine 84(4):409-421, Yale Journal of Biology and Medicine, United States (Dec. 2011).

Foundation Medicine, "Foundation Medicine Announces Commercial Availability of FoundationOne CDx™, the First FDA-Approved Comprehensive Genomic Profiling Assay for All Solid Tumors Incorporating Multiple Companion Diagnostics," Business Wire.com, published on Mar. 30, 2018, accessed at https://www.businesswire.com/news/home/20180330005010/en/Foundation-Medicine-Announces-Commercial-Availability-of-FoundationOne-CDx%E2%84%A2 on May 24, 2018, 2 pages.

Foundation Medicine, "Foundation Medicine Announces Commercial Availability of FoundationOne CDx[TM], the First FDA-Approved Comprehensive Genomic Profiling Assay for All Solid Tumors Incorporating Multiple Companion Diagnostics," accessed at https://www.foundationmedicine.com/press-releases/d4f3c3da-46a8-49cd-a0de-cdfb678204dc, accessed on Jul. 9, 2020.

Foundation Medicine, "FoundationOne® CDx: Technical Information," FoundationMedicine.com, accessed at https://www.accessdata.fda.gov/cdrh_docs/pdf17/P170019S006C.pdf on Nov. 3, 2020, 45 pages.

Foundation Medicine, "FoundationOne® HEME: Technical Specifications," FoundationMedicine.com, published Nov. 2017, accessed at https://assets.ctfassets.net/vhribv121mne/zBxaQC12cScqgsEk8seMO/abf6133874fle5929403f66d90c3b900/F1H_TechnicalInformation_06_digital.pdf on Nov. 3, 2020, 3 pages.

Foundation Medicine, "FoundationOne® Technical Information and Test Overview," FoundationMedicine.com, published on Aug. 18, 2014 accessed at https://assets.ctfassets.net/vhribv121mne/6YRrchSINOeSu48YwuesoY/caeec492925a7d569ce4e070866f709b/F1_-_Tech_Specs.pdf on Nov. 3, 2020, 2 pages.

Foundation Medicine Inc., "FDA Approves Foundation Medicine's FoundationOne CDx™, the First and Only Comprehensive Genomic Profiling Test for All Solid Tumors Incorporating Multiple Companion Diagnostics," FoundationMedicine.com, accessed at https://www.foundationmedicine.com/press-releases/f2b20698-10bd-4ac9-a5e5-c80c398a57b5 on Dec. 5, 2017, 4 pages (Nov. 2017).

Foundation Medicine Inc., "FoundationOne®CDx," FoundationMedicine.com, accessed at URL:[https://www.foundationmedicine.com/test/foundationone-cdx] on Jun. 16, 2021, 5 pages.

Frampton, G. M., et al., "Assessment and Comparison of Tumor Mutational Burden and Microsatellite Instability Status in 40,000 Cancer Genomes," Annals of Oncology 27(6):vi15-vi42, Oxford University Press on behalf of the European Society for Medical Oncology, United Kingdom (2016).

Frampton, G. M., et al., "Assessment of Tumor Mutation Burden from >60,000 Clinical Cancer Patients Using Comprehensive Genomic Profiling," Journal of Clinical Oncology 34(15):11558-11558, American Society of Clinical Oncology, United States (2016).

Frampton, G.M., et al., "Development and Validation of a Clinical Cancer Genomic Profiling Test Based on Massively Parallel DNA Sequencing," Nature biotechnology 31(11):1023-31, Nature America Publishing, United States (Nov. 2013).

Galsky, M. D., et al., "Impact of Zumor Mutation Burden on Nivolumab Efficacy in Second-Line Urothelial Carcinoma Patients: Exploratory Analysis of the Phase II Checkmate 275 Study," Abstracts Genitourinary Tumours, Non-Prostate 28(5):V296-V297, Oxford University Press on Behalf of the European Society for Medical Oncology, United Kingdom (Sep. 2017).

Gandara, D. R., et al., "Blood-Based Biomarkers for Cancer Immunotherapy: Tumor Mutational Burden in Blood (bTMB) is Associated With Improved Atezolizumab (ATEZO) Efficacy in 2L+ NSCLC (POPLAR and OAK)," Annals of Oncology 28(5): v460-v496, Elsevier Ltd., on behalf of the European Society for Medical Oncology, United Kingdom (Sep. 1, 2017).

GenBank, "cytotoxic T-lymphocyte-associated protein 4 [*Homo sapiens*]," Accession No. AAB59385.1, accessed on https://www.ncbi.nlm.nih.gov/protein/AAB59385, Nov. 1, 1994.

GenBank, "Human hPD-1 (hPD-1) mRNA, complete cds," Accession No. U64863.1, accessed on https://www.ncbi.nlm.nih.gov/nuccore/U64863, Oct. 12, 2005.

GenBank, "Programmed Cell Death 1 Ligand 1," Accession No. Q9NZQ7, accessed at https://www.ncbi.nlm.nih.gov/protein/Q9NZQ7, accessed on Nov. 3, 2020, 5 pages.

Gettinger, S., et al., "First-line nivolumab (antiPD-1; BMS-936558, ON0-4538) monotherapy in advanced NSCLC: safety, efficacy, and correlation of outcomes with PD-L1 status," Presented at: American Society of Clinical Oncology Annual Meeting; Jun. 3-7, 2014; Chicago, IL, USA; 2014. poster 38.

Gettinger, S., et al., "Nivolumab Monotherapy for First-Line Treatment of Advanced Non-Small-Cell Lung Cancer," Journal of Clinical Oncology 34(25):2980-2987, American Society of Clinical Oncology, United States (Sep. 2016).

Goldberg, M. E., et al., "Abstract 1775: The Interaction of PD-L1, TMB, and Genomic Alterations in NSCLC," Proceedings: AACR Annual Meeting 2017 77(Supp-13):1775, American Association for Cancer Research, United States (Jul. 2017).

Goodman, A.M., et al., "Tumor Mutational Burden as an Independent Predictor of Response to Immunotherapy in Diverse Cancers," Molecular Cancer Therapeutics 16(11):2598-2608, American Association for Cancer Research, United States (Nov. 2017).

Gorelik, L., et al., "Abstract 4606: Preclinical Characterization of a Novel Fully Human IgG1 Anti-PD-L1 mAb CK-301," Proceedings of 2017 AACR Annual Meeting 77(13):4606, American Association for Cancer Research, United States (Jul. 2017).

Govindan, R., et al., "Genomic Landscape of Non-Small Cell Lung Cancer in Smokers and Never-Smokers," Cell 150(6):1121-1134, Cell Press, United States (2012).

(56) References Cited

OTHER PUBLICATIONS

Grisham, J., "Fda Authorizes MSK-IMPACT Test for Analyzing Patient Tumors," Memorial Sloan Kettering Cancer Center, accessed at https://www.mskcc.org/blog/fda-authorizes-msk-impact-test-analyzing-patient-tumors on Nov. 20, 2017, 7 pages (Nov. 2017).

Guardant Health, "The Guardant360® Assay Specifications," GuardantHealth.com, accessed from https://www.therapyselect.de/sites/default/files/downloads/guardant360/guardant360_specification-sheet_en.pdf on Nov. 3, 2020, 2 pages.

Hamid, O. and Carvajal, R.D., "Anti-programmed Death-1 and Anti-programmed Death-ligand 1 Antibodies in Cancer Therapy," Expert Opinion on Biological Therapy 13(6):847-861, Taylor & Francis, United Kingdom (Jun. 2013).

Hamid, O., et al., "Safety and Tumor Responses with Lambrolizumab (Anti-Pd-1) in Melanoma," The New England Journal of Medicine 369(2):134-144, Massachusetts Medical Society, United States of America (Jul. 2013).

Hanna, N., et al., "Randomized Phase III Trial of Pemetrexed Versus Docetaxel in Patients with Non-small-cell Lung Cancer Previously Treated with Chemotherapy," Journal of Clinical Oncology 22(9):1589-1597, American Society of Clinical Oncology, United States(May 2004).

Hanna, N., et al., "Systemic Therapy for Stage IV Non-small-cell Lung Cancer: American Society of Clinical Oncology Clinical Practice Guideline Update Summary," Journal of oncology practice 13(12):832-837, American Society of Clinical Oncology, United States (Dec. 2017).

Hellmann, M. D., et al., "Nivolumab +/- Ipilimumab in Advanced Small-Cell Lung Cancer (SCLC): First Report of a Randomized Expansion Cohort From CheckMate 032," Journal of Clinical Oncology 35(15):8503-8503, American Society of Clinical Oncology Journal, United States (May 2017).

Hellmann, M.D., et al., "Genomic Features of Response to Combination Immunotherapy in Patients with Advanced Non-Small-Cell Lung Cancer", Cancer Cell 33(5):843-852.e4, Cell Press, United States (Apr. 2018) XP055510129.

Hellmann, M.D., et al., "Nivolumab Plus Ipilimumab as First-line Treatment for Advanced Non-small-cell Lung Cancer (Checkmate 012): Results of an Open-label, Phase 1, Multicohort Study," The Lancet Oncology 18(1):31-41, The Lancet Publishing Group, United Kingdom (Jan. 2017).

Hellmann M.D., et al., "Nivolumab plus Ipilimumab in Lung Cancer with a High Tumor Mutational Burden", New England Journal of Medicine 378(22):2093-2104, Massachusetts Medical Society, United States (May 2018) XP55600294.

Herbst, R. S., et al., "A Study of MPDL3280A, an Engineered PD-L1 Antibody in Patients with Locally Advanced or Metastatic Tumors," Journal of Clinical Oncology, 31(Suppl): Abstract 3000, American Society of Clinical Oncology, United States (2013).

International Search Report and Written Opinion for International Application No. PCT/US2018/025518, European Patent Office, Netherlands, dated Jun. 8, 2018, 18 pages.

International Search Report and Written Opinion for International Application No. PCT/US2018/055894, European Patent Office, Netherlands, dated Jan. 24, 2019, 16 pages.

International Search Report and Written Opinion for International Application No. PCT/US2019/024987, European Patent Office, Netherlands, dated Jul. 8, 2019, 16 pages.

Jamal-Hanjani, M., et al., "Tracking Genomic Cancer Evolution for Precision Medicine: The Lung TRACERx Study," PLoS Biology 12(7):e1001906, Public Library of Science, San Fransisco (Jul. 2014).

Jamal-Hanjani, M., et al., "Tracking the Evolution of Non-Small-Cell Lung Cancer," The New England Journal of Medicine 376(22):2109-2121, Massachusetts Medical Society, Boston (Jun. 2017).

Jamal-Hanjani, M., et al., "Translational Implications of Tumor Heterogeneity," Clinical Cancer Research 21(6):1258-1266, The Association, United States (Mar. 2015).

Johnson, D.B., et al., "Severe Cutaneous and Neurologic Toxicity in Melanoma Patients during Vemurafenib Administration Following Anti-PD-1 Therapy," Cancer Immunology Research 1(6):373-377, American Association for Cancer Research, United States (Dec. 2013).

Kaplon, H. and Reichert, J.M., "Antibodies to Watch in 2018," mAbs 10(2):183-203, Taylor & Francis, United States (Feb./Mar. 2018).

Kim, J. M., et al., "Immune Escape to PD-L1/PD-1 Blockade: Seven Steps to Success (or Failure)," Annals of Oncology 27(8):1492-1504, Elsevier, London. (Aug. 2016).

Kowanetz, M., et al., "OA20.01 Tumor Mutation Burden (TMB) is Associated with Improved Efficacy of Atezolizumab in 1L and 2L+ NSCLC Patients," Oral Abstract Session 12(1):S321-S322, Journal of Thoracic Oncology (Jan. 2017).

Kowanetz, M., et al., "Tumor Mutation Burden (TMB) is Associated with Improved Efficacy of Atezolizumab in 1L and 2L+ NSCLC Patients", Oral Presentation At: The 17th Annual World Conference on Lung Cancer; Vienna, Austria (Dec. 2016).

Labeling: PD-L1 IHC 28-8 pharmDx. Dako North America, 2016. (Accessed Oct. 20, 2016, at accessdata.fda.gov/cdrh_docs/pdf15/P150027c.pdf).

Lawrence, M. S., et al., "Mutational Heterogeneity in Cancer and the Search for New Cancer-Associated Genes," Nature 499(7457):214-218, Nature Publishing Group, Basingstoke (Jul. 2013).

Le, D.T., et al., "PD-1 Blockade in Tumors with Mismatch-Repair Deficiency," The New England Journal of Medicine 372(26):2509-2520, Massachusetts Medical Society, United States (Jun. 2015).

Lindeman, N. I., et al., "Molecular Testing Guideline for Selection of Lung Cancer Patients for EGFR and ALK Tyrosine Kinase Inhibitors: Guideline from the College of American Pathologists, International Association for the Study of Lung Cancer, and Association for Molecular Pathology," Journal of Thoracic Oncology 8(7):823-859, Elsevier, New York (Jul. 2013).

Liontos, M., et al., "DNA Damage, Tumor Mutational Load and Their Impact on Immune Responses Against Cancer," Annals of Translational Medicine 4(14):264, AME Publishing Company, Hong Kong (Jul. 2016).

Liu, S.Y., et al., "Ongoing Clinical Trials of PD-1 and PD-L1 Inhibitors for Lung Cancer in China," Journal of Hematology & Oncology, 10(1):136, Biomed Central, United Kingdom (Jul. 2017).

Masters, G.A., et al., "Systemic Therapy for Stage IV Non-Small-Cell Lung Cancer: American Society of Clinical Oncology Clinical Practice Guideline Update," Journal of Clinical Oncology 33(30):3488-3515, American Society of Clinical Oncology, United States (Oct. 2015).

McCabe, K.E. and Wu, A.M., "Positive Progress in ImmunoPET—not Just a Coincidence," Cancer Biotherapy & Radiopharmaceuticals 25(3):253-261, Mary Ann Liebert, Inc, United States (Jun. 2010).

McDermott, D. F., and Atkins, M. B., "PD-1 as a Potential Target in Cancer Therapy," Cancer Medicine 2(5):662-673, John Wiley & Sons Ltd., United States (Oct. 2013).

McGranahan, N., et al., "Clonal Neoantigens Elicit T Cell Immunoreactivity and Sensitivity to Immune Checkpoint Blockade," Science 351(6280):1463-1469, American Association for the Advancement of Science, United States (Mar. 2016).

(56) References Cited

OTHER PUBLICATIONS

Meng, X., et al., "Predictive Biomarkers in PD-1/PD-L1 Checkpoint Blockade Immunotherapy," Cancer Treatment Reviews 41(10):868-876, Elsevier, Amsterdam (Dec. 2015).

Merck & Co., Inc., Keytruda ® (Pembrolizumab) Prescribing Information, accessed at https://www.merck.com/product/USA/pi_circulars/k/keytruda/keytruda_pi.pdf on Mar. 2, 2021, 100 pages.

Mok, T. S. K., et al., "Blood First Line Ready Screening Trial (B-FIRST) and Blood First Assay Screening Trial (BFAST) Enable Clinical Development of Novel Blood-Based Biomarker Assays for Tumor Mutational Burden (TMB) and Somatic Mutations in 1L Advanced or Metastatic NSCLC," Annals of Oncology 28(5):v494-v495, Elsevier Ltd., on behalf of the European Society for Medical Oncology, United Kingdom (Sep. 2017).

Morabito, A., et al., "Treatment of Small Cell Lung Cancer," Critical Reviews in Oncology/Hematology 91(3):257-270, Elsevier Scientific Publishers, Amsterdam (Sep. 2014).

National Cancer Institute, Colorectal Cancer, available at: http://www.cancer.gov/types/colorectal, last visited Dec. 9, 2015.

National Cancer Institute, Head and Neck Cancers, available at https://www.cancer.gov/types/head-and-neck/head-neck-fact-sheet, last visited Dec. 9, 2015.

National Cancer Institute, Ovarian Epithelial, Fallopian Tube, and Primary Peritoneal Cancer Treatment (PDQ®), available at https://www.cancer.gov/types/ovarian/patient/ovarian-epithelial-treatment-pdq, last visited Dec. 9, 2015, 5 pages.

National Cancer Institute, Skin Cancer (Including Melanoma), available at http://www.cancer.gov/types/skin, last visited Dec. 9, 2015.

National Comprehensive Cancer Network, "NCCN Clinical Practice Guidelines in Oncology Non-Small Cell Lung Cancer Version3. 2014," nccn.org, accessed at http://www.24hmb.com/voimages/web_image//upload/file/20140416/28501397633488076.pdf, accessed on Feb. 21, 2017, 148 pages.

NCCN Guidelines® (2014), available at http://www.nccn.org/professionals/physician_gls/f_guidelines.asp, last accessed May 14, 2014, 3 pages.

NCCN Guidelines®, "NCCN Clinical Practice Guidelines in Oncology," NCCN.org, accessed at https://www.nccn.org/professionals/physician_gls/default.aspx on Nov. 4, 2020, 3 pages.

NCT02367781, "A Study of Atezolizumab in Combination With Carboplatin Plus (+) Nab-Paclitaxel Compared With Carboplatin+Nab-Paclitaxel in Participants With Stage IV Non-Squamous Non-Small Cell Lung Cancer (NSCLC) (IMpower130)," accessed at https://clinicaltrials.gov/ct2/show/NCT02367781 on Nov. 4, 2020, 6 pages.

NCT02453282, "Phase III Open Label First Line Therapy Study of MEDI 4736 (Durvalumab) With or Without Tremelimumab Versus SOC in Non Small-Cell Lung Cancer (NSCLC). (MYSTIC)," accessed at https://clinicaltrials.gov/ct2/show/NCT02453282 on Nov. 4, 2020, 10 pages.

NCT02477826, "An Investigational Immuno-therapy Trial of Nivolumab, or Nivolumab Plus Ipilimumab, or Nivolumab Plus Platinum-doublet Chemotherapy, Compared to Platinum Doublet Chemotherapy in Patients With Stage IV Non-Small Cell Lung Cancer (NSCLC) (CheckMate 227)," accessed at https://clinicaltrials.gov/ct2/show/NCT02477826 on Nov. 4, 2020, 5 pages.

NCT02578680, "Study of Pemetrexed+Platinum Chemotherapy With or Without Pembrolizumab (MK-3475) in Participants With First Line Metastatic Nonsquamous Non-small Cell Lung Cancer (MK-3475-189/KEYNOTE-189)," accessed at https://clinicaltrials.gov/ct2/show/NCT02578680 on Nov. 4, 2020, 8 pages.

NCT02869789, "An Investigational Immuno-therapy Study for Safety of Nivolumab in Combination With Ipilimumab to Treat Advanced Cancers," accessed at https://clinicaltrials.gov/ct2/show/NCT02869789 on Nov. 4, 2020, 4 pages.

Ng S. B., et al., "Targeted Capture and Massively Parallel Sequencing of 12 Human Exomes," Nature 461(7261):272-276, Nature Publishing Group, Basingstoke. (Sep. 2009).

Oken, M.M., et al., "Toxicity and Response Criteria of the Eastern Cooperative Oncology Group," American Journal of Clinical Oncology 5(6):649-655, Lippincott Williams & Wilkins, United States (1982).

Olafsen, T., et al., "ImmunoPET Imaging of B-Cell Lymphoma Using 124I-Anti-CD20 scFv Dimers (Diabodies)," Protein Engineering, Design & Selection 23(4):243-249, Oxford University Press, United Kingdom (Apr. 2010).

Ott, P. A., et al., "Pembrolizumab in Patients With Extensive-Stage Small-Cell Lung Cancer: Results From the Phase Ib KEYNOTE-028 Study," Journal of Clinical Oncology 35(34):3823-3829, American Society of Clinical Oncology, United States (Dec. 2017).

Overman, M. J., et al., "Nivolumab in Patients with Metastatic DNA Mismatch Repair-Deficient or Microsatellite Instability-High Colorectal Cancer (CheckMate 142): An Open-Label, Multicentre, Phase 2 Study," The Lancet Oncology 18(9):1182-1191, Lancet Publishing Group, United Kingdom (Sep. 2017).

Pacheco, J. M. and Camidge D. R., "KEYNOTE-028: How Do We Use Immunotherapy in Small Cell Lung Cancer?," Translational Lung Cancer Research 6(Suppl 1):S84-S87, Pioneer Bioscience Publishing Company, Hong Kong (Dec. 2017).

Pardoll, D.M., "The Blockade of Immune Checkpoints in Cancer Immunotherapy," Nature Reviews Cancer 12(4):252-264, Nature Publishing Group, United Kingdom (Mar. 2012).

Patel, J.D., et al., "PointBreak: A Randomized Phase III Study of Pemetrexed Plus Carboplatin and Bevacizumab Followed by Maintenance Pemetrexed and Bevacizumab Versus Paclitaxel Plus Carboplatin and Bevacizumab Followed by Maintenance Bevacizumab in Patients with Stage IIIB or IV Nonsquamous Non-Small-Cell Lung Cancer," Journal of Clinical Oncology 31:4349-4357, American Society of Clinical Oncology, Alexandria (Dec. 2013).

Pawel, J. V., et al., "Randomized Phase III Trial of Amrubicin Versus Topotecan as Second-Line Treatment for Patients with Small-Cell Lung Cancer," Journal of Clinical Oncology 32(35):4012-4019, American Society of Clinical Oncology, Alexandria (Dec. 2014).

Pawel, J. V., et al., "Topotecan Versus Cyclophosphamide, Doxorubicin, and Vincristine for the Treatment of Recurrent Small-Cell Lung Cancer," Journal of Clinical Oncology 17(2):658-667, American Society of Clinical Oncology, Alexandria (Feb. 1999).

Pawlik, T.M., et al., "Colorectal Carcinogenesis: MSI-H Versus MSI-L," Disease Markers 20(4-5):199-206, Hindawi Pub. Corp, United States (2004).

Paz-Ares, L., et al., "Necitumumab Plus Pemetrexed and Cisplatin as First-line Therapy in Patients With Stage Iv Non-squamous Non-small-cell Lung Cancer (Inspire): an Open-label, Randomised, Controlled Phase 3 Study," The Lancet Oncology 16(3):328-337, Lancet Publishing Group, United Kingdom (Mar. 2015).

Peters, S., et al., "Abstract CT082: Impact of Tumor Mutation Burden on the Efficacy of First-line Nivolumab in Stage Iv or Recurrent Non-small Cell Lung Cancer: An Exploratory Analysis of Checkmate 026," Proceedings: AACR Annual Meeting 2017 77(13_Suppl):CT082, American Association for Cancer Research, United States (Jul. 2017).

(56) References Cited

OTHER PUBLICATIONS

Philippidis, A., "Merck Melanoma Drug Is First PD-1 Inhibitor OK'd by FDA," GenEngNews.com, published Sep. 5, 2014, accessed at https://www.genengnews.com/topics/translational-medicine/merck-melanoma-drug-is-first-pd-1-inhibitor-okd-by-fda/ on Mar. 21, 2018, 2 pages, Mary Ann Liebert, Inc., United States (2014).

Exosome Diagnostics, Inc., "Plasma-Based Solid Tumor Mutation Panel" Liquid Biopsy, Exosomedx.com, accessed at URL:[https://web.archive.org/web/20161223185114/http://exosomedx.com/sites/default/files/uploads/diagnostics/pharma_services_051816_v4.pdf] on Jun. 16, 2021, 2 pages.

Plieth, J., "Bristol Makes Investors Squirm a Little More", Evaluate Vantage Jan. 24, 2019, XP55600286, URL:https://www.evaluate.com/vantage/articles/news/corporate-strategy/bristol-makes-investors-squirm-little-more.

Puglisi, M., et al., "Treatment Options for Small CellLung Cancer—Do We Have More Choice?, "British Journal of Cancer, 102(4):629-638, Nature Publishing Group on behalf of Cancer Research UK, United Kingdom (Feb. 2010).

Raedler, L.A., "Keytruda (Pembrolizumab): First PD-1 Inhibitor Approved for Previously Treated Unresectable or Metastatic Melanoma," American Health & Drug Benefits 8:96-100, Engage Healthcare Communications LLC, United States (2015).

Ramalingam, S.S., et al., "Abstract CT078: Tumor Mutational Burden (TMB) as a Biomarker for Clinical Benefit from Dual Immune Checkpoint Blockade with Nivolumab (nivo) + Ipilimumab (ipi) in First-Line (1L) Non-Small Cell Lung Cancer (NSCLC): Identification of TMB Cutoff from CheckMate 568," Proceedings of 2018 AACR Annual Meeting 78(13):CT078, American Association for Cancer Research, United States (Jul. 2018).

Ready, N., et al., "First-Line Nivolumab Plus Ipilimumab in Advanced Non-Small-Cell Lung Cancer (CheckMate 568): Outcomes by Programmed Death Ligand 1 and Tumor Mutational Burden as Biomarkers", Journal of Clinical Oncology : Official Journal of the American Society of Clinical Oncology 37(12):992-1000, American Society of Clinical Oncology, United States (Apr. 2019) XP55600306.

Reck, M., et al., "Nivolumab Plus Ipilimumab Versus Chemotherapy as First-Line Treatment in Advanced Non-Small-Cell Lung Cancer with High Tumour Mutational Burden: Patient-Reported Outcomes Results from the Randomised, Open-Label, Phase III CheckMate 227 Trial", European Journal of Cancer 116:137-147, Pergamon Press, United Kingdom (Jun. 2019) XP55600301.

Reck,M., et al., "Pembrolizumab Versus Chemotherapy for PD-L1-Positive Non-small-Cell Lung Cancer," The New England journal of medicine 375(19):1823-1833, Massachusetts Medical Society, United States (Nov. 2016).

Remon,J., et al., "Successes and Failures: What Did We Learn From Recent First-Line Treatment Immunotherapy Trials in Non-small Cell Lung Cancer?," BMC medicine 15(1):55, BioMed Central, United Kingdom (Mar. 2017).

Retseck,J., et al., "Phenotypic and Functional Testing of Circulating Regulatory T Cells in Advanced Melanoma Patients Treated With Neoadjuvant Ipilimumab," Journal for immunotherapy of cancer 4:38, BioMed Central, United Kingdom (Jun. 2016).

Reu, S and Huber, R. M., et al., "Small Cell Lung Cancer," The Oncologist 23(5): 340-346, Springer (Mar. 2017).

Ribas, A., "Anti-CTLA4 Antibody Clinical Trials in Melanoma," Update on Cancer Therapeutics 2(3):133-139, Elsevier, Ltd, United Kingdom (Sep. 2007).

Richman S., "Deficient Mismatch Repair: Read All About It," International Journal of Oncology 47(4):1189-1202, D.A. Spandidos, Greece. (Oct. 2015).

Rini, B.I., et al., "Phase 1 Dose-escalation Trial of Tremelimumab Plus Sunitinib in Patients with Metastatic Renal Cell Carcinoma," Cancer 117(14):758-767, Wiley, United States (Feb. 2011).

Rizvi, N. A., et al., "Supplementary Materials for Mutational Landscape Determines Sensitivity to PD-1 Blockade in Non-Small Cell Lung Cancer," Science, accessed at https://science.sciencemag.org/content/sci/suppl/2015/03/11/science.aaa1348.DC1/Rizvi-SM.pdf on Dec. 18, 2017, 31 pages, American Association for the Advancement of Science, United States (2015).

Rizvi, N.A., et al., "Mutational Landscape Determines Sensitivity to PD-1 Blockade in Non-Small Cell Lung Cancer," Science 348(6230):124-128., American Association for the Advancement of Science, United States (Apr. 2015).

Rizvi,H., et al., "Molecular Determinants of Response to Anti-Programmed Cell Death (PD)-1 and Anti-Programmed Death-Ligand 1 (PD-L1) Blockade in Patients With Non-Small-Cell Lung Cancer Profiled With Targeted Next-Generation Sequencing," Journal of clinical oncology : official journal of the American Society of Clinical Oncology 36(7):633-641, Grune & Stratton, United States (Mar. 2018).

Roche, H., "FDA Approves Foundation Medicine's FoundationOne CDx, the First Pan-Tumour Comprehensive Genomic Profiling Assay Incorporating a Broad Range of Companion Diagnostics," Roche.com, accessed at https://www.roche.com/investors/updates/inv-update-2017-12-04.htm on Dec. 5, 2017, 4 pages (Dec. 2017).

Rooney M. S., et al., "Molecular and Genetic Properties of Tumors Associated with Local Immune Cytolytic Activity," Cell 160(1-2):48-61, Cell Press, Cambridge. (Jan. 2015).

Rosenberg, J. E., et al., "Atezolizumab in Patients with Locally Advanced and Metastatic Urothelial Carcinoma Who Have Progressed Following Treatment with Platinum-Based Chemotherapy: a Single-Arm, Multicentre, Phase 2 Trial," Lancet 387(10031):1909-1920, Onwhyn, London (May 2016).

Rosenberg, J.E., et al., "Supplement to Atezolizumab in patients with locally advanced and metastatic urothelial carcinoma who have progressed following treatment with platinum-based chemotherapy: a single-arm, multicentre, phase 2 trial," The Lancet, accessed fromhttps://ars.els-cdn.com/content/image/1-s2.0-S0140673616005614-mmc1.pdf on Nov. 3, 2020, 25 pages, Elsevier Ltd., United Kingdom (May 2016).

Roszik J., et al., "Novel Algorithmic Approach Predicts Tumor Mutation Load and Correlates with Immunotherapy Clinical Outcomes Using a Defined Gene Mutation Set," BMC Medicine 14(1):168, BioMed Central, London. (Oct. 2016).

Saunders, C.T., et al., "Strelka: Accurate Somatic Small-variant Calling From Sequenced Tumor-Normal Sample Pairs," Bioinformatics 28(14):1811-1817, Oxford : Oxford University Press, United Kingdom (Jul. 2012).

Scagliotti, G.V., et al., "Phase III Study Comparing Cisplatin Plus Gemcitabine with Cisplatin Plus Pemetrexed in Chemotherapy-naive Patients with Advanced-stage Non-small-cell Lung Cancer," Journal of Clinical Oncology 26(21):3543-3551, American Society of Clinical Oncology, United States (Jul. 2008).

(56) References Cited

OTHER PUBLICATIONS

Schaer, D.A., et al., "Modulation of GITR for Cancer Immunotherapy," Current Opinion in Immunology 24(2):217-224, Elsevier Ltd., United Kingdom (Apr. 2012).

Schumacher, T. N., et al., "Neoantigens Encoded in the Cancer Genome," Current Opinion in Immunology 41:98-103, Elsevier, London (Aug. 2016).

Schumacher, T.N. and Schreiber, R.D., "Neoantigens in Cancer Immunotherapy," Science 348(6230):69-74, American Association for the Advancement of Science, United States (Apr. 2015).

Sharma, P. and Allison, J. P., "The Future of Immune Checkpoint Therapy," Science 348(6230):56-61, American Association for the Advancement of Science, Washington (Apr. 2015).

Sharma, P., et al., "Nivolumab in Metastatic Urothelial Carcinoma After Platinum Therapy (CheckMate 275): A Multicentre, Single-Arm, Phase 2 Trial," The Lancet Oncology 18(3):312-322, Lancet Publishing Group, United Kingdom (Mar. 2017).

Sharma, P., et al., "Nivolumab monotherapy in recurrentmetastatic urothelial carcinoma (CheckMate 032): a multicentre, open-label,two-stage, multi-arm, phase 1/2 trial, "The Lancet Oncology, 17(11):1590-1598, The Lancet Publishing Group, United Kingdom (Nov. 2016).

Shien, K., et al., "Predictive Biomarkers of Response to PD-1/PD-L1 Immune Checkpoint Inhibitors in Non-Small Cell Lung Cancer," Lung Cancer 99:79-87, Elsevier Ireland Ltd., Netherlands (Sep. 2016).

Siegel, R., et al., "Cancer Statistics, 2014," CA: A Cancer Journal for Clinicians 64(1):9-29, Wiley, United States (Jan. 2014).

Singal, G., et al., "Development and Validation of a Real-World Clinicogenomic Database," Journal of Clinical Oncology 35(15): 2514, American Society of Clinical Oncology, United States (May 2017).

Sjoblom, T., et al., "The Consensus Coding Sequences of Human Breast and Colorectal Cancers," Science 314(5797):268-274, American Association for the Advancement of Science, United States (Oct. 2006).

Snyder, A., et al., "Genetic Basis for Clinical Response to CTLA-4 Blockade in Melanoma," The New England Journal of Medicine 371(23):2189-2199, Massachusetts Medical Society, United States (Dec. 2014).

Socinski, M., et al., "NSCLC, Metastatic Checkmate 026: A Phase 3 Trial of Nivolumab vs Investigator's Choice (IC) of Platinum-Based Doublet Chemotherapy (PT-DC) as First-Line Therapy for Stage IV/Recurrent Programmed Death Ligand 1 (PD-L1)-Positive NSCLC," Annals of Oncology 27(6):vi552-vi587, Elsevier Ltd., United Kingdom (2016).

Socinski, M.A., et al., "Weekly Nab-paclitaxel in Combination With Carboplatin Versus Solvent-based Paclitaxel Plus Carboplatin as First-line Therapy in Patients With Advanced Non-small-cell Lung Cancer: Final Results of a Phase III Trial," Journal of Clinical Oncology 30(17):2055-2062, American Society of Clinical Oncology, United States (Jun. 2012).

Solange, P., et al., "Abstract CT082: Impact of Tumor Mutation Burden on the Efficacy of First-Line Nivolumab in Stage IV or Recurrent Non-Small Cell Lung Cancer: An Exploratory Analysis of CheckMate 026," Proceedings of 2017 AACR Annual Meeting 77(13): CT082, American Association for Cancer Research, United States (Jul. 2017).

Stratton, M. R., et al., "The Cancer Genome," Nature 458(7239):719-724, Nature Publishing Group, Basingtoke (Apr. 2009).

Sun, J.X., et al., "A Computational Approach to Distinguish Somatic vs. Germline Origin of Genomic Alterations from Deep Sequencing of Cancer Specimens Without a Matched Normal," PLoS Computational Biology 14(2):e1005965, Public Library of Science, United States (Feb. 2018).

Szustakowski, J., et al., "Abstract 5528: Evaluation of tumor mutation burden as a biomarker for immune checkpoint inhibitor efficacy: A calibration study of whole-exome sequencing with FoundationOne®," Proceedings of 2018 AACR Annual Meeting 78(13_Supplement): Abstract 5528, Apr. 14-18, 2018, 3 pages, American Association for Cancer Research, United States.

Tarhini, A.A., et al., "Immune Monitoring of the Circulation and the Tumor Microenvironment in Patients with Regionally Advanced Melanoma Receiving Neoadjuvant Ipilimumab," PLoS One Peer-reviewed journal 9(2):e87705, Public Library of Science, United States (Feb. 2014).

Taube, J.M., et al., "Colocalization of Inflammatory Response with B7-H1 Expression in Human Melanocytic Lesions Supports an Adaptive Resistance Mechanism of Immune Escape," Science Translational Medicine 4(127):127ra37, American Association for the Advancement of Science, United States (Mar. 2012).

Thatcher, N., et al., "Necitumumab Plus Gemcitabine and Cisplatin Versus Gemcitabine and Cisplatin Alone as First-line Therapy in Patients With Stage Iv Squamous Non-small-cell Lung Cancer (SQUIRE): an Open-label, Randomised, Controlled Phase 3 Trial," The Lancet Oncology 16(7):763-774, The Lancet Publishing Group, United Kingdom (Jul. 2015).

Topalian, S. L., et al., "Mechanism-Driven Biomarkers to Guide Immune Checkpoint Blockade in Cancer Therapy," Nature Reviews Cancer 16(5):275-287, Nature Publishing Group, London (May 2016).

Topalian, S.L., et al., "Safety, Activity and Immune Correlates of Anti-PD-1 Antibody in Cancer," The New England Journal of Medicine 366(26):2443-2454, Massachusetts Medical Society, United States (Jun. 2012).

Topalian, S.L., et al., "Nivolumab (anti-PD-1; BMS-936558; ONO-4538) in patients with advanced solid tumors: Survival and long-term safety in a phase I trial, Journal of Clinical Oncology 31(15_Suppl):3002-3002, American Society of Clinical Oncology, United States (May 2013), accessed at http://meetinglibrary.asco.org/content/113543-132," accessed on Feb. 2, 2015, 2 pages.

Topalian, S.L., et al., "Targeting the PD-1/B7-H1(PD-L1) Pathway to Activate Anti-tumor Immunity," Current Opinion in Immunology 24(2):207-212, Elsevier, United Kingdom (Apr. 2012).

Topalian, S.L., et al., "Survival, Durable Tumor Remission, and Long-term Safety in Patients with Advanced Melanoma Receiving Nivolumab," Journal of Clinical Oncology 32(10):1020-1030, American Society of Clinical Oncology, United States (Apr. 2014).

Ulahannan, D., et al., "Technical and Implementation Issues in Using Next-Generation Sequencing of Cancers in Clinical Practice," British Journal of Cancer 109(4):827-835, Nature Publishing Group on behalf of Cancer Research UK, London (Aug. 2013).

U.S. Food And Drug Administration, "FDA Announces Approval, CMS Proposes Coverage of First Breakthrough-Designated Test to Detect Extensive Number of Cancer Biomarkers," FDA.gov, accessed at URL:[https://www.fda.gov/NewsEvents/Newsroom/PressAnnouncements/ucm587273.htm] on Mar. 2, 2021, 2 pages (Nov. 2017).

(56) References Cited

OTHER PUBLICATIONS

U.S. Food And Drug Administration, "FDA Unveils a Streamlined Path for the Authorization of Tumor Profiling Tests Alongside its Latest Product Action," FDA.gov, accessed at URL:[https://www.fda.gov/NewsEvents/Newsroom/PressAnnouncements/ucm585347.htm] on Mar. 2, 2021, 2 pages (Nov. 2017).

Van Allen, E. M., et al., "Clinical Analysis and Interpretation of Cancer Genome Data," Journal of Clinical Oncology 31(15):1825-1833, American Society of Clinical Oncology, Alexandria (May 2013).

Van Allen, E. M., et al., "Genomic Correlates of Response to CTLA-4 Blockade in Metastatic Melanoma," Science 350(6257):207-211, American Association for the Advancement of Science, Washington (Oct. 2015).

Veloso A., et al., "Abstract 854: Mutation Load Measured Using a 315 Gene Panel Predicts Genome-Wide Mutation Load," Cancer Research 76(14):1-4, AACR 107th Annual Meeting, New Orleans (Apr. 2016).

Vogelstein, B., et al., "Cancer Genome Landscapes," Science 339(6127):1546-1558, American Association for the Advancement of Science, United States (Mar. 2013).

Wakelee, H.A., et al., "Survival Differences by Sex for Patients with Advanced Non-small Cell Lung Cancer on Eastern Cooperative Oncology Group Trial 1594," Journal of Thoracic Oncology 1(5):441-446, Elsevier, United States (Jun. 2006).

Wang, C., et al., "In Vitro Characterization of the Anti-PD-1 Antibody Nivolumab, BMS-936558, and in Vivo Toxicology in Non-human Primates," Cancer Immunology Research 2(9):846-856, American Association for Cancer Research, United States (Sep. 2014).

Wang, V. E., et al., "Checkpoint Inhibitor is Active Against Large Cell Neuroendocrine Carcinoma with High Tumor Mutation Burden," Journal for Immunotherapy of Cancer 5(1):75, BMJ Publishing Group Ltd, London (Sep. 2017).

Warner, J. L., et al., "Integrating Cancer Genomic Data Into Electronic Health Records," Genome Medicine 8(1):113, BioMed Central, London (Oct. 2016).

Weber, J.A., et al. (2016) Sentieon DNA pipeline for variant detection—Software-only solution, over 20x faster than GATK 3.3 with identical results. PeerJ PrePrints 4:e1672v2.

Wolchok, J.D., et al., "Nivolumab Plus Ipilimumab in Advanced Melanoma," The New England Journal of Medicine 369(2):122-133, Massachusetts Medical Society, United States (Jul. 2013).

Yap, T. A., "Drug Discovery in Advanced Prostate Cancer: Translating Biology Into Therapy," Nature Reviews Drug Discovery 15(10):699-718, Nature Publishing Group, London (Oct. 2016).

Yap, T.A., et al., "Intratumor Heterogeneity: Seeing the Wood for the Trees," Science Translational Medicine 4(127):127ps10, American Association for the Advancement of Science, United States (Mar. 2012).

Zehir, A., et al., "Mutational Landscape of Metastatic Cancer Revealed From Prospective Clinical Sequencing of 10,000 Patients," Nature medicine 23(6):703-713, Nature Publishing Company, United States (Jun. 2017).

Zhang, F., et al., "Structural Basis of a Novel PD-L1 Nanobody for Immune Checkpoint Blockade," Cell Discovery, 3:17004, Nature Publishing Group, United Kingdom (Mar. 2017).

Zinner, R.G., et al., "PRONOUNCE: Randomized, Open-label, Phase Iii Study of First-line Pemetrexed + Carboplatin Followed by Maintenance Pemetrexed Versus Paclitaxel + Carboplatin + Bevacizumab Followed by Maintenance Bevacizumab in Patients Ith Advanced Nonsquamous Non-small-cell Lung Cancer," Journal of Thoracic Oncology 10(1):134-142, Elsevier, United States (Jan. 2015).

U.S. Appl. No. 62/479,817, Geese, W. J., et al., filed Mar. 31, 2017 (Not Published) (Now Expired).

U.S. Appl. No. 62/582,146, Geese, W. J., et al., filed Nov. 6, 2017 (Not Published) (Now Expired).

NCCN Guidelines, Version 3.2014—Non-Small Cell Lung Cancer, available at: http://www.nccn.org/professionals/physician_gls_pdf/nscl.pdf, last accessed May 14, 2014.

Third Party Submission mailed May 21, 2021, in U.S. Appl. No. 16/499,540, Bhagavatheeswaran, P.S. et al., filed Sep. 30, 2019, 17 pages.

Centene Corporation, "Clinical Policy: Nivolumab (Opdivo)," accessed online at URL:[healthnet.com/static/general/unprotected/html/national/pa_guidelines/2306.pdf] on Jan. 7, 2015, 11 pages (2015).

Vanderbilt-Ingram Cancer Center, Study NCT03023904, "Nivolumab In Treating Patients With Stage IV or Recurrent Lung Cancer With High Mutation Loads," ClinicalTrials.gov, accessed online at URL:[clinicaltrials.gov/ct2/show/record/NCT03023904] on Jan. 13, 2017, 4 pages (2017).

Johnson, D. B., et al., "Targeting Next Generation Sequencing Identifies Markers of Response to PD-1 Blockade," Cancer Immunol Res 4(11):959-967 and Supplemental Tables and Figures, American Association for Cancer Research, United States (Sep. 2016).

Third Party Observation mailed Dec. 16, 2021, in European Patent Application No. 18796809.4, filed Oct. 15, 2018, 11 pages.

Caris Molecular Intelligence®: "Total Mutational Load—Immune Checkpoint Inhibitors Response," 2 pages (Aug. 10, 2016).

Third Party Observation mailed Jan. 20, 2022, in European Patent Application No. 18720818.6, filed Mar. 30, 2018, 5 pages.

"BMS to Use Foundation Medicine Platform in Immuno-Oncology Partnership," GEN Genetic Engineering & Biotechnology News, Genengnews.com, accessed at URL:[https://www.genengnews.com/topics/drug-discovery/bms-to-use-foundation-medicine-platform-in-immuno-oncology-partnership/], 3 pages (Mar. 30, 2017).

Bristol Myers Squibb, "Bristol Myers Squibb Statement on Opdivo (nivolumab) Small Cell Lung Cancer U.S. Indication, News.BMS.com, accessed at URL:[https://news.bms.com/news/details/2020/Bristol-Myers-Squibb-Statement-on-Opdivo-nivolumab-Small-Cell-Lung-Cancer-US-Indication/default.aspx," 9 pages (Dec. 29, 2020).

"FoundationOne CDx Overview of Companion Diagnostic Products," China Device Evaluation, accessed at URL: [https://mp.weixin.qq.com/s?_biz=MzUyOTE2NTg1MQ-&mid=2247484136&idx=4&sn=b4279461b3e1cfbd54f613c25875b56f&chksm=fa64799ccd13f08aca76bfa49aa3185b942e3b6353a0a54b2560298cc90d18fa99b57033c589&scene=21#wechat_redirect] on Dec. 21, 2017, 5 pages.

FDA Approval Order and Review Summary for "FoundationOne CDxTM," FDA Notice of Approval: Nov. 30, 2017, accessed at URL:[https://www.accessdata.fda.gov/cdrh_docs/pdf17/P170019A.pdf; https://www.accessdata.fda.gov/cdrh_docs/pdf17/P170019B.pdf], 63 pages (Nov. 30, 2017).

Third Party Submission mailed Jun. 3, 2021, in U.S. Appl. No. 16/756,157, Bhagavatheeswaran, P.S. et al., filed Apr. 15, 2020, 16 pages.

(56) References Cited

OTHER PUBLICATIONS

Non-Final Office Action dated Mar. 28, 2022, in U.S. Appl. No. 16/499,540, Bhagavatheeswaran, P.S. et al., filed Sep. 30, 2019, 22 pages.
Final Office Action dated Sep. 7, 2022, in U.S. Appl. No. 16/499,540, Bhagavatheeswaran, P.S. et al., filed Sep. 30, 2019, 27 pages.
Non-Final Office Action dated Mar. 9, 2022, in U.S. Appl. No. 16/756,157, Bhagavatheeswaran, P.S. et al., filed Apr. 15, 2020, 10 pages.
Final Office Action dated Jun. 16, 2022, in U.S. Appl. No. 16/756,157, Bhagavatheeswaran, P.S. et al., filed Apr. 15, 2020, 11 pages.
Non-Final Office Action dated Nov. 10, 2022, in U.S. Appl. No. 17/044,163, Bhagavatheeswaran, P.S et al., filed Sep. 30, 2020, 38 pages.

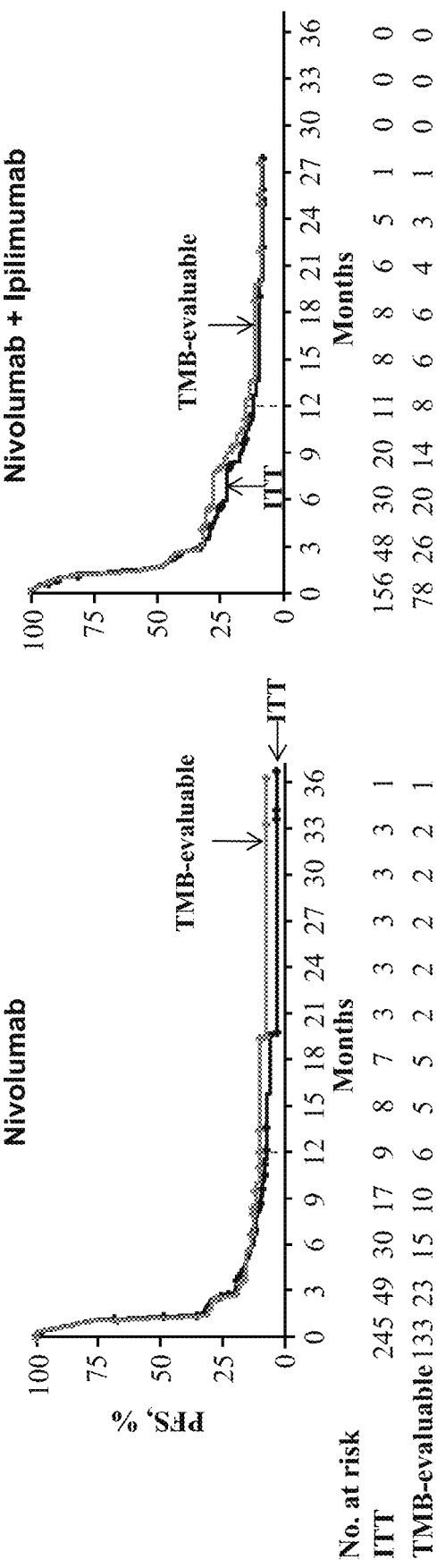
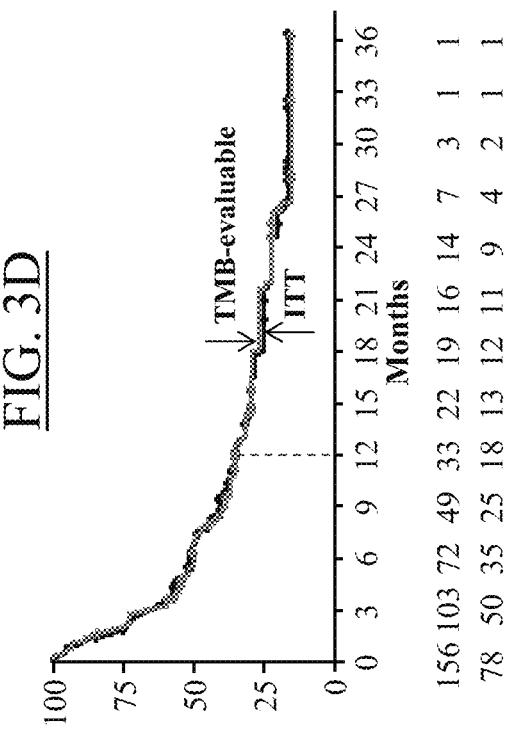
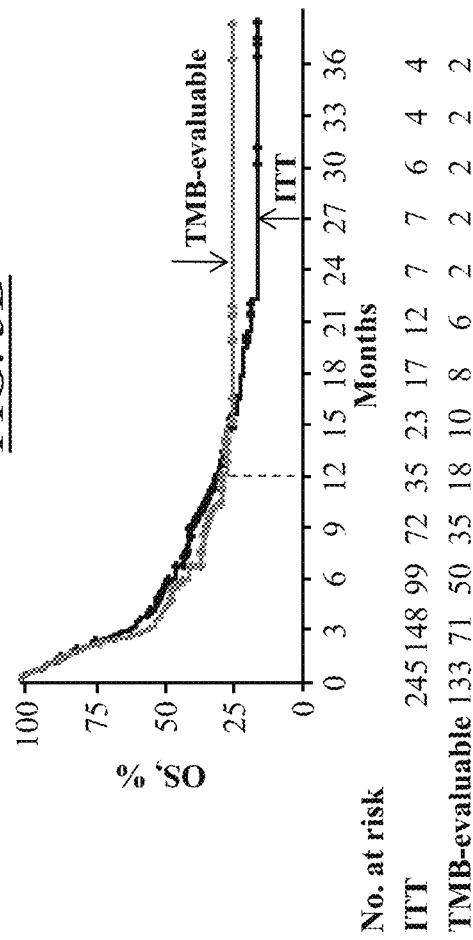

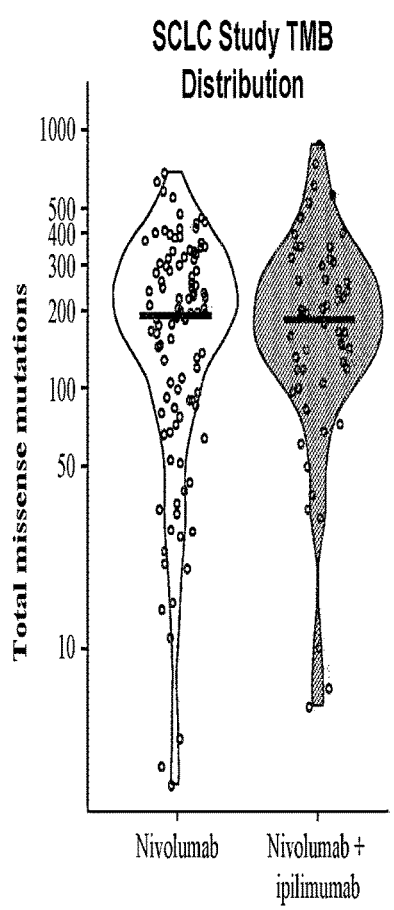
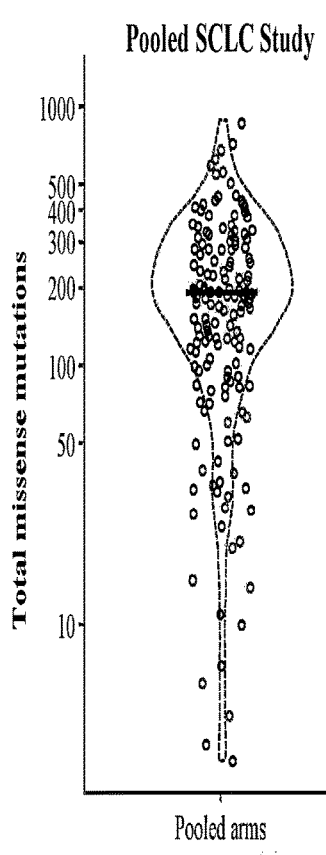
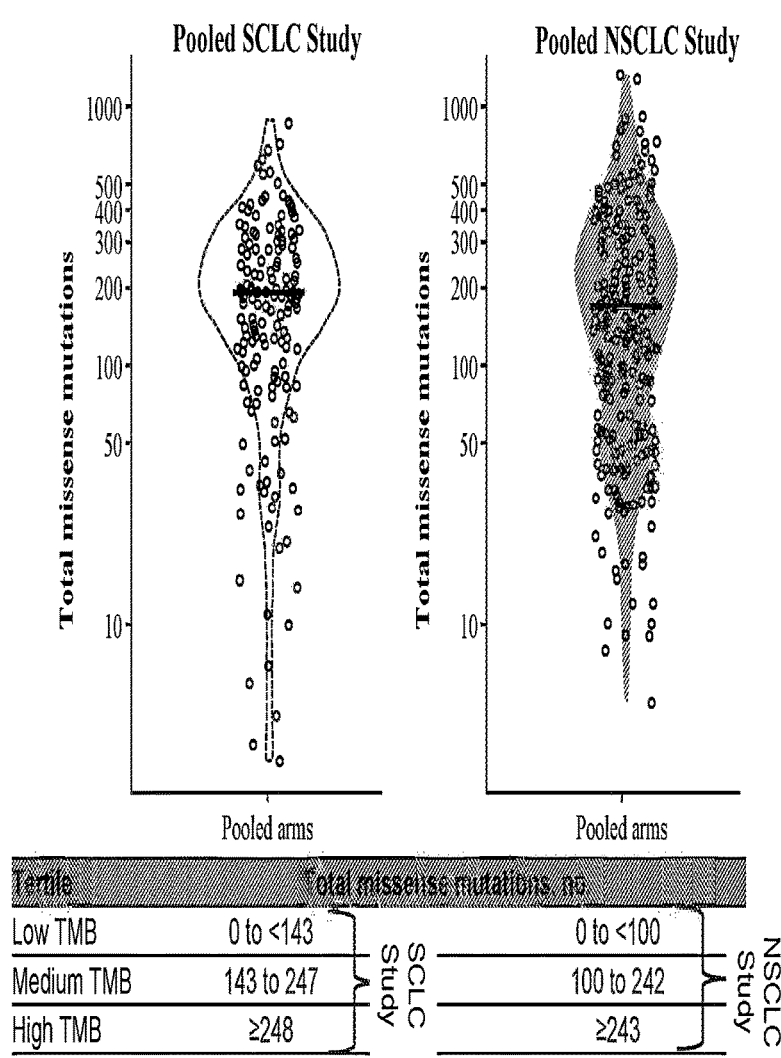
FIG. 4A SCLC Study TMB Distribution
FIG. 4B Pooled SCLC Study
FIG. 4C Pooled NSCLC Study Nivolumab Nivolumab + ipilimumab Best Overall Response

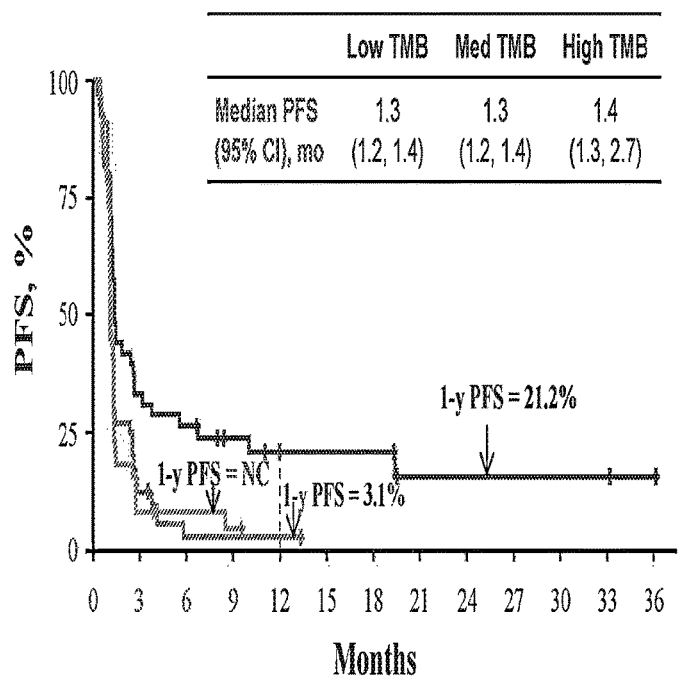
Median (95% CI) PFS, overall TMB-evaluable population: 1.4 (1.3, 1.4) months for nivolumab and 1.7 (1.4, 2.7) months for nivolumab + ipilimumab
NC = not calculable Median (95% CI) PFS, overall TMB-evaluable population: 1.4 (1.3, 1.4) months for nivolumab and 1.7 (1.4, 2.7) months for nivolumab + ipilimumab
NC = not calculable

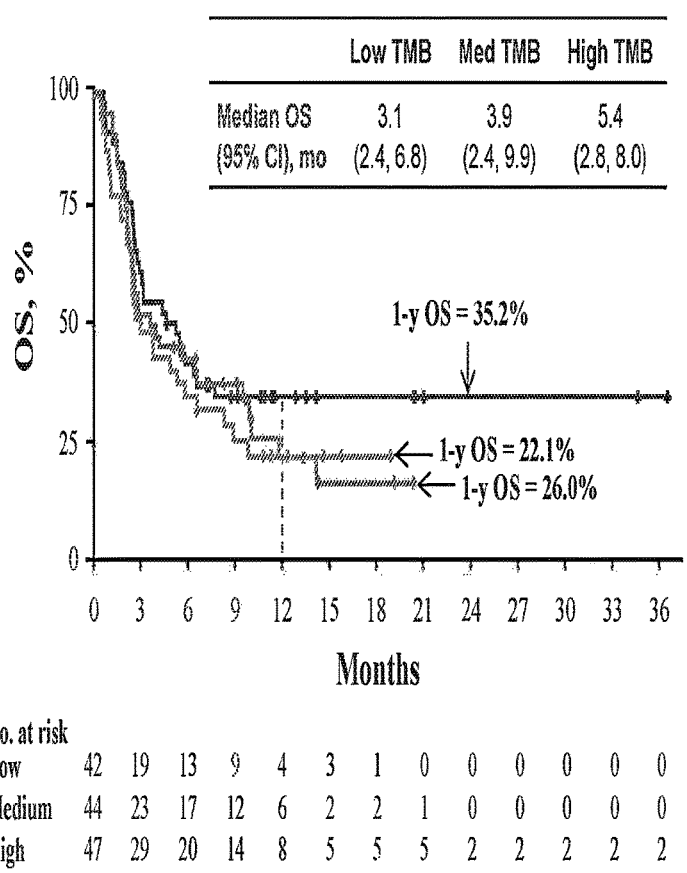
Median (95% CI) OS, overall TMB-evaluable population: 3.9 (2.8, 6.1) months for nivolumab and 7.0 (3.2, 8.8) months for nivolumab + ipilimumab
NR = not reached Median (95% CI) OS, overall TMB-evaluable population: 3.9 (2.8, 6.1) months for nivolumab and 7.0 (3.2, 8.8) months for nivolumab + ipilimumab
NR = not reached

SEQUENCE LISTING

```
Sequence total quantity: 10
SEQ ID NO: 1            moltype = AA  length = 123
FEATURE                 Location/Qualifiers
source                  1..123
                        mol_type = protein
                        organism = synthetic construct
```

```
REGION                          1..123
                                note = VH
SEQUENCE: 1
QVQLVESGGG VVQPGRSLRL SCAASGFTFS SYGMHWVRQA PGKGLEWVAV IWYEGSNKYY        60
ADSVKGRFTI SRDNSKNTLY LQMNSLRAED TAVYYCARGG SMVRGDYYYG MDVWGQGTTV       120
TVS                                                                    123

SEQ ID NO: 2             moltype = AA   length = 107
FEATURE                  Location/Qualifiers
source                   1..107
                         mol_type = protein
                         organism = synthetic construct
REGION                   1..107
                         note = VL
SEQUENCE: 2
AIQLTQSPSS LSASVGDRVT ITCRASQGIS SALAWYQQKP GKAPKLLIYD ASSLESGVPS        60
RFSGSGSGTD FTLTISSLQP EDFATYYCQQ FNSYPYTFGQ GTKLEIK                    107

SEQ ID NO: 3             moltype = AA   length = 123
FEATURE                  Location/Qualifiers
source                   1..123
                         mol_type = protein
                         organism = synthetic construct
REGION                   1..123
                         note = VH
SEQUENCE: 3
QVQLVESGGG VVQPGRSLRL SCAASGFTFS SYGFHWVRQA PGKGLEWVAV IWYAGSNKFY        60
ADSVKGRFTI SRDNSKNTLY LQMNSLRAED TAVYYCARGG QLDYYYYYVM DVWGQGTTVT       120
VSS                                                                    123

SEQ ID NO: 4             moltype = AA   length = 107
FEATURE                  Location/Qualifiers
source                   1..107
                         mol_type = protein
                         organism = synthetic construct
REGION                   1..107
                         note = VL
SEQUENCE: 4
DIQMTQSPSS LSASVGDRVT ITCRASQGIS SWLAWYQQKP EKAPKSLIYA ASSLQSGVPS        60
RFSGSGSGTD FTLTISSLQP EDFATYYCQQ YNSYPYTFGQ GTKLEIK                    107

SEQ ID NO: 5             moltype = AA   length = 122
FEATURE                  Location/Qualifiers
source                   1..122
                         mol_type = protein
                         organism = synthetic construct
REGION                   1..22
                         note = VH
SEQUENCE: 5
VQLVESGGGV VQPGRSLRLS CAASGFTFSS YGMHWVRQAP GKGLEWVAVI WYAGSNKYYA        60
DSVKGRFTIS RDNSKNTLYL QMNSLRAEDT AVYYCARGGR IAVAFYYSMD VWGQGTTVTV       120
SS                                                                     122

SEQ ID NO: 6             moltype = AA   length = 107
FEATURE                  Location/Qualifiers
source                   1..107
                         mol_type = protein
                         organism = synthetic construct
REGION                   1..107
                         note = VL
SEQUENCE: 6
DIQMTQSPSS LSASVGDRVT ITCRASQGIS SWLAWYQQKP EKAPKSLIYA ASSLQSGVPS        60
RFSGSGSGTD FTLTISSLQP EDFATYYCQQ YNSYPYTFGQ GTKLEIK                    107

SEQ ID NO: 7             moltype = AA   length = 449
FEATURE                  Location/Qualifiers
source                   1..449
                         mol_type = protein
                         organism = synthetic construct
REGION                   1..449
                         note = heavy chain
SEQUENCE: 7
QVQLVESGGG VVQPGRSLRL SCAASGFTFS SYGMHWVRQA PGKGLEWVAV IWYEGSNKYY        60
ADSVKGRFTI SRDNSKNTLY LQMNSLRAED TAVYYCARGG SMVRGDYYYG MDVWGQGTTV       120
TVSSASTKGP SVFPLAPCSR STSESTAALG CLVKDYFPEP VTVSWNSGAL TSGVHTFPAV       180
LQSSGLYSLS SVVTVPSSNF GTQTYTCNVD HKPSNTKVDK TVERKCCVEC PPCPAPPVAG       240
PSVFLFPPKP KDTLMISRTP EVTCVVVDVS HEDPEVQFNW YVDGVEVHNA KTKPREEQFN       300
STFRVVSVLT VVHQDWLNGK EYKCKVSNKG LPAPIEKTIS KTKGQPREPQ VYTLPPSREE       360
```

```
MTKNQVSLTC LVKGFYPSDI AVEWESNGQP ENNYKTTPPM LDSDGSFFLY SKLTVDKSRW    420
QQGNVFSCSV MHEALHNHYT QKSLSLSPG                                     449

SEQ ID NO: 8           moltype = AA  length = 214
FEATURE                Location/Qualifiers
source                 1..214
                       mol_type = protein
                       organism = synthetic construct
REGION                 1..214
                       note = light chain
SEQUENCE: 8
AIQLTQSPSS LSASVGDRVT ITCRASQGIS SALAWYQQKP GKAPKLLIYD ASSLESGVPS     60
RFSGSGSGTD FTLTISSLQP EDFATYYCQQ FNSYPYTFGQ GTKLEIKRTV AAPSVFIFPP    120
SDEQLKSGTA SVVCLLNNFY PREAKVQWKV DNALQSGNSQ ESVTEQDSKD STYSLSSTLT    180
LSKADYEKHK VYACEVTHQG LSSPVTKSFN RGEC                                214

SEQ ID NO: 9           moltype = AA  length = 453
FEATURE                Location/Qualifiers
source                 1..453
                       mol_type = protein
                       organism = synthetic construct
REGION                 1..453
                       note = heavy chain
SEQUENCE: 9
QVQLVESGGG VVQPGRSLRL SCAASGFTFS SYGMHWVRQA PGKGLEWVAV IWYEGSNKYY     60
ADSVKGRFTI SRDNSKNTLY LQMNSLRAED TAVYYCARGG SMVRGDYYYG MDVWGQGTTV    120
TVSSASTKGP SVFPLAPSSK STSGGTAALG CLVKDYFPEP VTVSWNSGAL TSGVHTFPAV    180
LQSSGLYSLS SVVTVPSSSL GTQTYICNVN HKPSNTKVDK RVEPKSCDKT HTCPPCPAPE    240
AEGAPSVFLF PPKPKDTLMI SRTPEVTCVV VDVSHEDPEV KFNWYVDGVE VHNAKTKPRE    300
EQYNSTYRVV SVLTVLHQDW LNGKEYKCKV SNKALPSSIE KTISKAKGQP REPQVYTLPP    360
SREEMTKNQV SLTCLVKGFY PSDIAVEWES NGQPENNYKT TPPVLDSDGS FFLYSKLTVD    420
KSRWQQGNVF SCSVMHEALH NHYTQKSLSL SPG                                 453

SEQ ID NO: 10          moltype = AA  length = 214
FEATURE                Location/Qualifiers
source                 1..214
                       mol_type = protein
                       organism = synthetic construct
REGION                 1..214
                       note = light chain
SEQUENCE: 10
AIQLTQSPSS LSASVGDRVT ITCRASQGIS SALAWYQQKP GKAPKLLIYD ASSLESGVPS     60
RFSGSGSGTD FTLTISSLQP EDFATYYCQQ FNSYPYTFGQ GTKLEIKRTV AAPSVFIFPP    120
SDEQLKSGTA SVVCLLNNFY PREAKVQWKV DNALQSGNSQ ESVTEQDSKD STYSLSSTLT    180
LSKADYEKHK VYACEVTHQG LSSPVTKSFN RGEC                                214
```

METHODS OF TREATING TUMOR

REFERENCE TO SEQUENCE LISTING SUBMITTED ELECTRONICALLY

The content of the electronically submitted sequence listing (Name: 3338_0990003 SequenceListing_ST26.xml; Size: 15,406 bytes; and Date of Creation: May 29, 2023) is herein incorporated by reference in its entirety.

FIELD OF THE DISCLOSURE

The present disclosure provides a method for treating a subject afflicted with a tumor, e.g., SCLC, having a high tumor mutational burden (TMB) status comprising administering to the subject an anti-PD-1 antibody alone ("monotherapy") or an anti-PD-1 antibody in combination with an anti-CTLA-4 antibody.

BACKGROUND OF THE DISCLOSURE

Human cancers harbor numerous genetic and epigenetic alterations, generating neoantigens potentially recognizable by the immune system (Sjoblom et al., Science (2006) 314(5797):268-274). The adaptive immune system, comprised of T and B lymphocytes, has powerful anti-cancer potential, with a broad capacity and exquisite specificity to respond to diverse tumor antigens. Further, the immune system demonstrates considerable plasticity and a memory component. The successful harnessing of all these attributes of the adaptive immune system would make immunotherapy unique among all cancer treatment modalities.

Until recently, cancer immunotherapy had focused substantial effort on approaches that enhance anti-tumor immune responses by adoptive-transfer of activated effector cells, immunization against relevant antigens, or providing non-specific immune-stimulatory agents such as cytokines. In the past decade, however, intensive efforts to develop specific immune checkpoint pathway inhibitors have begun to provide new immunotherapeutic approaches for treating cancer, including the development of antibodies such as nivolumab and pembrolizumab (formerly lambrolizumab; USAN Council Statement, 2013) that bind specifically to the Programmed Death-1 (PD-1) receptor and block the inhibitory PD-1/PD-1 ligand pathway (Topalian et al., 2012a, b; Topalian et al., 2014; Hamid et al., 2013; Hamid and Carvajal, 2013; McDermott and Atkins, 2013).

PD-1 is a key immune checkpoint receptor expressed by activated T and B cells and mediates immunosuppression. PD-1 is a member of the CD28 family of receptors, which includes CD28, CTLA-4, ICOS, PD-1, and BTLA. Two cell surface glycoprotein ligands for PD-1 have been identified, Programmed Death Ligand-1 (PD-L1) and Programmed Death Ligand-2 (PD-L2), that are expressed on antigen-presenting cells as well as many human cancers and have been shown to downregulate T cell activation and cytokine secretion upon binding to PD-1. Inhibition of the PD-1/PD-L1 interaction mediates potent antitumor activity in preclinical models (U.S. Pat. Nos. 8,008,449 and 7,943,743), and the use of antibody inhibitors of the PD-1/PD-L1 interaction for treating cancer has entered clinical trials (Brahmer et al., 2010; Topalian et al., 2012a; Topalian et al., 2014; Hamid et al., 2013; Brahmer et al., 2012; Flies et al., 2011; Pardoll, 2012; Hamid and Carvajal, 2013).

Nivolumab (formerly designated 5C4, BMS-936558, MDX-1106, or ONO-4538) is a fully human IgG4 (S228P) PD-1 immune checkpoint inhibitor antibody that selectively prevents interaction with PD-1 ligands (PD-L1 and PD-L2), thereby blocking the down-regulation of antitumor T-cell functions (U.S. Pat. No. 8,008,449; Wang et al., 2014). Nivolumab has shown activity in a variety of advanced solid tumors, including renal cell carcinoma (renal adenocarcinoma, or hypernephroma), melanoma, and non-small cell lung cancer (NSCLC) (Topalian et al., 2012a; Topalian et al., 2014; Drake et al., 2013; WO 2013/173223).

The immune system and response to immuno-therapy are complex. Additionally, anti-cancer agents can vary in their effectiveness based on the unique patient characteristics. Accordingly, there is a need for targeted therapeutic strategies that identify patients who are more likely to respond to a particular anti-cancer agent and, thus, improve the clinical outcome for patients diagnosed with cancer.

SUMMARY OF THE DISCLOSURE

The present disclosure provides a method for treating a subject afflicted with a tumor derived from a small cell lung cancer (SCLC) comprising administering to the subject a therapeutically effective amount of an antibody or antigen-binding portion thereof that specifically binds to a Programmed Death-1 (PD-1) receptor and inhibits PD-1 activity ("an anti-PD-1 antibody"), wherein the tumor has a tumor mutational burden (TMB) status that is a high TMB. The present disclosure also provides a method for treating a subject afflicted with a tumor derived from an SCLC comprising administering to the subject a therapeutically effective amount of an anti-PD-1 antibody and an antibody or antigen-binding portion thereof that specifically binds to CTLA-4 ("an anti-CTLA-4 antibody"), wherein the tumor has a TMB status that is a high TMB. In some embodiments, the method further comprises measuring the TMB status of a biological sample obtained from the subject.

The present disclosure also provides a method of identifying a subject who is afflicted with a tumor derived from an SCLC and suitable for a therapy of an anti-PD-1 antibody comprising measuring a TMB status of a biological sample of the subject, wherein the TMB status is a high TMB. In one embodiment, the method further comprises administering to the subject the anti-PD-1 antibody. In one embodiment, the method further comprises administering to the subject the anti-PD-1 antibody and the anti-CTLA-4 antibody.

The present disclosure also provides a method of identifying a subject who is afflicted with a tumor derived from an SCLC and suitable for a combination therapy comprising an anti-PD-1 antibody and an anti-CTLA-4 antibody comprising measuring a TMB status of a biological sample of the subject, wherein the TMB status is a high TMB. In one embodiment, the method further comprises administering to the subject the anti-PD-1 antibody and the anti-CTLA-4 antibody.

In some embodiments, the TMB status is determined by sequencing nucleic acids in the tumor and identifying a genomic alteration in the sequenced nucleic acids. In some embodiments, the genomic alteration comprises one or more somatic mutations. In some embodiments, the genomic alteration comprises one or more nonsynonymous mutations. In a particular embodiment, the genomic alteration comprises one or more missense mutations. In other particular embodiments, the genomic alteration comprises one or more alterations selected from the group consisting of a base pair substitution, a base pair insertion, a base pair deletion, a copy number alteration (CNA), a gene rearrangement, and any combination thereof.

In particular embodiments, the TMB status is determined by genome sequencing, exome sequencing, and/or genomic profiling. In one embodiment, the genomic profile comprises at least 300 genes, at least 305 genes, at least 310 genes, at least 315 genes, at least 320 genes, at least 325 genes, at least 330 genes, at least 335 genes, at least 340 genes, at least 345 genes, at least 350 genes, at least 355 genes, at least 360 genes, at least 365 genes, at least 370 genes, at least 375 genes, at least 380 genes, at least 385 genes, at least 390 genes, at least 395 genes, or at least 400 genes. In a particular embodiment, the genomic profile comprises at least 325 genes.

In one embodiment, the genomic profile comprises one or more genes selected from the group consisting of ABL1, BRAF, CHEK1, FANCC, GATA3, JAK2, MITF, PDCD1LG2, RBM10, STAT4, ABL2, BRCA1, CHEK2, FANCD2, GATA4, JAK3, MLH1, PDGFRA, RET, STK11, ACVR1B, BRCA2, CIC, FANCE, GATA6, JUN, MPL, PDGFRB, RICTOR, SUFU, AKT1, BRD4, CREBBP, FANCF, GID4 (C17orf39), KAT6A (MYST3), MRE11A, PDK1, RNF43, SYK, AKT2, BRIP1, CRKL, FANCG, GLI1, KDM5A, MSH2, PIK3C2B, ROS1, TAF1, AKT3, BTG1, CRLF2, FANCL, GNA11, KDM5C, MSH6, PIK3CA, RPTOR, TBX3, ALK, BTK, CSF1R, FAS, GNA13, KDM6A, MTOR, PIK3CB, RUNX1, TERC, AMER1 (FAM123B), C11orf30 (EMSY), CTCF, FAT1, GNAQ, KDR, MUTYH, PIK3CG, RUNX1T1, TERT (promoter only), APC, CARD11, CTNNA1, FBXW7, GNAS, KEAP1, MYC, PIK3R1, SDHA, TET2, AR, CBFB, CTNNB1, FGF10, GPR124, KEL, MYCL (MYCL1), PIK3R2, SDHB, TGFBR2, ARAF, CBL, CUL3, FGF14, GRIN2A, KIT, MYCN, PLCG2, SDHC, TNFAIP3, ARFRP1, CCND1, CYLD, FGF19, GRM3, KLHL6, MYD88, PMS2, SDHD, TNFRSF14, ARID1A, CCND2, DAXX, FGF23, GSK3B, KMT2A (MLL), NFL, POLD1, SETD2, TOP1, ARID1B, CCND3, DDR2, FGF3, H3F3A, KMT2C (MLL3), NF2, POLE, SF3B1, TOP2A, ARID2, CCNE1, DICER1, FGF4, HGF, KMT2D (MLL2), NFE2L2, PPP2R1A, SLIT2, TP53, ASXL1, CD274, DNMT3A, FGF6, HNF1A, KRAS, NFKBIA, PRDM1, SMAD2, TSC1, ATM, CD79A, DOT1L, FGFR1, HRAS, LMO1, NKX2-1, PREX2, SMAD3, TSC2, ATR, CD79B, EGFR, FGFR2, HSD3B1, LRP1B, NOTCH1, PRKAR1A, SMAD4, TSHR, ATRX, CDC73, EP300, FGFR3, HSP90AA1, LYN, NOTCH2, PRKCI, SMARCA4, U2AFL. AURKA, CDH1, EPHA3, FGFR4, IDH1, LZTR1, NOTCH3, PRKDC, SMARCB1, VEGFA, AURKB, CDK12, EPHA5, FH, IDH2, MAGI2, NPM1, PRSS8, SMO, VHL, AXIN1, CDK4, EPHA7, FLCN, IGF1R, MAP2K1, NRAS, PTCH1, SNCAIP, WISP3, AXL, CDK6, EPHB1, FLT1, IGF2, MAP2K2, NSD1, PTEN, SOCS1, WT1, BAP1, CDK8, ERBB2, FLT3, IKBKE, MAP2K4, NTRK1, PTPN11, SOX10, XPO1, BARD1, CDKN1A, ERBB3, FLT4, IKZF1, MAP3K1, NTRK2, QKI, SOX2, ZBTB2, BCL2, CDKN1B, ERBB4, FOXL2, IL7R, MCL1, NTRK3, RAC1, SOX9, ZNF217, BCL2L1, CDKN2A, ERG, FOXP1, INHBA, MDM2, NUP93, RAD50, SPEN, ZNF703, BCL2L2, CDKN2B, ERRFI1, FRS2, INPP4B, MDM4, PAK3, RAD51, SPOP, BCL6, CDKN2C, ESR1, FUBP1, IRF2, MED12, PALB2, RAF1, SPTA1, BCOR, CEBPA, EZH2, GABRA6, IRF4, MEF2B, PARK2, RANBP2, SRC, BCORL1, CHD2, FAM46C, GATA1, IRS2, MEN1, PAX5, RARA, STAG2, BLM, CHD4, FANCA, GATA2, JAK1, MET, PBRM1, RB1, STAT3, and any combination thereof.

In some embodiments, the methods further comprise identifying a genomic alteration in one or more of ETV4, TMPRSS2, ETV5, BCR, ETV1, ETV6, and MYB.

In some embodiments, the high TMB has a score of at least 210, at least 215, at least 220, at least 225, at least 230, at least 235, at least 240, at least 245, at least 250, at least 255, at least 260, at least 265, at least 270, at least 275, at least 280, at least 285, at least 290, at least 295, at least 300, at least 305, at least 310, at least 315, at least 320, at least 325, at least 330, at least 335, at least 340, at least 345, at least 350, at least 355, at least 360, at least 365, at least 370, at least 375, at least 380, at least 385, at least 390, at least 395, at least 400, at least 405, at least 410, at least 415, at least 420, at least 425, at least 430, at least 435, at least 440, at least 445, at least 450, at least 455, at least 460, at least 465, at least 470, at least 475, at least 480, at least 485, at least 490, at least 495, or at least 500. In other embodiments, the high TMB has a score of at least 215, at least 220, at least 221, at least 222, at least 223, at least 224, at least 225, at least 226, at least 227, at least 228, at least 229, at least 230, at least 231, at least 232, at least 233, at least 234, at least 235, at least 236, at least 237, at least 238, at least 239, at least 240, at least 241, at least 242, at least 243, at least 244, at least 245, at least 246, at least 247, at least 248, at least 249, or at least 250. In a particular embodiment, the high TMB has a score of at least 243.

In some embodiments, the methods further comprise comparing the subject's TMB status to a reference TMB value. In one embodiment, the subject's TMB status is within the highest fractile of the reference TMB value. In another embodiment, the subject's TMB status is within the top tertile of the reference TMB value.

In some embodiments, the biological sample is a tumor tissue biopsy, e.g., a formalin-fixed, paraffin-embedded tumor tissue or a fresh-frozen tumor tissue. In other embodiments, the biological sample is a liquid biopsy. In some embodiments, the biological sample comprises one or more of blood, serum, plasma, exoRNA, circulating tumor cells, ctDNA, and cfDNA.

In some embodiments, the subject has a tumor with a high neoantigen load. In other embodiments, the subject has an increased T-cell repertoire.

In some embodiments, the SCLC comprises a small cell carcinoma. In some embodiments, the SCLC comprises a combined small cell carcinoma. In some embodiments, the SCLC is a recurrent SCLC.

In some embodiments, the subject received at least one, at least two, at least three, at least four, or at least five previous lines of therapy to treat the tumor. In some embodiments, the previous line of therapy comprises a chemotherapy. In some embodiments, the chemotherapy comprises a platinum-based therapy. In some embodiments, the platinum-based therapy comprises a platinum-based antineoplastic selected from the group consisting of cisplatin, carboplatin, oxaliplatin, nedaplatin, triplatin tetranitrate, phenanthriplatin, picoplatin, satraplatin, and any combination thereof. In certain embodiments, the platinum-based therapy comprises cisplatin.

In some embodiments, the anti-PD-1 antibody cross-competes with nivolumab for binding to human PD-1. In other embodiments, the anti-PD-1 antibody binds to the same epitope as nivolumab. In some embodiments, the anti-PD-1 antibody is a chimeric antibody, a humanized antibody, a human monoclonal antibody, or an antigen-binding portion thereof. In other embodiments, wherein the anti-PD-1 antibody comprises a heavy chain constant region of a human IgG1 isotype or a human IgG4 isotype. In particular embodiments, the anti-PD-1 antibody is nivolumab or pembrolizumab.

In some embodiments, the anti-PD-1 antibody is administered at a dose ranging from 0.1 mg/kg to 10.0 mg/kg body weight once every 2, 3, or 4 weeks. In one embodiment, the anti-PD-1 antibody is administered at a dose of 5 mg/kg or 10 mg/kg body weight once every 3 weeks. In another embodiment, the anti-PD-1 antibody is administered at a dose of 5 mg/kg body weight once every 3 weeks. In yet another embodiment, the anti-PD-1 antibody is administered at a dose of 3 mg/kg body weight once every 2 weeks.

In some embodiments, the anti-PD-1 antibody is administered as a flat dose. In one embodiment, the anti-PD-1 antibody is administered as a flat dose of at least about 200 mg, at least about 220 mg, at least about 240 mg, at least about 260 mg, at least about 280 mg, at least about 300 mg, at least about 320 mg, at least about 340 mg, at least about 360 mg, at least about 380 mg, at least about 400 mg, at least about 420 mg, at least about 440 mg, at least about 460 mg, at least about 480 mg, at least about 500 mg, or at least about 550 mg. In another embodiment, the anti-PD-1 antibody is administered as a flat dose about once every 1, 2, 3, or 4 weeks.

In some embodiments, the anti-CTLA-4 antibody is a chimeric, humanized or human monoclonal antibody or a portion thereof. In some embodiments, the anti-CTLA-4 antibody comprises a heavy chain constant region which is of a human IgG1 isotype. In some embodiments, the anti-CTLA-4 antibody is ipilimumab. In some embodiments, the anti-CTLA-4 antibody is tremelimumab. In some embodiments, the anti-CTLA-4 antibody cross-competes with ipilimumab for binding to human CTLA-4.

In some embodiments, the anti-CTLA-4 antibody is administered at a dose ranging from at least about 0.1 mg/kg to at least about 10.0 mg/kg body weight once about every 1, 2, 3, or 4 weeks. In some embodiments, the anti-CTLA-4 antibody is administered at a dose of about 1 mg/kg or about 3 mg/kg body weight. In some embodiments, the anti-CTLA-4 antibody is administered at a flat dose. In some embodiments, the anti-CTLA-4 antibody is administered once about every 2 weeks. In some embodiments, wherein the anti-CTLA-4 antibody is administered once about every 3 weeks.

In some embodiments, the anti-PD-1 antibody is administered at a dose of about 3 mg/kg body weight once about every 3 weeks and the anti-CTLA-4 antibody is administered at a dose of about 1 mg/kg body weight once about every 3 weeks. In some embodiments, the anti-PD-1 antibody is administered at a dose of about 1 mg/kg body weight once about every 3 weeks and the anti-CTLA-4 antibody is administered at a dose of about 3 mg/kg body weight once about every 3 weeks.

In some embodiments, (i) the anti-PD-1 antibody is administered at a dose of about 1 mg/kg body weight once about every 3 weeks and the anti-CTLA-4 antibody is administered at a dose of about 3 mg/kg body weight once about every 3 weeks for 4 cycles then (ii) the anti-PD-1 antibody is administered at a dose of about 3 mg/kg body weight once about every two weeks.

In some embodiments, the subject exhibits progression-free survival of at least about one month, at least about 2 months, at least about 3 months, at least about 4 months, at least about 5 months, at least about 6 months, at least about 7 months, at least about 8 months, at least about 9 months, at least about 10 months, at least about 11 months, at least about one year, at least about eighteen months, at least about two years, at least about three years, at least about four years, or at least about five years after the administration.

In other embodiments, the subject exhibits an overall survival of at least about one month, at least about 2 months, at least about 3 months, at least about 4 months, at least about 5 months, at least about 6 months, at least about 7 months, at least about 8 months, at least about 9 months, at least about 10 months, at least about 11 months, at least about one year, at least about eighteen months, at least about two years, at least about three years, at least about four years, or at least about five years after the administration.

In yet other embodiments, the subject exhibits an objective response rate of at least about 30%, about 35%, about 40%, about 45%, about 50%, about 55%, about 60%, about 65%, about 70%, about 75%, about 80%, about 85%, about 90%, about 95%, or about 100%.

Other features and advantages of the instant disclosure will be apparent from the following detailed description and examples which should not be construed as limiting. The contents of all cited references, including scientific articles, newspaper reports, GenBank entries, patents and patent applications cited throughout this application are expressly incorporated herein by reference.

EMBODIMENTS

E1. A method for treating a subject afflicted with a tumor derived from a small cell lung cancer (SCLC) comprising administering to the subject a therapeutically effective amount of an antibody or antigen-binding portion thereof that specifically binds to a Programmed Death-1 (PD-1) receptor and inhibits PD-1 activity ("an anti-PD-1 antibody"), wherein the tumor has a tumor mutational burden (TMB) status that is a high TMB.

E2. A method for treating a subject afflicted with a tumor derived from an SCLC comprising administering to the subject a therapeutically effective amount of an anti-PD-1 antibody and an antibody or antigen-binding portion thereof that specifically binds to CTLA-4 ("an anti-CTLA-4 antibody"), wherein the tumor has a TMB status that is a high TMB E3. The method of E1 or E2, further comprising measuring the TMB status of a biological sample obtained from the subject.

E4. A method of identifying a subject who is afflicted with a tumor derived from an SCLC and suitable for a therapy of an anti-PD-1 antibody comprising measuring a TMB status of a biological sample of the subject, wherein the TMB status is a high TMB.

E5. A method of identifying a subject who is afflicted with a tumor derived from an SCLC and suitable for a combination therapy comprising an anti-PD-1 antibody and an anti-CTLA-4 antibody comprising measuring a TMB status of a biological sample of the subject, wherein the TMB status is a high TMB.

E6. The method of E4, further comprising administering to the subject the anti-PD-1 antibody.

E7. The method of E5, further comprising administering to the subject the anti-PD-1 antibody and the anti-CTLA-4 antibody.

E8. The method of any one of E1 to E7, wherein the TMB status is determined by sequencing nucleic acids in the tumor and identifying a genomic alteration in the sequenced nucleic acids.

E9. The method of E8, wherein the genomic alteration comprises one or more somatic mutations.

E10. The method of E8 or E9, wherein the genomic alteration comprises one or more nonsynonymous mutations.

E11. The method of any one of E8 to E10, wherein the genomic alteration comprises one or more missense mutations.

E12. The method of any one of E8 to E11, wherein the genomic alteration comprises one or more alterations selected from the group consisting of a base pair substitution, a base pair insertion, a base pair deletion, a copy number alteration (CNAs), a gene rearrangement, and any combination thereof.

E13. The method of any one of E1 to E12, wherein the high TMB has a score of at least 210, at least 215, at least 220, at least 225, at least 230, at least 235, at least 240, at least 245, at least 250, at least 255, at least 260, at least 265, at least 270, at least 275, at least 280, at least 285, at least 290, at least 295, at least 300, at least 305, at least 310, at least 315, at least 320, at least 325, at least 330, at least 335, at least 340, at least 345, at least 350, at least 355, at least 360, at least 365, at least 370, at least 375, at least 380, at least 385, at least 390, at least 395, at least 400, at least 405, at least 410, at least 415, at least 420, at least 425, at least 430, at least 435, at least 440, at least 445, at least 450, at least 455, at least 460, at least 465, at least 470, at least 475, at least 480, at least 485, at least 490, at least 495, or at least 500.

E14. The method of any one of E1 to E12, wherein the high TMB has a score of at least 215, at least 220, at least 221, at least 222, at least 223, at least 224, at least 225, at least 226, at least 227, at least 228, at least 229, at least 230, at least 231, at least 232, at least 233, at least 234, at least 235, at least 236, at least 237, at least 238, at least 239, at least 240, at least 241, at least 242, at least 243, at least 244, at least 245, at least 246, at least 247, at least 248, at least 249, or at least 250.

E15. The method of any one of E1 to E14, wherein the high TMB has a score of at least 243.

E16. The method of any one of E1 to E15, further comprising comparing the subject's TMB status to a reference TMB value.

E17. The method of E16, wherein the subject's TMB status is within the highest fractile of the reference TMB value.

E18. The method of E16, wherein the subject's TMB status is within the top tertile of the reference TMB value.

E19. The method of any one of E1 to E18, wherein the biological sample is a tumor tissue biopsy.

E20. The method of E19, wherein the tumor tissue is a formalin-fixed, paraffin-embedded tumor tissue or a fresh-frozen tumor tissue.

E21. The method of any one of E1 to E18, wherein the biological sample is a liquid biopsy.

E22. The method of any one of E1 to E18, wherein the biological sample comprises one or more of blood, serum, plasma, exoRNA, circulating tumor cells, ctDNA, and cfDNA.

E23. The method of any one of E1 to E22, wherein the TMB status is determined by genome sequencing.

E24. The method of any one of E1 to E22, wherein the TMB status is determined by exome sequencing.

E25. The method of any one of E1 to E22, wherein the TMB status is determined by genomic profiling.

E26. The method of E25, wherein the genomic profile comprises at least 300 genes, at least 305 genes, at least 310 genes, at least 315 genes, at least 320 genes, at least 325 genes, at least 330 genes, at least 335 genes, at least 340 genes, at least 345 genes, at least 350 genes, at least 355 genes, at least 360 genes, at least 365 genes, at least 370 genes, at least 375 genes, at least 380 genes, at least 385 genes, at least 390 genes, at least 395 genes, or at least 400 genes.

E27. The method of E25, wherein the genomic profile comprises at least 325 genes.

E28. The method of any one of E25 to E27, wherein the genomic profile comprises one or more genes selected from the group consisting of ABL1, BRAF, CHEK1, FANCC, GATA3, JAK2, MITF, PDCD1LG2, RBM10, STAT4, ABL2, BRCA1, CHEK2, FANCD2, GATA4, JAK3, MLH1, PDGFRA, RET, STK11, ACVR1B, BRCA2, CIC, FANCE, GATA6, JUN, MPL, PDGFRB, RICTOR, SUFU, AKT1, BRD4, CREBBP, FANCF, GID4 (C17orf39), KAT6A (MYST3), MRE11A, PDK1, RNF43, SYK, AKT2, BRIP1, CRKL, FANCG, GLI1, KDM5A, MSH2, PIK3C2B, ROS1, TAF1, AKT3, BTG1, CRLF2, FANCL, GNA11, KDM5C, MSH6, PIK3CA, RPTOR, TBX3, ALK, BTK, CSF1R, FAS, GNA13, KDM6A, MTOR, PIK3CB, RUNX1, TERC, AMER1 (FAM123B), C11orf30 (EMSY), CTCF, FAT1, GNAQ, KDR, MUTYH, PIK3CG, RUNX1T1, TERT (promoter only), APC, CARD11, CTNNA1, FBXW7, GNAS, KEAP1, MYC, PIK3R1, SDHA, TET2, AR, CBFB, CTNNB1, FGF10, GPR124, KEL, MYCL (MYCL1), PIK3R2, SDHB, TGFBR2, ARAF, CBL, CUL3, FGF14, GRIN2A, KIT, MYCN, PLCG2, SDHC, TNFAIP3, ARFRP1, CCND1, CYLD, FGF19, GRM3, KLHL6, MYD88, PMS2, SDHD, TNFRSF14, ARID1A, CCND2, DAXX, FGF23, GSK3B, KMT2A (MLL), NF1, POLD1, SETD2, TOP1, ARID1B, CCND3, DDR2, FGF3, H3F3A, KMT2C (MLL3), NF2, POLE, SF3B1, TOP2A, ARID2, CCNE1, DICER1, FGF4, HGF, KMT2D (MLL2), NFE2L2, PPP2R1A, SLIT2, TP53, ASXL1, CD274, DNMT3A, FGF6, HNF1A, KRAS, NFKBIA, PRDM1, SMAD2, TSC1, ATM, CD79A, DOT1L, FGFR1, HRAS, LMO1, NKX2-1, PREX2, SMAD3, TSC2, ATR, CD79B, EGFR, FGFR2, HSD3B1, LRP1B, NOTCH1, PRKAR1A, SMAD4, TSHR, ATRX, CDC73, EP300, FGFR3, HSP90AA1, LYN, NOTCH2, PRKCI, SMARCA4, U2AF1, AURKA, CDH1, EPHA3, FGFR4, IDH1, LZTR1, NOTCH3, PRKDC, SMARCB1, VEGFA, AURKB, CDK12, EPHA5, FH, IDH2, MAGI2, NPM1, PRSS8, SMO, VHL, AXIN1, CDK4, EPHA7, FLCN, IGF1R, MAP2K1, NRAS, PTCH1, SNCAIP, WISP3, AXL, CDK6, EPHB1, FLT1, IGF2, MAP2K2, NSD1, PTEN, SOCS1, WT1, BAP1, CDK8, ERBB2, FLT3, IKBKE, MAP2K4, NTRK1, PTPN11, SOX10, XPO1, BARD1, CDKN1A, ERBB3, FLT4, IKZF1, MAP3K1, NTRK2, QKI, SOX2, ZBTB2, BCL2, CDKN1B, ERBB4, FOXL2, IL7R, MCL1, NTRK3, RAC1, SOX9, ZNF217, BCL2L1, CDKN2A, ERG, FOXP1, INHBA, MDM2, NUP93, RAD50, SPEN, ZNF703, BCL2L2, CDKN2B, ERRFI1, FRS2, INPP4B, MDM4, PAK3, RAD51, SPOP, BCL6, CDKN2C, ESR1, FUBP1, IRF2, MED12, PALB2, RAF1, SPTA1, BCOR, CEBPA, EZH2, GABRA6, IRF4, MEF2B, PARK2, RANBP2, SRC, BCORL1, CHD2, FAM46C, GATA1, IRS2, MEN1, PAX5, RARA, STAG2, BLM, CHD4, FANCA, GATA2, JAK1, MET, PBRM1, RB1, STAT3, and any combination thereof.

E29. The method of any one of E1 to E28, further comprising identifying a genomic alteration in one or more of ETV4, TMPRSS2, ETV5, BCR, ETV1, ETV6, and MYB.

E30. The method of any one of E1 to E29, wherein the subject has a tumor with a high neoantigen load.

E31. The method of any one of E1 to E30, wherein the subject has an increased T-cell repertoire.

E32. The method of any one of E1 to E31, wherein the SCLC comprises a small cell carcinoma.

E33. The method of any one of E1 to E31, wherein the SCLC comprises a combined small cell carcinoma.

E34. The method of any one of E1 to E33, wherein the SCLC is a recurrent SCLC.

E35. The method of any one of E1 to E34, wherein the subject received at least one, at least two, at least three, at least four, or at least five previous lines of therapy to treat the tumor.

E36. The method E35, wherein the previous line of therapy comprises a chemotherapy.

E37. The method of E36, wherein the chemotherapy comprises a platinum-based therapy.

E38. The method of E37, wherein the platinum-based therapy comprises a platinum-based antineoplastic selected from the group consisting of cisplatin, carboplatin, oxaliplatin, nedaplatin, triplatin tetranitrate, phenanthriplatin, picoplatin, satraplatin, and any combination thereof.

E39. The method of E37 or E38, wherein the platinum-based therapy comprises cisplatin.

E40. The method of any one of E1 to E39, wherein the anti-PD-1 antibody cross-competes with nivolumab for binding to human PD-1.

E41. The method of any one of E1 to E40, wherein the anti-PD-1 antibody binds to the same epitope as nivolumab.

E42. The method of any one of E1 to E41, wherein the anti-PD-1 antibody is a chimeric antibody, a humanized antibody, a human monoclonal antibody, or an antigen-binding portion thereof.

E43. The method of any one of E1 to E42, wherein the anti-PD-1 antibody comprises a heavy chain constant region of a human IgG1 isotype or a human IgG4 isotype.

E44. The method of any one of E1 to E43, wherein the anti-PD-1 antibody is nivolumab.

E45. The method of any one of E1 to E43, wherein the anti-PD-1 antibody is pembrolizumab.

E46. The method of any one of E1 to E45, wherein the anti-PD-1 antibody is administered at a dose ranging from 0.1 mg/kg to E10.0 mg/kg body weight once every 2, 3, or 4 weeks.

E47. The method of any one of E1 to E46, wherein the anti-PD-1 antibody is administered at a dose of 5 mg/kg or E10 mg/kg body weight once every 3 weeks.

E48. The method of any one of E1 to E47, wherein the anti-PD-1 antibody is administered at a dose of 5 mg/kg body weight once every 3 weeks.

E49. The method of any one of E1 to E46, wherein the anti-PD-1 antibody is administered at a dose of 3 mg/kg body weight once every 2 weeks.

E50. The method of any one of E1 to E45, wherein the anti-PD-1 antibody is administered as a flat dose.

E51. The method of E50, wherein the anti-PD-1 antibody is administered as a flat dose of at least about 200 mg, at least about 220 mg, at least about 240 mg, at least about 260 mg, at least about 280 mg, at least about 300 mg, at least about 320 mg, at least about 340 mg, at least about 360 mg, at least about 380 mg, at least about 400 mg, at least about 420 mg, at least about 440 mg, at least about 460 mg, at least about 480 mg, at least about 500 mg, or at least about 550 mg.

E52. The method of E50 or E51, wherein the anti-PD-1 antibody is administered as a flat dose about once every 1, 2, 3, or 4 weeks.

E53 The method of any one of E2, E3, E5, and E6 to E52, wherein the anti-CTLA-4 antibody is a chimeric, humanized or human monoclonal antibody or a portion thereof.

E54. The method of any one of E2, E3, E5, and E6 to E53, wherein the anti-CTLA-4 antibody comprises a heavy chain constant region which is of a human IgG1 isotype.

E55. The method of any one of E2, E3, E5, and E6 to E55, wherein the anti-CTLA-4 antibody is ipilimumab.

E56. The method of any one of E2, E3, E5, and E6 to E55, wherein the anti-CTLA-4 antibody is tremelimumab.

E57. The method of any one of E2, E3, E5, and E6 to E56, wherein the anti-CTLA-4 antibody cross-competes with ipilimumab for binding to human CTLA-4.

E58. The method of any one of E2, E3, E5, and E6 to E57, wherein the anti-CTLA-4 antibody is administered at a dose ranging from at least about 0.1 mg/kg to at least about 10.0 mg/kg body weight once about every 1, 2, 3, or 4 weeks.

E59. The method of any one of E2, E3, E5, and E6 to E57, wherein the anti-CTLA-4 antibody is administered at a dose of about 1 mg/kg or about 3 mg/kg body weight.

E60 The method of any one of E2, E3, E5, and E6 to E57, wherein the anti-CTLA-4 antibody is administered at a flat dose.

E61. The method of any one of E2, E3, E5, and E6 to E60, wherein the anti-CTLA-4 antibody is administered once about every 2 weeks.

E62. The method of any one of E2, E3, E5, and E6 to E60, wherein the anti-CTLA-4 antibody is administered once about every 3 weeks.

E63. The method of any one of E2, E3, E5, and E6 to E57, wherein the anti-PD-1 antibody is administered at a dose of about 3 mg/kg body weight once about every 3 weeks and the anti-CTLA-4 antibody is administered at a dose of about 1 mg/kg body weight once about every 3 weeks.

E64. The method of any one of E2, E3, E5, and E6 to E57, wherein the anti-PD-1 antibody is administered at a dose of about 1 mg/kg body weight once about every 3 weeks and the anti-CTLA-4 antibody is administered at a dose of about 3 mg/kg body weight once about every 3 weeks.

E65. The method of any one of E2, E3, E5, and E6 to E57, wherein (i) the anti-PD-1 antibody is administered at a dose of about 1 mg/kg body weight once about every 3 weeks and the anti-CTLA-4 antibody is administered at a dose of about 3 mg/kg body weight once about every 3 weeks for 4 cycles then (ii) the anti-PD-1 antibody is administered at a dose of about 3 mg/kg body weight once about every two weeks.

E66. The method of any one of E1 to E65, wherein the subject exhibits progression-free survival of at least about one month, at least about 2 months, at least about 3 months, at least about 4 months, at least about 5 months, at least about 6 months, at least about 7 months, at least about 8 months, at least about 9 months, at least about 10 months, at least about 11 months, at least about one year, at least about eighteen months, at least about two years, at least about three years, at least about four years, or at least about five years after the administration.

E67. The method of any one of E1 to E66, wherein the subject exhibits an overall survival of at least about one month, at least about 2 months, at least about 3 months, at least about 4 months, at least about 5 months, at least about 6 months, at least about 7 months, at least about 8 months, at least about 9 months, at least about 10 months, at least about 11 months, at least about one year, at least about 14 months, at least about 16 months, at least about 18 months, at least about 20 months, at least about 22 months, at least about two years, at least about three years, at least about four years, or at least about five years after the administration.

E68. The method of any one of E1 to E67, wherein the subject exhibits an objective response rate of at least about 15%, at least about 20%, at least about 25%, at least about 30%, about 35%, about 40%, about 45%, about 50%, about 55%, about 60%, about 65%, about 70%, about 75%, about 80%, about 85%, about 90%, about 95%, or about 100%.

E69. The method of E25, wherein the genomic profile comprises FOUNDATIONONE® CDX™.

E70. The method of any one of E1 to E69, wherein the tumor has a TMB of at least about 10 mutations per megabase of genome sequenced.

BRIEF DESCRIPTION OF THE DRAWINGS

FIGS. 3A-3D are graphical representations of progression free survival (PFS; FIGS. 3A and 3C) and overall survival (OS; FIGS. 3B and 3D) for subjects treated with an anti-PD-1 antibody, e.g., nivolumab, monotherapy (FIGS. 3A and 3B) or a combination therapy comprising an anti-PD-1 antibody, e.g., nivolumab and an anti-CTLA-4 antibody, e.g., ipilimumab (FIGS. 3C and 3D). PFS and OS for ITT patients and TMB-evaluable patients are overlaid as indicated (FIGS. 3A-3D).

FIGS. 4A-4C are graphical representations of the TMB distribution for subjects in the SCLC clinical trial, described herein (FIG. 4A), the pooled SCLC study subjects (FIG. 4B) and the pooled subjects from a previous clinical trial directed to the treatment of non-small cell lung cancer (FIG. 4C).

FIGS. 7A-7B show the progression free survival (PFS) in subjects treated with a an anti-PD-1 antibody, e.g., nivolumab, monotherapy (FIG. 7A) or a combination therapy comprising an anti-PD-1 antibody, e.g., nivolumab, and an anti-CTLA-4 antibody, e.g., ipilimumab (FIG. 7B) stratified by TMB status (low, medium, or high), as indicated. One-year PFS is marked for each sample population.

FIGS. 8A-8B show the overall survival (OS) for subjects treated with an anti-PD-1 antibody, e.g., nivolumab monotherapy (FIG. 8A) or a combination therapy comprising an anti-PD-1 antibody, e.g., nivolumab, and an anti-CTLA-4 antibody, e.g., ipilimumab (FIG. 8B) stratified by TMB status (low, medium, or high), as indicated. One-year OS is marked for each sample population.

DETAILED DESCRIPTION OF THE DISCLOSURE

Figure 1:
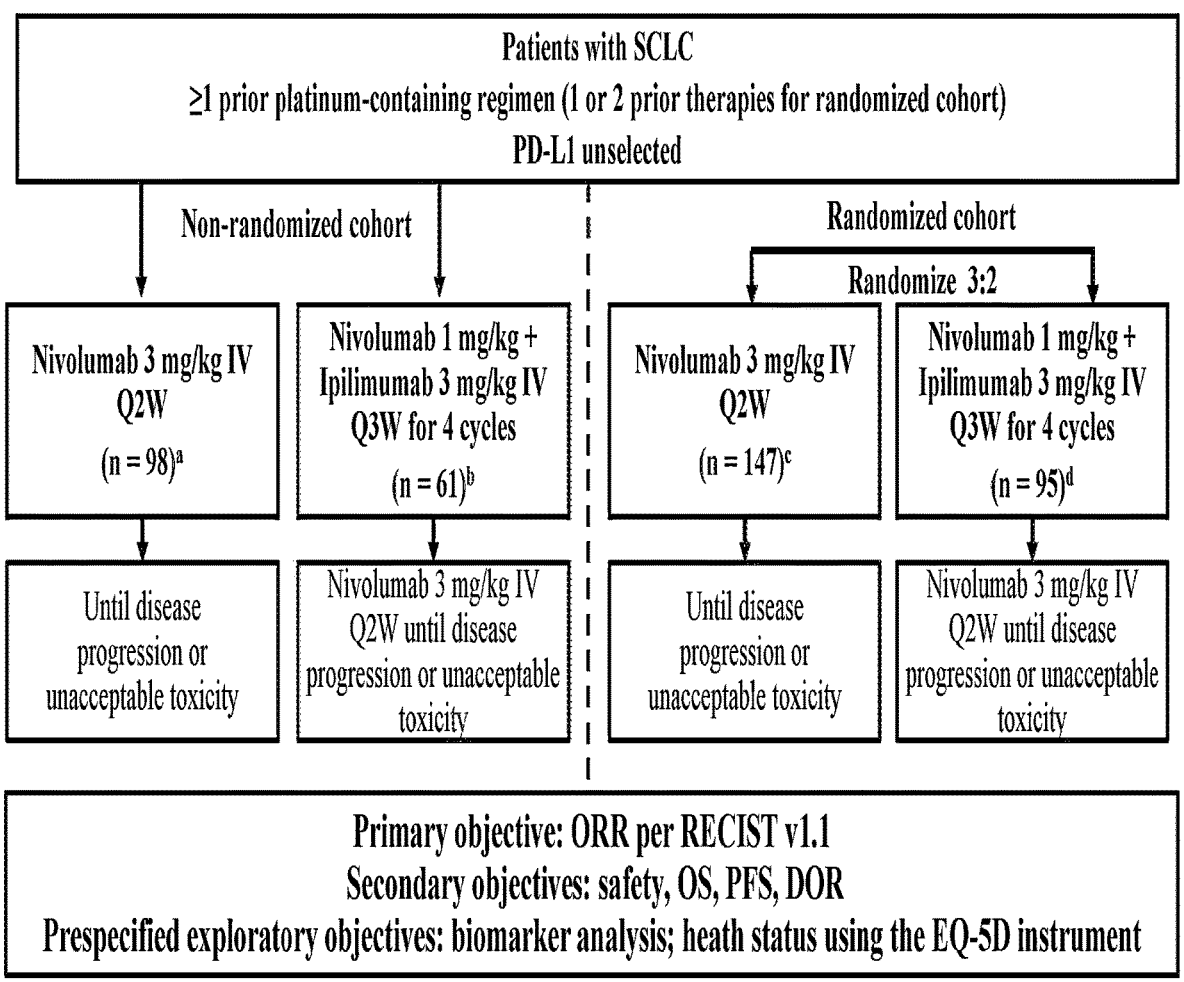
FIG. 1 is a schematic representation of a clinical trial protocol directed to the treatment of SCLC using an anti-PD-1 antibody, e.g., nivolumab, monotherapy or a combination therapy comprising an anti-PD-1 antibody, e.g., nivolumab, and an anti-CTLA-4 antibody, e.g., ipilimumab. The database was locked on Mar. 30, 2017. Patients (ITT, N=401; based on data from the previous database lock, and only patients in the 1 mg/kg nivolumab+3 mg/kg ipilimumab and 3 mg/kg nivolumab monotherapy cohorts were selected for further development in SCLC) received either nivolumab monotherapy (n=245) or nivolumab+ipilimumab (n=156). DOR=duration of response; EQ-5D=EuroQoL-5 Dimensions; ORR=objective response rate; OS overall survival; PD-L1=programmed death ligand 1; PFS=progression-free survival. $^a$Median follow-up 23.3 months; $^b$Median follow-up 28.6 months; $^c$Median follow-up 10.8 months; $^d$Median follow-up 11.2 months.

The present disclosure relates to methods for treating a small cell lung cancer patient with a tumor having a high TMB status comprising administering to the patient an anti-PD-1 antibody monotherapy or a combination therapy comprising an anti-PD-1 antibody and an anti-CTLA-4 antibody. The present disclosure also relates to a method for identifying a small cell lung cancer patient suitable for treatment with an anti-PD-1 antibody monotherapy or a combination therapy comprising an anti-PD-1 antibody and an anti-CTLA-4 antibody comprising measuring a TMB status of a biological sample of the patient.

Terms

In order that the present disclosure can be more readily understood, certain terms are first defined. As used in this application, except as otherwise expressly provided herein, each of the following terms shall have the meaning set forth below. Additional definitions are set forth throughout the application.

"Administering" refers to the physical introduction of a composition comprising a therapeutic agent to a subject, using any of the various methods and delivery systems known to those skilled in the art. Preferred routes of administration for the anti-PD-1 antibody include intravenous, intramuscular, subcutaneous, intraperitoneal, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intralymphatic, intralesional, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion, as well as in vivo electroporation. The TKI is typically administered via a non-parenteral route, preferably orally. Other non-parenteral routes include a topical, epidermal or mucosal route of administration, for example, intranasally, vaginally, rectally, sublingually or topically. Administering can also be performed, for example, once, a plurality of times, and/or over one or more extended periods.

An "adverse event" (AE) as used herein is any unfavorable and generally unintended or undesirable sign (including an abnormal laboratory finding), symptom, or disease associated with the use of a medical treatment. For example, an adverse event can be associated with activation of the immune system or expansion of immune system cells (e.g., T cells) in response to a treatment. A medical treatment can have one or more associated AEs and each AE can have the same or different level of severity. Reference to methods capable of "altering adverse events" means a treatment regime that decreases the incidence and/or severity of one or more AEs associated with the use of a different treatment regime.

An "antibody" (Ab) shall include, without limitation, a glycoprotein immunoglobulin which binds specifically to an antigen and comprises at least two heavy (H) chains and two light (L) chains interconnected by disulfide bonds, or an antigen-binding portion thereof. Each H chain comprises a heavy chain variable region (abbreviated herein as $V_H$) and a heavy chain constant region. The heavy chain constant region comprises three constant domains, $C_{H1}$, $C_{H2}$ and $C_{H3}$. Each light chain comprises a light chain variable region (abbreviated herein as $V_L$) and a light chain constant region. The light chain constant region is comprises one constant domain, $C_L$. The $V_H$ and $V_L$ regions can be further subdivided into regions of hypervariability, termed complementarity determining regions (CDRs), interspersed with regions that are more conserved, termed framework regions (FRs). Each $V_H$ and $V_L$ comprises three CDRs and four FRs, arranged from amino-terminus to carboxy-terminus in the following order: FR1, CDR1, FR2, CDR2, FR3, CDR3, and FR4. The variable regions of the heavy and light chains contain a binding domain that interacts with an antigen. The constant regions of the antibodies can mediate the binding of the immunoglobulin to host tissues or factors, including various cells of the immune system (e.g., effector cells) and the first component (C1q) of the classical complement system.

An immunoglobulin can derive from any of the commonly known isotypes, including but not limited to IgA, secretory IgA, IgG and IgM. IgG subclasses are also well known to those in the art and include but are not limited to human IgG1, IgG2, IgG3 and IgG4. "Isotype" refers to the antibody class or subclass (e.g., IgM or IgG1) that is encoded by the heavy chain constant region genes. The term "antibody" includes, by way of example, both naturally occurring and non-naturally occurring antibodies; monoclonal and polyclonal antibodies; chimeric and humanized antibodies; human or nonhuman antibodies; wholly synthetic antibodies; and single chain antibodies. A nonhuman antibody can be humanized by recombinant methods to reduce its immunogenicity in man. Where not expressly stated, and unless the context indicates otherwise, the term "antibody" also includes an antigen-binding fragment or an antigen-binding portion of any of the aforementioned immunoglobulins, and includes a monovalent and a divalent fragment or portion, and a single chain antibody.

An "isolated antibody" refers to an antibody that is substantially free of other antibodies having different antigenic specificities (e.g., an isolated antibody that binds specifically to PD-1 is substantially free of antibodies that bind specifically to antigens other than PD-1). An isolated antibody that binds specifically to PD-1 may, however, have cross-reactivity to other antigens, such as PD-1 molecules from different species. Moreover, an isolated antibody can be substantially free of other cellular material and/or chemicals.

The term "monoclonal antibody" (mAb) refers to a non-naturally occurring preparation of antibody molecules of single molecular composition, i.e., antibody molecules whose primary sequences are essentially identical, and which exhibits a single binding specificity and affinity for a particular epitope. A monoclonal antibody is an example of an isolated antibody. Monoclonal antibodies can be produced by hybridoma, recombinant, transgenic or other techniques known to those skilled in the art.

A "human antibody" (HuMAb) refers to an antibody having variable regions in which both the framework and CDR regions are derived from human germline immunoglobulin sequences. Furthermore, if the antibody contains a constant region, the constant region also is derived from human germline immunoglobulin sequences. The human antibodies of the disclosure can include amino acid residues not encoded by human germline immunoglobulin sequences (e.g., mutations introduced by random or site-specific mutagenesis in vitro or by somatic mutation in vivo). However, the term "human antibody," as used herein, is not intended to include antibodies in which CDR sequences derived from the germline of another mammalian species, such as a mouse, have been grafted onto human framework sequences. The terms "human antibody" and "fully human antibody" and are used synonymously.

A "humanized antibody" refers to an antibody in which some, most or all of the amino acids outside the CDRs of a non-human antibody are replaced with corresponding amino acids derived from human immunoglobulins. In one embodiment of a humanized form of an antibody, some, most or all of the amino acids outside the CDRs have been replaced with amino acids from human immunoglobulins, whereas some, most or all amino acids within one or more CDRs are unchanged. Small additions, deletions, insertions, substitutions or modifications of amino acids are permissible as long as they do not abrogate the ability of the antibody to bind to a particular antigen. A "humanized antibody" retains an antigenic specificity similar to that of the original antibody.

A "chimeric antibody" refers to an antibody in which the variable regions are derived from one species and the constant regions are derived from another species, such as an antibody in which the variable regions are derived from a mouse antibody and the constant regions are derived from a human antibody.

An "anti-antigen antibody" refers to an antibody that binds specifically to the antigen. For example, an anti-PD-1 antibody binds specifically to PD-1.

An "antigen-binding portion" of an antibody (also called an "antigen-binding fragment") refers to one or more fragments of an antibody that retain the ability to bind specifically to the antigen bound by the whole antibody.

A "cancer" refers a broad group of various diseases characterized by the uncontrolled growth of abnormal cells in the body. Unregulated cell division and growth divide and grow results in the formation of malignant tumors that invade neighboring tissues and can also metastasize to distant parts of the body through the lymphatic system or bloodstream.

The term "immunotherapy" refers to the treatment of a subject afflicted with, or at risk of contracting or suffering a recurrence of, a disease by a method comprising inducing, enhancing, suppressing or otherwise modifying an immune response. "Treatment" or "therapy" of a subject refers to any type of intervention or process performed on, or the administration of an active agent to, the subject with the objective of reversing, alleviating, ameliorating, inhibiting, slowing down or preventing the onset, progression, development, severity or recurrence of a symptom, complication or condition, or biochemical indicia associated with a disease.

"Programmed Death-1" (PD-1) refers to an immunoinhibitory receptor belonging to the CD28 family. PD-1 is expressed predominantly on previously activated T cells in vivo, and binds to two ligands, PD-L1 and PD-L2. The term "PD-1" as used herein includes human PD-1 (hPD-1), variants, isoforms, and species homologs of hPD-1, and analogs having at least one common epitope with hPD-1. The complete hPD-1 sequence can be found under GenBank Accession No. U64863.

"Programmed Death Ligand-1" (PD-L1) is one of two cell surface glycoprotein ligands for PD-1 (the other being PD-L2) that downregulate T cell activation and cytokine secretion upon binding to PD-1. The term "PD-L1" as used herein includes human PD-L1 (hPD-L1), variants, isoforms, and species homologs of hPD-L1, and analogs having at least one common epitope with hPD-L1. The complete hPD-L1 sequence can be found under GenBank Accession No. Q9NZQ7.

A "subject" includes any human or nonhuman animal. The term "nonhuman animal" includes, but is not limited to, vertebrates such as nonhuman primates, sheep, dogs, and rodents such as mice, rats and guinea pigs. In preferred embodiments, the subject is a human. The terms, "subject" and "patient" are used interchangeably herein.

The use of the term "flat dose" with regard to the methods and dosages of the disclosure means a dose that is administered to a patient without regard for the weight or body surface area (BSA) of the patient. The flat dose is therefore not provided as a mg/kg dose, but rather as an absolute amount of the agent (e.g., the anti-PD-1 antibody). For example, a 60 kg person and a 100 kg person would receive the same dose of an antibody (e.g., 240 mg of an anti-PD-1 antibody). In some embodiments, an anti-PD-1 antibody is administered in a method described herein at a flat dose of about 240 mg once every two weeks. In some embodiments, an anti-PD-1 antibody is administered in a method described herein at a flat dose of about 480 mg once every four weeks. In other embodiments, an anti-PD-1 antibody is administered in a method described herein at a flat dose of about 200 mg once every three weeks.

The use of the term "fixed dose" with regard to a method of the disclosure means that two or more different antibodies in a single composition (e.g., anti-PD-1 antibody and anti-CTLA-4 antibody) are present in the composition in particular (fixed) ratios with each other. In some embodiments, the fixed dose is based on the weight (e.g., mg) of the antibodies. In certain embodiments, the fixed dose is based on the concentration (e.g., mg/ml) of the antibodies. In some embodiments, the ratio is at least about 1:1, about 1:2, about 1:3, about 1:4, about 1:5, about 1:6, about 1:7, about 1:8, about 1:9, about 1:10, about 1:15, about 1:20, about 1:30, about 1:40, about 1:50, about 1:60, about 1:70, about 1:80, about 1:90, about 1:100, about 1:120, about 1:140, about 1:160, about 1:180, about 1:200, about 200:1, about 180:1, about 160:1, about 140:1, about 120:1, about 100:1, about 90:1, about 80:1, about 70:1, about 60:1, about 50:1, about 40:1, about 30:1, about 20:1, about 15:1, about 10:1, about 9:1, about 8:1, about 7:1, about 6:1, about 5:1, about 4:1, about 3:1, or about 2:1 mg first antibody (e.g., anti-PD-1 antibody) to mg second antibody (e.g., anti-CTLA-4 antibody). For example, the 3:1 ratio of an anti-PD-1 antibody and an anti-CTLA-4 antibody can mean that a vial can contain about 240 mg of the anti-PD-1 antibody and 80 mg of the anti-CTLA-4 antibody or about 3 mg/ml of the anti-PD-1 antibody and 1 mg/ml of the anti-CTLA-4 antibody.

The term "weight-based dose" as referred to herein means that a dose that is administered to a patient is calculated based on the weight of the patient. For example, when a patient with 60 kg body weight requires 3 mg/kg of an anti-PD-1 antibody, one can calculate and use the appropriate amount of the anti-PD-1 antibody (i.e., 180 mg) for administration.

A "therapeutically effective amount" or "therapeutically effective dosage" of a drug or therapeutic agent is any amount of the drug that, when used alone or in combination with another therapeutic agent, protects a subject against the onset of a disease or promotes disease regression evidenced by a decrease in severity of disease symptoms, an increase in frequency and duration of disease symptom-free periods, or a prevention of impairment or disability due to the disease affliction. The ability of a therapeutic agent to promote disease regression can be evaluated using a variety of methods known to the skilled practitioner, such as in human subjects during clinical trials, in animal model systems predictive of efficacy in humans, or by assaying the activity of the agent in in vitro assays.

By way of example, an "anti-cancer agent" promotes cancer regression in a subject. In preferred embodiments, a therapeutically effective amount of the drug promotes cancer regression to the point of eliminating the cancer. "Promoting cancer regression" means that administering an effective amount of the drug, alone or in combination with an anti-neoplastic agent, results in a reduction in tumor growth or size, necrosis of the tumor, a decrease in severity of at least one disease symptom, an increase in frequency and duration of disease symptom-free periods, or a prevention of impairment or disability due to the disease affliction. In addition, the terms "effective" and "effectiveness" with regard to a treatment includes both pharmacological effectiveness and physiological safety. Pharmacological effectiveness refers to the ability of the drug to promote cancer regression in the patient. Physiological safety refers to the level of toxicity, or other adverse physiological effects at the cellular, organ and/or organism level (adverse effects) resulting from administration of the drug.

By way of example for the treatment of tumors, a therapeutically effective amount of an anti-cancer agent preferably inhibits cell growth or tumor growth by at least about 20%, more preferably by at least about 40%, even more preferably by at least about 60%, and still more preferably by at least about 80% relative to untreated subjects. In other preferred embodiments of the disclosure, tumor regression can be observed and continue for a period of at least about 20 days, more preferably at least about 40 days, or even more preferably at least about 60 days. Notwithstanding these ultimate measurements of therapeutic effectiveness, evaluation of immunotherapeutic drugs must also make allowance for immune-related response patterns.

An "immune response" is as understood in the art, and generally refers to a biological response within a vertebrate against foreign agents or abnormal, e.g., cancerous cells, which response protects the organism against these agents and diseases caused by them. An immune response is mediated by the action of one or more cells of the immune system (for example, a T lymphocyte, B lymphocyte, natural killer (NK) cell, macrophage, eosinophil, mast cell, dendritic cell or neutrophil) and soluble macromolecules produced by any of these cells or the liver (including antibodies, cytokines, and complement) that results in selective targeting, binding to, damage to, destruction of, and/or elimination from the vertebrate's body of invading pathogens, cells or tissues infected with pathogens, cancerous or other abnormal cells, or, in cases of autoimmunity or pathological inflammation, normal human cells or tissues. An immune reaction includes, e.g., activation or inhibition of a T cell, e.g., an effector T cell, a Th cell, a $CD4^+$ cell, a $CD8^+$ T cell, or a Treg cell, or activation or inhibition of any other cell of the immune system, e.g., NK cell.

An "immune-related response pattern" refers to a clinical response pattern often observed in cancer patients treated with immunotherapeutic agents that produce antitumor effects by inducing cancer-specific immune responses or by modifying native immune processes. This response pattern is characterized by a beneficial therapeutic effect that follows an initial increase in tumor burden or the appearance of new lesions, which in the evaluation of traditional chemotherapeutic agents would be classified as disease progression and would be synonymous with drug failure. Accordingly, proper evaluation of immunotherapeutic agents can require long-term monitoring of the effects of these agents on the target disease.

An "immunomodulator" or "immunoregulator" refers to an agent, e.g., an agent targeting a component of a signaling pathway that can be involved in modulating, regulating, or modifying an immune response. "Modulating," "regulating," or "modifying" an immune response refers to any alteration in a cell of the immune system or in the activity of such cell (e.g., an effector T cell, such as a Th1 cell). Such modulation includes stimulation or suppression of the immune system which can be manifested by an increase or decrease in the number of various cell types, an increase or decrease in the activity of these cells, or any other changes which can occur within the immune system. Both inhibitory and stimulatory immunomodulators have been identified, some of which can have enhanced function in a tumor microenvironment. In some embodiments, the immunomodulator targets a molecule on the surface of a T cell. An "immunomodulatory target" or "immunoregulatory target" is a molecule, e.g., a cell surface molecule, that is targeted for binding by, and whose activity is altered by the binding of, a substance, agent, moiety, compound or molecule. Immunomodulatory targets include, for example, receptors on the surface of a cell ("immunomodulatory receptors") and receptor ligands ("immunomodulatory ligands").

"Immunotherapy" refers to the treatment of a subject afflicted with, or at risk of contracting or suffering a recurrence of, a disease by a method comprising inducing, enhancing, suppressing or otherwise modifying the immune system or an immune response. In certain embodiments, the immunotherapy comprises administering an antibody to a subject. In other embodiments, the immunotherapy comprises administering a small molecule to a subject. In other embodiments, the immunotherapy comprises administering a cytokine or an analog, variant, or fragment thereof.

"Immuno stimulating therapy" or "immuno stimulatory therapy" refers to a therapy that results in increasing (inducing or enhancing) an immune response in a subject for, e.g., treating cancer.

"Potentiating an endogenous immune response" means increasing the effectiveness or potency of an existing immune response in a subject. This increase in effectiveness and potency can be achieved, for example, by overcoming mechanisms that suppress the endogenous host immune response or by stimulating mechanisms that enhance the endogenous host immune response.

A therapeutically effective amount of a drug includes a "prophylactically effective amount," which is any amount of the drug that, when administered alone or in combination with an anti-neoplastic agent to a subject at risk of developing a cancer (e.g., a subject having a pre-malignant condition) or of suffering a recurrence of cancer, inhibits the development or recurrence of the cancer. In preferred embodiments, the prophylactically effective amount prevents the development or recurrence of the cancer entirely. "Inhibiting" the development or recurrence of a cancer means either lessening the likelihood of the cancer's development or recurrence, or preventing the development or recurrence of the cancer entirely.

The term "tumor mutation burden" (TMB) as used herein refers to the number of somatic mutations in a tumor's genome and/or the number of somatic mutations per area of the tumor's genome. Germline (inherited) variants are excluded when determining TMB, because the immune system has a higher likelihood of recognizing these as self. Tumor mutation burden (TMB) can also be used interchangeably with "tumor mutation load," "tumor mutational burden," or "tumor mutational load."

TMB is a genetic analysis of a tumor's genome and, thus, can be measured by applying sequencing methods well known to those of skill in the art. The tumor DNA can be compared with DNA from patient-matched normal tissue to eliminate germline mutations or polymorphisms.

In some embodiments, TMB is determined by sequencing tumor DNA using a high-throughput sequence technique, e.g., next-generation sequencing (NGS) or an NGS-based method. In some embodiments, the NGS-based method is selected from whole genome sequencing (WGS), whole exome sequencing (WES), or comprehensive genomic profiling (CGP) of cancer gene panels such as FOUNDATIONONE CDX™ and MSK-IMPACT clinical tests. In some embodiments, TMB, as used herein, refers to the number of somatic mutations per megabase (Mb) of DNA sequenced. In one embodiment, TMB is measured using the total number of nonsynonymous mutations, e.g., missense mutation (i.e. changing a particular amino acid in the protein) and/or nonsense (causing premature termination and thus truncation of the protein sequence), identified by normalizing matched tumor with germline samples to exclude any inherited germline genetic alterations. In another embodiment, TMB is measured using the total number of missense mutations in a tumor. In order to measure TMB, a sufficient amount of sample is required. In one embodiment, tissue sample (for example, a minimum of 10 slides) is used for evaluation. In some embodiments, TMB is expressed as NsMs per megabase (NsM/Mb). 1 megabase represents 1 million bases.

The TMB status can be a numerical value or a relative value, e.g., high, medium, or low; within the highest fractile, or within the top tertile, of a reference set.

The term "high TMB" as used herein refers to a number of somatic mutations in a tumor's genome that is above a number of somatic mutations that is normal or average. In some embodiments, a TMB has a score of at least 210, at least 215, at least 220, at least 225, at least 230, at least 235, at least 240, at least 245, at least 250, at least 255, at least 260, at least 265, at least 270, at least 275, at least 280, at least 285, at least 290, at least 295, at least 300, at least 305, at least 310, at least 315, at least 320, at least 325, at least 330, at least 335, at least 340, at least 345, at least 350, at least 355, at least 360, at least 365, at least 370, at least 375, at least 380, at least 385, at least 390, at least 395, at least 400, at least 405, at least 410, at least 415, at least 420, at least 425, at least 430, at least 435, at least 440, at least 445, at least 450, at least 455, at least 460, at least 465, at least 470, at least 475, at least 480, at least 485, at least 490, at least 495, or at least 500; in other embodiments a high TMB has a score of at least at least 221, at least 222, at least 223, at least 224, at least 225, at least 226, at least 227, at least 228, at least 229, at least 230, at least 231, at least 232, at least 233, at least 234, at least 235, at least 236, at least 237, at least 238, at least 239, at least 240, at least 241, at least 242, at least 243, at least 244, at least 245, at least 246, at least 247, at least 248, at least 249, or at least 250; and, in a particular embodiment, a high TMB has a score of at least 243. In other embodiments, a "high TMB" refers to a TMB within the highest fractile of the reference TMB value. For example, all subject's with evaluable TMB data are grouped according to fractile distribution of TMB, i.e., subjects are rank ordered from highest to lowest number of genetic alterations and divided into a defined number of groups. In one embodiment, all subjects with evaluable TMB data are rank ordered and divided into thirds and a "high TMB" is within the top tertile of the reference TMB value. In a particular embodiment, the tertile boundaries are 0<100 genetic alterations; 100 to 243 genetic alterations; and >243 genetic alterations. It should be understood that, once rank ordered, subjects with evaluable TMB data can be divided into any number of groups, e.g., quartiles, quintiles, etc. In some embodiments, a "high TMB" refers to a TMB of at least about 20 mutations/tumor, at least about 25 mutations/tumor, at least about 30 mutations/tumor, at least about 35 mutations/tumor, at least about 40 mutations/tumor, at least about 45 mutations/tumor, at least about 50 mutations/tumor, at least about 55 mutations/tumor, at least about 60 mutations/tumor, at least about 65 mutations/tumor, at least about 70 mutations/tumor, at least about 75 mutations/tumor, at least about 80 mutations/tumor, at least about 85 mutations/tumor, at least about 90 mutations/tumor, at least about 95 mutations/tumor, or at least about 100 mutations/tumor. In some embodiments, a "high TMB" refers to a TMB of at least about 105 mutations/tumor, at least about 110 mutations/tumor, at least about 115 mutations/tumor, at least about 120 mutations/tumor, at least about 125 mutations/tumor, at least about 130 mutations/tumor, at least about 135 mutations/tumor, at least about 140 mutations/tumor, at least about 145 mutations/tumor, at least about 150 mutations/tumor, at least about 175 mutations/tumor, or at least about 200 mutations/tumor. In certain embodiments, a tumor having a high TMB has at least about 100 mutations/tumor.

The "high TMB" can also be referred to as the number of mutations per megabase of genome sequenced, e.g., as measured by a mutation assay, e.g., FOUNDATIONONE CDX™ assay. In one embodiment, the high TMB refers to at least about 9, at least about 10, at least about 11, at least 12, at least about 13, at least about 14, at least about 15, at least about 16, at least about 17, at least about 18, at least about 19, or at least about 20 mutations per megabase of genome as measured by a FOUNDATIONONE CDX™ assay. In a particular embodiment, the "high TMB" refers to at least 10 mutations per megabase of genome sequenced by a FOUNDATIONONE CDX™ assay.

As used herein, the term "medium TMB" refers to a number of somatic mutations in a tumor's genome that is at or around a number of somatic mutations that is normal or average and the term "low TMB" refers to a number of somatic mutations in a tumor's genome that is below a number of somatic mutations that is normal or average. In a particular embodiment, a "high TMB" has a score of at least 243, a "medium TMB" has a score of between 100 and 242, and a "low TMB" has a score of less than 100 (or between 0 and 100). The "medium or low TMB" refers to less than 9 mutations per megabase of genome sequenced, e.g., as measured by a FOUNDATIONONE CDX™ assay.

The term "reference TMB value" as referred to herein can be the TMB value shown in Table 9.

In some embodiments, TMB status can correlate with smoking status. In particular, subjects who currently or formerly smoke(d) often have more genetic alterations, e.g., missense mutations, than subjects who never smoke(d).

A tumor with a high TMB can also have a high neoantigen load. As used herein, the term "neoantigen" refers to a newly formed antigen that has not been previously recognized by the immune system. A neoantigen can be a protein or peptide that is recognized as foreign (or non-self) by the immune system. Transcription of a gene in the tumor genome harboring a somatic mutation results in mutated mRNA that, when translated, gives rise to a mutated protein, which is then processed and transported to the ER lumen and binds to MHC class I complex, facilitating T-cell recognition of the neoantigen. Neoantigen recognition can promote T-cell activation, clonal expansion, and differentiation into effector and memory T-cells. Neoantigen load can correlate with TMB. In some embodiments, TMB is assessed as a surrogate for measuring tumor neoantigen load. The TMB status of a tumor can be used as a factor, alone or in combination with other factors, in determining whether a patient is likely to benefit from a particular anti-cancer agent or type of treatment or therapy, e.g., immuno-oncology agents, e.g., an anti-PD-1 antibody or antigen-binding portion thereof or an anti-PD-L1 antibody or antigen-binding portion thereof. In one embodiment, a high TMB status (or a high TMB) indicates an enhanced likelihood of benefit from immuno-oncology and, thus, can be used to identify patients more likely to benefit from therapy of an anti-PD-1 antibody or antigen-binding portion thereof. Similarly, tumors, e.g., derived from an SCLC, with high tumor neoantigen load and high TMB are more likely to be immunogenic than tumors with low neoantigen load and low TMB. In addition, high-neoantigen/high-TMB tumors, e.g., derived from an SCLC are more likely to be recognized as non-self by the immune system, thus triggering an immune-mediated antitumor response. In one embodiment, a high TMB status and a high neoantigen load indicate an enhanced likelihood of benefit from immuno-oncology, e.g., with an immunotherapy. As used herein, the term "benefit from therapy" refers to an improvement in one or more of overall survival, progression-free survival, partial response, complete response, and overall response rate and can also include a reduction in tumor growth or size, a decrease in severity of disease symptoms, an increase in frequency and duration of disease symptom-free periods, or a prevention of impairment or disability due to the disease affliction.

Other factors, e.g., environmental factors, can associate with TMB status. For example, smoking status of patients with NSCLC was correlated with TMB distribution, whereby current and former smokers had higher median TMB compared with those patients who had never smoked. See Peters et al., *AACR*, Apr. 1-5, 2017, Washington, D.C. The presence of a driver mutation in NSCLC tumors was associated with younger age, female sex, and non-smoker status. See Singal et al., *ASCO*, Jun. 1-5, 2017; Chicago, IL. A trend associating the presence of driver mutations, such as EGFR, ALK, or KRAS, with lower TMB was observed (P=0.06). Davis et al., *AACR*, Apr. 1-5, 2017, Washington, D.C.

The term "somatic mutation" as used herein refers to an acquired alteration in DNA that occurs after conception. Somatic mutations can occur in any of the cells of the body except the germ cells (sperm and egg) and therefore are not passed on to children. These alterations can, but do not always, cause cancer or other diseases. The term "germline mutation" refers to a gene change in a body's reproductive cell (egg or sperm) that becomes incorporated into the DNA of every cell in the body of the offspring. Germline mutations are passed on from parents to offspring. Also called a "hereditary mutation." In the analysis of TMB, germline mutations are considered as a "baseline," and are subtracted from the number of mutations found in the tumor biopsy to determine the TMB within the tumor, e.g., within the tumor derived from an SCLC. As germline mutations are found in every cell in the body, their presence can be determined via less invasive sample collections than tumor biopsies, such as blood or saliva. Germline mutations can increase the risk of developing certain cancers, and can play a role in the response to chemotherapy.

The term "measuring" or "measured" or "measurement" when referring to TMB status means determining a measurable quantity of somatic mutations in a biological sample of the subject. It will be appreciated that measuring can be performed by sequencing nucleic acids, e.g., cDNA, mRNA, exoRNA, ctDNA, and cfDNA, in the sample. The measuring is performed on a subject's sample and/or a reference sample or samples and can, for example, be detected de novo or correspond to a previous determination. The measuring can be performed, for example, using PCR methods, qPCR methods, Sanger sequencing methods, genomic profiling methods (including comprehensive gene panels), exome sequencing methods, genome sequencing methods, and/or any other method disclosed herein, as is known to a person of skill in the art. In some embodiments, the measuring identifies a genomic alteration in the sequenced nucleic acids. The genomic (or gene) profiling methods can involve panels of a predetermined set of genes, e.g., 150-500 genes, and in some instances the genomic alterations evaluated in the panel of genes are correlated with total somatic mutations evaluated.

The term "genomic alteration" as used herein refers to a change (or mutation) in the nucleotide sequence of the genome of a tumor, which change is not present in the germline nucleotide sequence, and which in some embodiments is a nonsynonymous mutation including, but not limited to, a base pair substitution, a base pair insertion, a base pair deletion, a copy number alteration (CNA), a gene rearrangement, and any combination thereof. In a particular embodiment, the genomic alterations measured in the biological sample are missense mutations.

The term "whole genome sequencing" or "WGS," as used herein, refers to a method of sequencing the entire genome. The term "whole exome sequencing" or "WES," as used herein, refers to a method of sequencing all the protein-coding regions (exons) of the genome.

A "cancer gene panel," "hereditary cancer panel," "comprehensive cancer panel," or "multigene cancer panel," as used herein, refers to a method of sequencing a subset of targeted cancer genes. In some embodiments, the CGP comprises sequencing at least about 15, at least about 20, at least about 25, at least about 30, at least about 35, at least about 40, at least about 45, or at least about 50 targeted cancer genes.

The term "genomic profiling assay," "comprehensive genomic profiling," or "CGP" refers to an assay that analyzes a panel of genes and selects introns for in vitro diagnosis. CGP is a combination of NGS and targeted bioinformatics analysis to screen for mutations in known clinically relevant cancer genes. This method can be used to catch mutations that are missed by testing "hotspots" (e.g., BRCA1/BRCA2 mutations or microsatellite markers). In one embodiment, the genes in the panel are cancer-related genes. In another embodiment, a genomic profiling assay is a FOUNDATIONONE® assay.

The term "harmonization" refers to a study conducted to determine the comparability between two or more measures and/or diagnostic tests. Harmonization studies provide a systematic approach to address questions of how diagnostic tests compare with each other, as well as their interchangeability when used to determine the biomarker status of a patient's tumor. In general, at least one well-characterized measure and/or diagnostic test is used as a standard for comparison with others. Concordance assessment is often utilized in harmonization studies.

The term "concordance," as used herein, refers to a degree of agreement between two measurements and/or diagnostic tests. Concordance can be established using both qualitative and quantitative methods. Quantitative methods to assess concordance differ based on the type of measurement. A particular measurement can be expressed either as 1) a categorical/dichotomized variable or 2) a continuous variable. A "categorical/dichotomized variable" (e.g., above or below TMB cut-off) may use percent agreements, such as overall percent agreement (OPA), positive percent agreement (PPA), or negative percent agreement (NPA), to assess concordance. A "continuous variable" (e.g., TMB by WES) uses Spearman's rank correlation or Pearson's correlation coefficient (r), which takes on values $-1 \leq r \leq +1$, to assess concordance across a spectrum of values (Note r=+1 or -1 means that each of the variables is perfectly correlated). The term "analytical concordance" refers to the degree of agreement in the performance (e.g., identification of biomarkers, genomic alteration types, and genomic signatures, and assessment of test reproducibility) of two assays or diagnostic tests to support clinical use. The term "clinical concordance" refers to the degree of agreement in how the two assays or diagnostic tests correlate with clinical outcome.

The term "microsatellite instability" or "MSI" refers to a change that occurs in the DNA of certain cells (such as tumor cells) in which the number of repeats of microsatellites (short, repeated sequences of DNA) is different than the number of repeats that was in the DNA when it was inherited. MSI can be high microsatellite instability (MSI-H) or low microsatellite instability (MSI-L). Microsatellites are short tandem DNA repeat sequences of 1-6 bases. These are prone to DNA replication errors, which are repaired by mismatch repair (MMR). Hence microsatellites are good indicators of genome instability, especially deficient mismatch repair (dMMR). MSI is usually diagnosed by screening 5 microsatellite markers (BAT-25, BAT-26, NR21, NR24, and NR27). MSI-H represents the presence of at least 2 unstable markers among 5 microsatellite markers analyzed (or ≥30% of the markers if a larger panel is used). MSI-L means instability of 1 MSI marker (or 10%-30% of markers in larger panels). MSS means the absence of an unstable microsatellite marker.

The term "biological sample" as used herein refers to biological material isolated from a subject. The biological sample can contain any biological material suitable for determining TMB, for example, by sequencing nucleic acids in the tumor (or circulating tumor cells) and identifying a genomic alteration in the sequenced nucleic acids. The biological sample can be any suitable biological tissue or fluid such as, for example, tumor tissue, blood, blood plasma, and serum. In one embodiment, the sample is a tumor tissue biopsy, e.g., a formalin-fixed, paraffin-embedded (FFPE) tumor tissue or a fresh-frozen tumor tissue or the like. In another embodiment, the biological sample is a liquid biopsy that, in some embodiments, comprises one or more of blood, serum, plasma, circulating tumor cells, exoRNA, ctDNA, and cfDNA.

The terms "once about every week," "once about every two weeks," or any other similar dosing interval terms as used herein mean approximate numbers. "Once about every week" can include every seven days±one day, i.e., every six days to every eight days. "Once about every two weeks" can include every fourteen days±three days, i.e., every eleven days to every seventeen days. Similar approximations apply, for example, to once about every three weeks, once about every four weeks, once about every five weeks, once about every six weeks, and once about every twelve weeks. In some embodiments, a dosing interval of once about every six weeks or once about every twelve weeks means that the first dose can be administered any day in the first week, and then the next dose can be administered any day in the sixth or twelfth week, respectively. In other embodiments, a dosing interval of once about every six weeks or once about every twelve weeks means that the first dose is administered on a particular day of the first week (e.g., Monday) and then the next dose is administered on the same day of the sixth or twelfth weeks (i.e., Monday), respectively.

The use of the alternative (e.g., "or") should be understood to mean either one, both, or any combination thereof of the alternatives. As used herein, the indefinite articles "a" or "an" should be understood to refer to "one or more" of any recited or enumerated component.

The terms "about" or "comprising essentially of" refer to a value or composition that is within an acceptable error range for the particular value or composition as determined by one of ordinary skill in the art, which will depend in part on how the value or composition is measured or determined, i.e., the limitations of the measurement system. For example, "about" or "comprising essentially of" can mean within 1 or more than 1 standard deviation per the practice in the art. Alternatively, "about" or "comprising essentially of" can mean a range of up to 10%. Furthermore, particularly with respect to biological systems or processes, the terms can mean up to an order of magnitude or up to 5-fold of a value. When particular values or compositions are provided in the application and claims, unless otherwise stated, the meaning of "about" or "comprising essentially of" should be assumed to be within an acceptable error range for that particular value or composition.

As described herein, any concentration range, percentage range, ratio range or integer range is to be understood to include the value of any integer within the recited range and, when appropriate, fractions thereof (such as one tenth and one hundredth of an integer), unless otherwise indicated.

A list of abbreviations is provided in Table 1.

TABLE 1

List of Abbreviations

| Term | Definition |
|---|---|
| Ab | antibody |
| AE | adverse event |
| ALK | anaplastic lymphoma kinase |
| AUC | area under the concentration-time curve |
| BICR | blinded independent central review |
| BMS | Bristol-Myers Squibb |
| BSA | body surface area |
| cfDNA | cell-free DNA |
| CI | confidence interval |
| CNS | central nervous system |
| CONSORT | consolidated standards of reporting trials |
| CR | complete response |
| ctDNA | circulating tumor DNA |
| CTLA-4 | cytotoxic T-lymphocyte-associated protein 4 |
| ECOG | Eastern Cooperative Oncology Group |
| e.g. | exempli gratia (for example) |
| EGFR | epidermal growth factor receptor |
| ELISA | enzyme-linked immunosorbent assay |
| exoRNA | exosomal RNA |
| HuMab | human antibody; human monoclonal antibody |

TABLE 1-continued

List of Abbreviations

| Term | Definition |
|---|---|
| i.e. | id est (that is) |
| IV | Intravenous |
| Kg | kilogram |
| mAb | monoclonal antibody |
| MB | megabase |
| mg | milligram |
| MO | month |
| N | number of subjects or observations |
| NCCN | National Comprehensive Cancer Network |
| ORR | overall response rate |
| OS | overall survival |
| PD-1 | programmed death-1 |
| PD-L1 | programmed death-ligand 1 |
| PD-L2 | programmed death-ligand 2 |
| PFS | progression-free survival |
| PR | partial response |
| Q2W | once every two weeks |
| Q6W | once every six weeks |
| Q12W | once every twelve weeks |
| RECIST | response evaluation criteria in solid tumors |
| SCLC | small cell lung cancer |
| TILs | tumor infiltrating lymphocytes |
| TMB | tumor mutation burden |
| WES | whole exome sequencing |
| WGS | whole genome sequencing |

Various aspects of the disclosure are described in further detail in the following subsections.

Methods of the Disclosure

Certain aspects of the present disclosure are directed to a method for identifying a subject who is afflicted with a tumor derived from an SCLC and suitable for treatment with an anti-PD-1 antibody or antigen-binding portion thereof ("anti-PD-1 antibody") or an anti-PD-L1 antibody or antigen-binding portion thereof ("anti-PD-L1 antibody") comprising measuring a tumor mutational burden (TMB) status of a biological sample of the subject. Other aspects of the present disclosure are directed to a method of identifying a subject who is afflicted with a tumor derived from an SCLC and suitable for treatment with an anti-PD-1 antibody and an anti-CTLA-4 antibody comprising measuring a tumor mutational burden (TMB) status of a biological sample of the subject.

As a tumor grows, it accumulates somatic mutations not present in germline DNA. Tumor mutation burden (TMB) refers to the number of somatic mutations in a tumor's genome and/or the number of somatic mutations per area of the tumor genome (after taking into account germline variant DNA). The acquisition of somatic mutations and, thus, a higher TMB can be influenced by distinct mechanisms, such as exogenous mutagen exposure (e.g., tobacco smoking or UV light exposure) and DNA mismatch repair mutations (e.g., MSI in colorectal and esophageal cancers). In solid tumors, about 95% of mutations are single-base substitutions. (Vogelstein et al., Science (2013) 339:1546-1558.) A "nonsynonymous mutation" herein refers to a nucleotide mutation that alters the amino acid sequence of a protein. Missense mutations and nonsense mutations can be both nonsynonymous mutations. A "missense mutation" herein refers to a nonsynonymous point mutation in which a single nucleotide change results in a codon that codes for a different amino acid. A "nonsense mutation" herein refers to a nonsynonymous point mutation in which a codon is changed to a premature stop codon that leads to truncation of the resulting protein.

In one embodiment, somatic mutations can be expressed at the RNA and/or protein level, resulting in neoantigens (also referred to as neoepitopes). Neoantigens can influence an immune-mediated anti-tumor response. For example, neoantigen recognition can promote T-cell activation, clonal expansion, and differentiation into effector and memory T-cells.

As a tumor develops, early clonal mutations (or "trunk mutations") can be carried by most or all tumor cells, while late mutations (or "branch mutations") can occur in only a subset of tumor cells or regions. (Yap et al., Sci Tranl Med (2012) 4:1-5; Jamai-Hanjani et al., (2015) Clin Cancer Res 21:1258-1266.) As a result, neoantigens derived from clonal "trunk" mutations are more widespread in the tumor genome than "branch" mutations and, thus, can lead to a high number of T cells reactive against the clonal neoantigen. (McGranahan et al., (2016) 351:1463-1469.) Generally, tumors with a high TMB can also have a high neoantigen load, which can lead to high tumor immunogenicity and increased T-cell reactivity and anti-tumor response. As such, cancers with a high TMB can respond well to treatment with immunotherapies, e.g., an anti-PD-1 antibody or anti-PD-L1 antibody.

Advances in sequencing technologies allow for evaluation of the tumor's genomic mutation landscape. Any sequencing methods known to those of skill in the art can be used to sequence nucleic acids from the tumor genome (e.g., obtained from a biological sample from a subject afflicted with a tumor). In one embodiment, PCR or qPCR methods, Sanger sequencing methods, or next-generation sequencing ("NGS") methods (such as genomic profiling, exome sequencing, or genome sequencing) can be used to measure TMB. In some embodiments, the TMB status is measured using genomic profiling. Genomic profiling involves analyzing nucleic acids from tumor samples, including coding and non-coding regions, and can be performed using methods having integrated optimized nucleic acid selection, read alignment, and mutation calling. In some embodiments, gene profiling provides next generation sequencing (NGS)-based analysis of tumors that can be optimized on a cancer-by-cancer, gene-by-gene, and/or site-by-site basis. Genome profiling can integrate the use of multiple, individually tuned, alignment methods or algorithms to optimize performance in sequencing methods, particularly in methods that rely on massively parallel sequencing of a large number of diverse genetic events in a large number of diverse genes. Genomic profiling provides for a comprehensive analysis of a subject's cancer genome, with clinical grade quality, and the output of the genetic analysis can be contextualized with relevant scientific and medical knowledge to increase the quality and efficiency of cancer therapy.

Genomic profiling involves a panel of a predefined set of genes comprising as few as five genes or as many as 1000 genes, about 25 genes to about 750 genes, about 100 genes to about 800 genes, about 150 genes to about 500 genes, about 200 genes to about 400 genes, about 250 genes to about 350 genes. In one embodiment, the genomic profile comprises at least 300 genes, at least 305 genes, at least 310 genes, at least 315 genes, at least 320 genes, at least 325 genes, at least 330 genes, at least 335 genes, at least 340 genes, at least 345 genes, at least 350 genes, at least 355 genes, at least 360 genes, at least 365 genes, at least 370 genes, at least 375 genes, at least 380 genes, at least 385 genes, at least 390 genes, at least 395 genes, or at least 400 genes. In another embodiment, the genomic profile comprises at least 325 genes. In a particular embodiment, the genomic profile comprises at least 315 cancer-related genes and introns in 28 genes (FOUNDATIONONE®) or the complete DNA coding sequence of 406 genes, introns in 31 genes with rearrangements, and the RNA sequence (cDNA) of 265 genes (FOUNDATIONONE® Heme). In another embodiment, the genomic profile comprises 26 genes and 1000 associated mutations (EXODX® Solid Tumor). In yet another embodiment, the genomic profile comprises 76 genes (Guardant360). In yet another embodiment, the genomic profile comprises 73 genes (Guardant360). In another embodiment, the genomic profile comprises 354 genes and introns in 28 genes for rearrangements (FOUNDATIONONE® CDX™). In certain embodiments, the genomic profile is FOUNDATIONONE® F1CDx. In another embodiment, the genomic profile comprises 468 genes (MSK-IMPACT™). One or more genes can be added to the genome profile as more genes are identified to be related to oncology.

FOUNDATIONONE® Assay

The FOUNDATIONONE® assay is comprehensive genomic profiling assay for solid tumors, including but not limited to solid tumors of the lung, colon, and breast, melanoma, and ovarian cancer. The FOUNDATIONONE® assay uses a hybrid-capture, next-generation sequencing test to identify genomic alterations (base substitutions, insertions and deletions, copy number alterations, and rearrangements) and select genomic signatures (e.g., TMB and microsatellite instability). The assay covers 322 unique genes, including the entire coding region of 315 cancer-related genes, and selected introns from 28 genes. The full list of FOUNDATIONONE® assay genes is provided in Tables 2 and 3. See FOUNDATIONONE: Technical Specifications, Foundation Medicine, Inc., available at FoundationMedicine.com, last visited Mar. 16, 2018, which is incorporated by reference herein in its entirety.

TABLE 2

List of genes wherein entire coding sequences are assayed in the FOUNDATIONONE ® assay.

| ABL1 | BRAF | CHEK1 | FANCC | GATA3 | JAK2 | MITF | PDCD1LG2 (PD-L2) | RBM10 | STAT4 |
|---|---|---|---|---|---|---|---|---|---|
| ABL2 | BRCA1 | CHEK2 | FANCD2 | GATA4 | JAK3 | MLH1 | PDGFRA | RET | STK11 |
| ACVR1B | BRCA2 | CIC | FANCE | GATA6 | JUN | MPL | PDGFRB | RICTOR | SUFU |
| AKT1 | BRD4 | CREBBP | FANCF | GID4 (C17orf39) | KAT6A (MYST3) | MRE11A | PDK1 | RNF43 | SYK |
| AKT2 | BRIP1 | CRKL | FANCG | GLI1 | KDM5A | MSH2 | PIK3C2B | ROS1 | TAF1 |
| AKT3 | BTG1 | CRLF2 | FANCL | GNA11 | KDM5C | MSH6 | PIK3CA | RPTOR | TBX3 |
| ALK | BTK | CSF1R | FAS | GNA13 | KDM6A | MTOR | PIK3CB | RUNX1 | TERC |
| AMER1 (FAM123B) | C11orf 30 (EMSY) | CTCF | FAT1 | GNAQ | KDR | MUTYH | PIK3CG | RUNX1T1 | TERT (Promoter only) |
| APC | CARD11 | CTNNA1 | FBXW7 | GNAS | KEAP1 | MYC | PIK3R1 | SDHA | TET2 |
| AR | CBFB | CTNNB1 | FGF10 | GPR124 | KEL | MYCL (MYCL1) | PIK3R2 | SDHB | TGFBR2 |

TABLE 2-continued

List of genes wherein entire coding sequences are assayed in the FOUNDATIONONE ® assay.

| | | | | | | | | | |
|---|---|---|---|---|---|---|---|---|---|
| ARAF | CBL | CUL3 | FGF14 | GRIN2A | KIT | MYCN | PLCG2 | SDHC | TNFAIP3 |
| ARFRP1 | CCND1 | CYLD | FGF19 | GRM3 | KLHL6 | MYD88 | PMS2 | SDHD | TNFRSF14 |
| ARID1A | CCND2 | DAXX | FGF23 | GSK3B | KMT2A (MLL) | NF1 | POLD1 | SETD2 | TOP1 |
| ARID1B | CCND3 | DDR2 | FGF3 | H3F3A | KMT2C (MLL3) | NF2 | POLE | SF3B1 | TOP2A |
| ARID2 | CCNE1 | DICER1 | FGF4 | HGF | KMT2D (MLL2) | NFE2L2 | PPP2R1A | SLIT2 | TP53 |
| ASXL1 | CD274 (PD-L1) | DNMT3A | FGF6 | HNF1A | KRAS | NFKBIA | PRDM1 | SMAD2 | TSC1 |
| ATM | CD79A | DOT1L | FGFR1 | HRAS | LMO1 | NKX2-1 | PREX2 | SMAD3 | TSC2 |
| ATR | CD79B | EGFR | FGFR2 | HSD3B1 | LRP1B | NOTCH1 | PRKAR1A | SMAD4 | TSHR |
| ATRX | CDC73 | EP300 | FGFR3 | HSP90AA1 | LYN | NOTCH2 | PRKCI | SMARCA4 | U2AF1 |
| AURKA | CDH1 | EPHA3 | FGFR4 | IDH1 | LZTR1 | NOTCH3 | PRKDC | SMARCB1 | VEGFA |
| AURKB | CDK12 | EPHA5 | FH | IDH2 | MAGI2 | NPM1 | PRSS8 | SMO | VHL |
| AXIN1 | CDK4 | EPHA7 | FLCN | IGF1R | MAP2K1 (MEK1) | NRAS | PTCH1 | SNCAIP | WISP3 |
| AXL | CDK6 | EPHB1 | FLT1 | IGF2 | MAP2K2 (MEK2) | NSD1 | PTEN | SOCS1 | WT1 |
| BAP1 | CDK8 | ERBB2 | FLT3 | IKBKE | MAP2K4 | NTRK1 | PTPN11 | SOX10 | XPO1 |
| BARD1 | CDKN1A | ERBB3 | FLT4 | IKZF1 | MAP3K1 | NTRK2 | QKI | SOX2 | ZBTB2 |
| BCL2 | CDKN1B | ERBB4 | FOXL2 | IL7R | MCL1 | NTRK3 | RAC1 | SOX9 | ZNF217 |
| BCL2L1 | CDKN2A | ERG | FOXP1 | INHBA | MDM2 | NUP93 | RAD50 | SPEN | ZNF703 |
| BCL2L2 | CDKN2B | ERRFl1 | FRS2 | INPP4B | MDM4 | PAK3 | RAD51 | SPOP | |
| BCL6 | CDKN2C | ESR1 | FUBP1 | IRF2 | MED12 | PALB2 | RAF1 | SPTA1 | |
| BCOR | CEBPA | EZH2 | GABRA6 | IRF4 | MEF2B | PARK2 | RANBP2 | SRC | |
| BCORL1 | CHD2 | FAM46C | GATA1 | IRS2 | MEN1 | PAX5 | RARA | STAG2 | |
| BLM | CHD4 | FANCA | GATA2 | JAK1 | MET | PBRM1 | RB1 | STAT3 | |

TABLE 3

List of genes wherein selected introns are assayed in the FOUNDATIONONE ® assay.

| | | | | | | |
|---|---|---|---|---|---|---|
| ALK | BRCA1 | ETV1 | FGFR1 | MSH2 | NTRK1 | RARA |
| BCL2 | BRCA2 | ETV4 | FGFR2 | MYB | NTRK2 | RET |
| BCR | BRD4 | ETV5 | FGFR3 | MYC | PDGFRA | ROS1 |
| BRAF | EGFR | ETV6 | KIT | NOTCH2 | RAF1 | TMPRSS2 |

EXODX® Solid Tumor Assay

In one embodiment, TMB is measured using the EXODX® Solid Tumor assay. The EXODX® Solid Tumor assay is an exoRNA- and cfDNA-based assay, which detects actionable mutations in cancer pathways. The EXODX® Solid Tumor assay is a plasma-based assay that does not require a tissue sample. The EXODX® Solid Tumor assay covers 26 genes and 1000 mutations. The specific genes covered by the EXODX® Solid Tumor assay are shown in Table 4. See Plasma-Based Solid Tumor Mutation Panel Liquid Biopsy, Exosome Diagnostics, Inc., available at exosomedx.com, last accessed on Mar. 16, 2018.

TABLE 4

Genes covered by the EXODX ® Solid Tumor assay.

| | | | | | | | | |
|---|---|---|---|---|---|---|---|---|
| BRAF | MEK1 | KIT | ROS1 | ALK | PTEN | TP53 | FGFR3 | TSC2 |
| NRAS | KRAS | PDGFRA | RET | AKT1 | DH2 | NOTCH1 | NTRK1 | CDKN2A |
| PIK3CA | EGFR | EML4-ALK | HER-2/ NEU; ERBB2 | ARv7 | mTOR | Hedgehog | TSC1 | |

FOUNDATIONONE®; LiquidAssay

In one embodiment, TMB is measured using the FOUNDATIONONE® Liquid assay. The FOUNDATIONONE® Liquid assay is cfDNA-based assay, which detects circulating tumor DNA (ctDNA). The assay is a plasma-based assay that does not require a solid tissue sample. The FOUNDATIONONE® Liquid assay covers 70 genes. The specific genes covered by the FOUNDATIONONE® Liquid assay are shown in Tables 5A-5C. See FOUNDATIONONE® Liquid, Technical Specifications, Foundation Medicine, available at assets.ctfassets.net/vhribv12lmne/3SPY-AcbGdqAeMsOqMyKUog/
d0eb51659e08d733bf39971e85ed940d/
F1L_TechnicalInformation_MKT-0061-04.pdf, last accessed on Oct. 6, 2018.

TABLE 5A

Genes covered by the FOUNDATIONONE ® Liquid Assay: Entire Coding Sequence.

| | | | | | | |
|---|---|---|---|---|---|---|
| APC | CCND1 | CDK12 | ERBB2 | KRAS | NF1 | RB1 |
| AR | CD274 (PD-L1) | CDKN2A | ERRFl1 | MDM2 | PALB2 | SMO |
| ATM | CDH1 | CHEK2 | FGFR1 | MET | PDCD1LG2 (PD-L2) | STK11 |
| BRCA1 | CDK4 | CRKL | FGFR2 | MYC | PTEN | TP53 |
| BRCA2 | CDK6 | EGFR | FOXL2 | MYCN | PTPN11 | VEGFA |

TABLE 5B

| \multicolumn{7}{c|}{Genes covered by the FOUNDATIONONE ® Liquid Assay: Select Exons.} |
|---|---|---|---|---|---|---|
| ABL1 | BTK | FGFR3 | HRAS | KIT | MYD88 | PIK3CA |
| AKT1 | CTNNB1 | FLT3 | IDH1 | MAP2K1 (MEK1) | NPM1 | RAF1 |
| ALK | DDR2 | GNA11 | IDH2 | MAP2K2 (MEK2) | NRAS | RET |
| ARAF | ESR1 | GNAQ | JAK2 | MPL | PDGFRA | ROS1 |
| BRAF | EZH2 | GNAS | JAK3 | MTOR | PDGFRB | TERT |

TABLE 5C

| Genes covered by the FOUNDATIONONE ® Liquid Assay: Select Rearrangements. |
|---|
| ALK   EGFR   FGFR2   FGFR3   PDGFRA   RET   ROS1 |

Guardant360 Assay

In some embodiments, TMB status is determined using the Guardant360 assay. The Guardant360 assay measures mutations in at least 73 genes (Table 6), 23 indels (Table 7), 18 CNVs (Table 8), and 6 fusion genes (Table 9). See GuardantHealth.com, last accessed on Mar. 16, 2018. In some embodiments, TMB status is determined using the GUARDANTOMNI™ assay. The GUARDANTOMNI™ assay is a comprehensive genomic profiling tool, comprising a 500-gene panel.

TABLE 6

| \multicolumn{7}{c|}{Guardant360 assay genes.} |
|---|---|---|---|---|---|---|
| AKT1 | CCND2 | EZH2 | IDH1 | MLH1 | PDGFRA | SMAD4 |
| ALK | CCNE1 | FBXW7 | IDH2 | MPL | PIK3CA | SMO |
| APC | CDH1 | FGFR1 | JAK2 | MTOR | PTEN | STK11 |
| AR | CDK4 | FGFR2 | JAK3 | MYC | PTPN11 | TERT (including promoter) |
| ARAF | CDK6 | FGFR3 | KIT | NF1 | RAF1 | TP53 |
| ARID1A | CDKN2A | GATA3 | KRAS | NFE2L2 | RB1 | TSC1 |
| ATM | CTNNB1 | GNA11 | MAP2K1 | NOTCH1 | RET | VHL |
| BRAF | DDR2 | GNAQ | MAP2K2 | NPM1 | RHEB | |
| BRCA1 | EGFR | GNAS | MAPK1 | NRAS | RHOA | |
| BRCA2 | ERBB2 | HNF1A | MAPK3 | NTRK1 | RIT1 | |
| CCND1 | ESR1 | HRAS | MET | NTRK3 | ROS1 | |

TABLE 7

| \multicolumn{8}{c|}{Guardant360 assay indels.} |
|---|---|---|---|---|---|---|---|
| APC | BRCA1 | CDKN2A | GATA3 | MLH1 | PDGFRA | SMAD4 | TSC1 |
| ARID1A | BRCA2 | EGFR | KIT | MTOR | PTEN | STK11 | VHL |
| ATM | CDH1 | ERBB2 | MET | NF1 | RB1 | TP53 | |

TABLE 8

| \multicolumn{6}{c|}{Guardant360 assay amplifications (CNVs).} |
|---|---|---|---|---|---|
| AR | CCND2 | CDK6 | FGFR1 | KRAS | PDGFRA |
| BRAF | CCNE1 | EGFR | FGFR2 | MET | PIK3CA |
| CCND1 | CDK4 | ERBB2 | KIT | MYC | RAF1 |

TABLE 9

| Guardant360 assay fusions. |
|---|
| ALK     FGFR3     RET |
| FGFR2   NTRK1     ROS1 |

ILLUMINA® TruSight Assay

In some embodiments, TMB is determined using the TruSight Tumor 170 assay (ILLUMINA). The TruSight Tumor 170 assay is a next-generation sequencing assay that covers 170 genes associated with common solid tumors, which simultaneously analyzes DNA and RNA. The TruSight Tumor 170 assay assesses fusions, splice variants, insertions/deletions, single nucleotide variants (SNVs), and amplifications. The TruSight Tumor 170 assay gene lists are shown in Tables 10-12.

TABLE 10

| \multicolumn{6}{c|}{TruSight Tumor 170 assay genes (amplifications).} |
|---|---|---|---|---|---|
| AKT2 | CDK4 | FGF1 | FGF7 | LAMP1 | PDGFRB |
| ALK | CDK6 | FGF10 | FGF8 | MDM2 | PIK3CA |
| AR | CHEK1 | FGF14 | FGF9 | MDM4 | PIK3CB |
| ATM | CHEK2 | FGF19 | FGFR1 | MET | PTEN |
| BRAF | EGFR | FGF2 | FGFR2 | MYC | RAF1 |
| BRCA1 | ERBB2 | FGF23 | FGFR3 | MYCL1 | RET |
| BRCA2 | ERBB3 | FGF3 | FGFR4 | MYCN | RICTOR |
| CCND1 | ERCC1 | FGF4 | JAK2 | NRAS | RPS6KB1 |
| CCND3 | ERCC2 | FGF5 | KIT | NRG1 | TFRC |
| CCNE1 | ESR1 | FGF6 | KRAS | PDGFRA | |

TABLE 11

TruSight Tumor 170 assay genes (fusions).

| | | | | | | | |
|---|---|---|---|---|---|---|---|
| ABL1 | BRCA1 | ERG | FGFR1 | JAK2 | MSH2 | NTRK2 | PPARG |
| AKT3 | BRCA2 | ESR1 | FGFR2 | KDR | MYC | NTRK3 | RAF1 |
| ALK | CDK4 | ETS1 | FGFR3 | KIF5B | NOTCH1 | PAX3 | RET |
| AR | CSF1R | ETV1 | FGFR4 | KIT | NOTCH2 | PAX7 | ROS1 |
| AXL | EGFR | ETV4 | FLI1 | KMT2A (MLL) | NOTCH3 | PDGFRA | RPS6KB1 |
| BCL2 | EML4 | ETV5 | FLT1 | MET | NRG1 | PDGFRB | TMPRSS2 |
| BRAF | ERBB2 | EWSR1 | FLT3 | MLLT3 | NTRK1 | PIK3CA | |

TABLE 12

TruSight Tumor 170 assay genes (small variants).

| | | | | | | | | | |
|---|---|---|---|---|---|---|---|---|---|
| AKT1 | BRCA2 | CHEK1 | ESR1 | FGF7 | HRAS | MET | NF1 | PMS2 | SLX4 |
| AKT2 | BRIP1 | CHEK2 | EZH2 | FGF8 | IDH1 | MLH1 | NOTCH1 | PPP2R2A | SMAD4 |
| AKT3 | BTK | CREBBP | FAM175A | FGF9 | IDH2 | MLLT3 | NOTCH2 | PTCH1 | SMARCB1 |
| ALK | CARD11 | CSF1R | FANCI | FGFR1 | INPP4B | MPL | NOTCH3 | PTEN | SMO |
| APC | CCND1 | CTNNB1 | FANCL | FGFR2 | JAK2 | MRE11A | NPM1 | PTPN11 | SRC |
| AR | CCND2 | DDR2 | FBXW7 | FGFR3 | JAK3 | MSH2 | NRAS | RAD51 | STK11 |
| ARID1A | CCNE1 | DNMT3A | FGF1 | FGFR4 | KDR | MSH3 | NRG1 | RAD51B | TERT |
| ATM | CD79A | EGFR | FGF10 | FLT1 | KIT | MSH6 | PALB2 | RAD51C | TET2 |
| ATR | CD79B | EP300 | FGF14 | FLT3 | KMT2A (MLL) | MTOR | PDGFRA | RAD51D | TP53 |
| BAP1 | CDH1 | ERBB2 | FGF2 | FOXL2 | KRAS | MUTYH | PDGFRB | RAD54L | TSC1 |
| BARD1 | CDK12 | ERBB3 | FGF23 | GEN1 | MAP2K1 | MYC | PIK3CA | RB1 | TSC2 |
| BCL2 | CDK4 | ERBB4 | FGF3 | GNA11 | MAP2K2 | MYCL1 | PIK3CB | RET | VHL |
| BCL6 | CDK6 | ERCC1 | FGF4 | GNAQ | MCL1 | MYCN | PIK3CD | RICTOR | XRCC2 |
| BRAF | CDKN2A | ERCC2 | FGF5 | GNAS | MDM2 | MYD88 | PIK3CG | ROS1 | |
| BRCA1 | CEBPA | ERG | FGF6 | HNF1A | MDM4 | NBN | PIK3R1 | RPS6KB1 | |

FOUNDATIONONE® F1CDx Assay

FOUNDATIONONE® CDX™ ("F1CDx") is a next generation sequencing based in vitro diagnostic device for detection of substitutions, insertion and deletion alterations (indels), and copy number alterations (CNAs) in 324 genes and select gene rearrangements, as well as genomic signatures including microsatellite instability (MSI) and tumor mutation burden (TMB) using DNA isolated from formalin-fixed paraffin embedded (FFPE) tumor tissue specimens. F1CDx is approved by the United States Food and Drug Administration (FDA) for several tumor indications, including NSCLC, melanoma, breast cancer, colorectal cancer, and ovarian cancer.

The F1CDx assay employs a single DNA extraction method from routine FFPE biopsy or surgical resection specimens, 50-1000 ng of which will undergo whole-genome shotgun library construction and hybridization-based capture of all coding exons from 309 cancer-related genes, one promoter region, one non-coding (ncRNA), and selected intronic regions from 34 commonly rearranged genes, 21 of which also include the coding exons. Tables 13A and 13B provide the complete list of genes included in F1CDx. In total, the assay detects alterations in a total of 324 genes. Using the ILLUMINA® HiSeq 4000 platform, hybrid capture-selected libraries are sequenced to high uniform depth (targeting >500× median coverage with >99% of exons at coverage >100×). Sequence data is then processed using a customized analysis pipeline designed to detect all classes of genomic alterations, including base substitutions, indels, copy number alterations (amplifications and homozygous gene deletions), and selected genomic rearrangements (e.g., gene fusions). Additionally, genomic signatures including microsatellite instability (MSI) and tumor mutation burden (TMB) are reported.

TABLE 13A

Genes with full coding exonic regions included in FOUNDATIONONE ® CDX ™ for the detection of substitutions, insertions and deletions (indels), and copy number alterations (CNAs).

| | | | | | | | | | |
|---|---|---|---|---|---|---|---|---|---|
| ABL1 | BRCA2 | CDKN2C | ERCC4 | GATA3 | KDM5C | MRE11A | PARP2 | RAD51 | SOX9 |
| ACVR1B | BRD4 | CEBPA | ERG | GATA4 | KDM6A | MSH2 | PARP3 | RAD51B | SPEN |
| AKT1 | BRIP1 | CHEK1 | ERRFI1 | GATA6 | KDR | MSH3 | PAX5 | RAD51C | SPOP |
| AKT2 | BTG1 | CHEK2 | ESR1 | GID4 (C17orf39) | KEAP1 | MSH6 | PBRM1 | RAD51D | SRC |
| AKT3 | BTG2 | CIC | EZH2 | GNA11 | KEL | MST1R | PDCD1 | RAD52 | STAG2 |
| ALK | BTK | CREBBP | FAM46C | GNA13 | KIT | MTAP | PDCD1LG2 | RAD54L | STAT3 |
| ALOX12B | C11orf30 | CRKL | FANCA | GNAQ | KLHL6 | MTOR | PDGFRA | RAF1 | STK11 |
| AMER1 | CALR | CSF1R | FANCC | GNAS | KMT2A (MLL) | MUTYH | PDGFRB | RARA | SUFU |
| APC | CARD11 | CSF3R | FANCG | GRM3 | KMT2D (MLL2) | MYC | PDK1 | RB1 | SYK |
| AR | CASP8 | CTCF | FANCL | GSK3B | KRAS | MYCL | PIK3C2B | RBM10 | TBX3 |
| ARAF | CBFB | CTNNA1 | FAS | H3F3A | LTK | MYCN | PIK3C2G | REL | TEK |
| ARFRP1 | CBL | CTNNB1 | FBXW7 | HDAC1 | LYN | MYD88 | PIK3CA | RET | TET2 |
| ARID1A | CCND1 | CUL3 | FGF10 | HGF | MAF | NBN | PIK3CB | RICTOR | TGFBR2 |

TABLE 13A-continued

Genes with full coding exonic regions included in FOUNDATIONONE ® CDX ™
for the detection of substitutions, insertions and deletions (indels), and copy number alterations (CNAs).

| | | | | | | | | | |
|---|---|---|---|---|---|---|---|---|---|
| ASXL1 | CCND2 | CUL4A | FGF12 | HNF1A | MAP2K1 | NF1 | PIK3R1 | RNF43 | TIPARP |
| ATM | CCND3 | CXCR4 | FGF14 | HRAS | MAP2K2 | NF2 | PIM1 | ROS1 | TNFAIP3 |
| ATR | CCNE1 | CYP17A1 | FGF19 | HSD3B1 | MAP2K4 | NFE2L2 | PMS2 | RPTOR | TNFRSF14 |
| ATRX | CD22 | DAXX | FGF23 | ID3 | MAP3K1 | NFKBIA | POLD1 | SDHA | TP53 |
| AURKA | CD274 | DDR1 | FGF3 | IDH1 | MAP3K13 | NKX2-1 | POLE | SDHB | TSC1 |
| AURKB | CD70 | DDR2 | FGF4 | IDH2 | MAPK1 | NOTCH1 | PPARG | SDHC | TSC2 |
| AXIN1 | CD79A | DIS3 | FGF6 | IGF1R | MCL1 | NOTCH2 | PPP2R1A | SDHD | TYRO3 |
| AXL | CD79B | DNMT3A | FGFR1 | IKBKE | MDM2 | NOTCH3 | PPP2R2A | SETD2 | U2AF1 |
| BAP1 | CDC73 | DOT1L | FGFR2 | IKZF1 | MDM4 | NPM1 | PRDM1 | SF3B1 | VEGFA |
| BARD1 | CDH1 | EED | FGFR3 | INPP4B | MED12 | NRAS | PRKAR1A | SGK1 | VHL |
| BCL2 | CDK12 | EGFR | FGFR4 | IRF2 | MEF2B | NT5C2 | PRKC1 | SMAD2 | WHSC1 |
| BCL2L1 | CDK4 | EP300 | FH | IRF4 | MEN1 | NTRK1 | PTCH1 | SMAD4 | WHSC1L1 |
| BCL2L2 | CDK6 | EPHA3 | FLCN | IRS2 | MERTK | NTRK2 | PTEN | SMARCA4 | WT1 |
| BCL6 | CDK8 | EPHB1 | FLT1 | JAK1 | MET | NTRK3 | PTPN11 | SMARCB1 | XPO1 |
| BCOR | CDKN1A | EPHB4 | FLT3 | JAK2 | MITF | P2RY8 | PTPRO | SMO | XRCC2 |
| BCORL1 | CDKN1B | ERBB2 | FOXL2 | JAK3 | MKNK1 | PALB2 | QKI | SNCAIP | ZNF217 |
| BRAF | CDKN2A | ERBB3 | FUBP1 | JUN | MLH1 | PARK2 | RAC1 | SOCS1 | ZNF703 |
| BRCA1 | CDKN2B | ERBB4 | GABRA6 | KDM5A | MPL | PARP1 | RAD21 | SOX2 | |

TABLE 13B

Genes with selected intronic regions for the detection of gene rearrangements,
one with 3'UTR, one gene with a promoter region and one ncRNA gene.

| | | | | | | | | |
|---|---|---|---|---|---|---|---|---|
| ALK introns 18, 19 | BRCA1 introns 2, 7, 8, 12, 16, 19, 20 | ETV4 introns 5, 6 | EZR introns 9-11 | KIT intron 16 | MYC intron 1 | NUTM1 intron 1 | RET introns 7-11 | SLC34A2 intron 4 |
| BCL2 3'UTR | BRCA2 intron 2 | ETV5 introns 6, 7 | FGFR1 intron 1, 5, 17 | KMT2A (MLL) introns 6-11 | NOTCH2 intron 26 | PDGFRA introns 7, 9, 11 | ROS1 introns 31-35 | TERC ncRNA |
| BCR introns 8, 13, 14 | CD74 introns 6-8 | ETV6 introns 5, 6 | FGFR2 intron 1, 17 | MSH2 intron 5 | NTRK1 introns 8-10 | RAF1 introns 4-8 | RSPO2 intron 1 | TERT Promoter |
| BRAF introns 7-10 | EGFR introns 7, 15, 24-27 | EWSR1 introns 7-13 | FGFR3 intron 17 | MYB intron 14 | NTRK2 Intron 12 | RARA intron 2 | SDC4 intron 2 | TMPRSS2 introns 1-3 |

The F1CDx assay identifies various alterations in the gene and/or intron sequences, including substitutions, insertions/deletions, and CNAs. The F1CDx assay was previously identified as having concordance with an externally validated NGS assay and the FOUNDATIONONE® (F1 LDT) assay. See FOUNDATIONONE® CDX™: Technical Information, Foundation Medicine, Inc., available at Foundation-Medicine.com, last visited Mar. 16, 2018, which is incorporated by reference herein in its entirety.

MSK-IMPACT™

In some embodiments, TMB status is assessed using the MSK-IMPACT™ assay. The MSK-IMPACT™ assay uses next-generation sequencing to analyze the mutation status of 468 genes. Target genes are captured and sequenced on an ILLUMINA HISEQ™ instrument. The MSK-IMPACT™ assay is approved by the US FDA for detection of somatic mutations and microsatellite instability in solid malignant neoplasms. The full list of 468 genes analyzed by the MSK-IMPACT™ assay is shown in Table 14. See Evaluation of Automatic Class III Designation for MSK-IMPACT (Integrated Mutation Profiling of Actionable Cancer Targets): Decision Summary, United States Food and Drug Administration, Nov. 15, 2017, available at accessdata.fda.gov.

TABLE 14

Genes analyzed by the MSK-IMPACT ™ assay.

| | | | | | | | | | |
|---|---|---|---|---|---|---|---|---|---|
| ABL1 | CALR | DDR2 | FGF19 | HIST3H3 | LYN | NKX2-1 | PPARG | RPTOR | STK19 |
| ACVR1 | CARD11 | DICER1 | FGF3 | HLA-A | MALT1 | NKX3-1 | PPM1D | RRAGC | STK40 |
| AGO2 | CARM1 | DIS3 | FGF4 | HLA-B | MAP2K1 | NOTCH1 | PPP2R1A | RRAS | SUFU |
| AKT1 | CASP8 | DNAJB1 | FGFR1 | HNF1A | MAP2K2 | NOTCH2 | PPP4R2 | RRAS2 | SUZ12 |
| AKT2 | CBFB | DNMT1 | FGFR2 | HOXB13 | MAP2K4 | NOTCH3 | PPP6C | RTEL1 | SYK |
| AKT3 | CBL | DNMT3A | FGFR3 | HRAS | MAP3K1 | NOTCH4 | PRDM1 | RUNX1 | TAP1 |
| ALK | CCND1 | DNMT3B | FGFR4 | ICOSLG | MAP3K13 | NPM1 | PRDM14 | RXRA | TAP2 |
| ALOX12B | CCND2 | DOT1L | FH | ID3 | MAP3K14 | NRAS | PREX2 | RYBP | TBX3 |
| AMER1 | CCND3 | DROSHA | FLCN | IDH1 | MAPK1 | NSD1 | PRKAR1A | SDHA | TCEB1 |
| ANKRD11 | CCNE1 | DUSP4 | FLT1 | IDH2 | MAPK3 | NTHL1 | PRKCI | SDHAF2 | TCF3 |
| APC | CD274 | E2F3 | FLT3 | IFNGR1 | MAPKAP1 | NTRK1 | PRKD1 | SDHB | TCF7L2 |
| AR | CD276 | EED | FLT4 | IGF1 | MAX | NTRK2 | PTCH1 | SDHC | TEK |
| ARAF | CD79A | EGFL7 | FOXA1 | IGF1R | MCL1 | NTRK3 | PTEN | SDHD | TERT |
| ARID1A | CD79B | EGFR | FOXL2 | IGF2 | MDC1 | NUF2 | PTP4A1 | SESN1 | TET1 |
| ARID1B | CDC42 | EIF1AX | FOXO1 | IKBKE | MDM2 | NUP93 | PTPN11 | SESN2 | TET2 |
| ARID2 | CDC73 | EIF4A2 | FOXP1 | IKZF1 | MDM4 | PAK1 | PTPRD | SESN3 | TGFBR1 |

TABLE 14-continued

Genes analyzed by the MSK-IMPACT™ assay.

| | | | | | | | | | |
|---|---|---|---|---|---|---|---|---|---|
| ARID5B | CDH1 | EIF4E | FUBP1 | IL10 | MED12 | PAK7 | PTPRS | SETD2 | TGFBR2 |
| ASXL1 | CDK12 | ELF3 | FYN | IL7R | MEF2B | PALB2 | PTPRT | SETD8 | TMEM127 |
| ASXL2 | CDK4 | EP300 | GATA1 | INHA | MEN1 | PARK2 | RAB35 | SF3B1 | TMPRSS2 |
| ATM | CDK6 | EPAS1 | GATA2 | INHBA | MET | PARP1 | RAC1 | SH2B3 | TNFAIP3 |
| ATR | CDK8 | EPCAM | GATA3 | INPP4A | MGA | PAX5 | RAC2 | SH2D1A | TNFRSF14 |
| ATRX | CDKN1A | EPHA3 | GLI1 | INPP4B | MITF | PBRM1 | RAD21 | SHOC2 | TOP1 |
| AURKA | CDKN1B | EPHA5 | GNA11 | INPPL1 | MLH1 | PDCD1 | RAD50 | SHQ1 | TP53 |
| AURKB | CDKN2A p14ARF | EPHA7 | GNAQ | INSR | MPL | PDCD1LG2 | RAD51 | SLX4 | TP53BP1 |
| AXIN1 | CDKN2A p16INK4A | EPHB1 | GNAS | IRF4 | MRE11A | PDGFRA | RAD51B | SMAD2 | TP63 |
| AXIN2 | CDKN2B | ERBB2 | GPS2 | IRS1 | MSH2 | PDGFRB | RAD51C | SMAD3 | TRAF2 |
| AXL | CDKN2C | ERBB3 | GREM1 | IRS2 | MSH3 | PDPK1 | RAD51D | SMAD4 | TRAF7 |
| B2M | CEBPA | ERBB4 | GRIN2A | JAK1 | MSH6 | PGR | RAD52 | SMARCA4 | TSC1 |
| BABAM1 | CENPA | ERCC2 | GSK3B | JAK2 | MSI1 | PHOX2B | RAD54L | SMARCB1 | TSC2 |
| BAP1 | CHEK1 | ERCC3 | H3F3A | JAK3 | MSI2 | PIK3C2G | RAF1 | SMARCD1 | TSHR |
| BARD1 | CHEK2 | ERCC4 | H3F3B | JUN | MST1 | PIK3C3 | RARA | SMO | U2AF1 |
| BBC3 | CIC | ERCC5 | H3F3C | KDM5A | MST1R | PIK3CA | RASA1 | SMYD3 | UPF1 |
| BCL10 | CREBBP | ERF | HGF | KDM5C | MTOR | PIK3CB | RB1 | SOCS1 | VEGFA |
| BCL2 | CRKL | ERG | HIST1H1C | KDM6A | MUTYH | PIK3CD | RBM10 | SOS1 | VHL |
| BCL2L1 | CRLF2 | ERRFI1 | HIST1H2BD | KDR | MYC | PIK3CG | RECQL | SOX17 | VTCN1 |
| BCL2L11 | CSDE1 | ESR1 | HIST1H3A | KEAP1 | MYCL1 | PIK3R1 | RECQL4 | SOX2 | WHSC1 |
| BCL6 | CSF1R | ETV1 | HIST1H3B | KIT | MYCN | PIK3R2 | REL | SOX9 | WHSC1L1 |
| BCOR | CSF3R | ETV6 | HIST1H3C | KLF4 | MYD88 | PIK3R3 | RET | SPEN | WT1 |
| BIRC3 | CTCF | EZH1 | HIST1H3D | KMT2A | MYOD1 | PIM1 | RFWD2 | SPOP | WWTR1 |
| BLM | CTLA-4 | EZH2 | HIST1H3E | KMT2B | NBN | PLCG2 | RHEB | SPRED1 | XIAP |
| BMPR1A | CTNNB1 | FAM175A | HIST1H3F | KMT2C | NCOA3 | PLK2 | RHOA | SRC | XPO1 |
| BRAF | CUL3 | FAM46C | HIST1H3G | KMT2D | NCOR1 | PMAIP1 | RICTOR | SRSF2 | XRCC2 |
| BRCA1 | CXCR4 | FAM58A | HIST1H3H | KNSTRN | NEGR1 | PMS1 | RIT1 | STAG2 | YAP1 |
| BRCA2 | CYLD | FANCA | HIST1H3I | KRAS | NF1 | PMS2 | RNF43 | STAT3 | YES1 |
| BRD4 | CYSLTR2 | FANCC | HIST1H3J | LATS1 | NF2 | PNRC1 | ROS1 | STAT5A | ZFHX3 |
| BRIP1 | DAXX | FAT1 | HIST2H3C | LATS2 | NFE2L2 | POLD1 | RPS6KA4 | STAT5B | |
| BTK | DCUN1D1 | FBXW7 | HIST2H3D | LMO1 | NFKBIA | POLE | RPS6KB2 | STK11 | |
| ABL1 | CALR | DDR2 | FGF19 | HIST3H3 | LYN | NKX2-1 | PPARG | RPTOR | STK19 |

NEOGENOMICS® NEOTYPE™ Assays

In some embodiments, TMB is determined using a NEOGENOMICS® NEOTYPE™ assay. In some embodiments, the TMB is determined using a NEOTYPE™ Discovery Profile. In some embodiments, the TMB is determined using a NEOTYPE Solid Tumor Profile. The NEOGENOMICS assays measure the number of non-synonymous DNA coding sequence changes per megabase of sequenced DNA.

ONCOMINE™ Tumor Mutation Load Assay

In some embodiments, TMB is determined using a THERMOFISHER SCIENTIFIC® ONCOMINE™ Tumor Mutation assay. In some embodiments, TMB is determined using a THERMOFISHER SCIENTIFIC® ION TORRENT™ ONCOMINE™ Tumor Mutation assay. The ION TORRENT™ ONCOMINE™ Tumor Mutation assay is a targeted NGS assay that quantitates somatic mutations to determine tumor mutation load. The assay covers 1.7 Mb of DNA.

NOVOGENE™ NOVOPM™ Assay

In some embodiments, TMB is determined using a NOVOGENE™ NOVOPM™ assay. In some embodiments, TMB is determined using a NOVOGENE™ NOVOPM™ Cancer Panel assay. The NOVOGENE™ NOVOPM™ Cancer Panel assay is a comprehensive NGS cancer panel that analyzes the complete coding regions of 548 genes and the introns of 21 genes, representing about 1.5 Mb of DNA, and that are relevant for the diagnosis and/or treatment of solid tumors according to the National Comprehensive Cancer Network (NCCN) guidelines and medical literature. The assay detects SNV, InDel, fusion, and copy number variation (CNV) genomic abnormalities.

Other TMB Assays

In some embodiments, TMB is determined using a TMB assay provided by CARIS® Life Sciences. In some embodiments, TMB is determined using the PESONALIS® ACE ImmunoID assay. In some embodiments, TMB is determined using the PGDX® CANCERXOME™-R assay.

In yet another particular embodiment, the genomic profiling detects all mutation types, i.e., single nucleotide variants, insertions/deletions (indels), copy number variations, and rearrangements, e.g., translocations, expression, and epigenetic markers.

Comprehensive gene panels often contain predetermined genes selected based on the type of tumor to be analyzed. Accordingly, the genomic profile used to measure TMB status can be selected based on the type of tumor the subject has. In one embodiment, the genomic profile can include a set of genes particular to a solid tumor. In another embodiment, the genomic profile can include a set of genes particular to hematologic malignancies and sarcomas.

In one embodiment, the genomic profile comprises one or more genes selected from the group consisting of ABL1, BRAF, CHEK1, FANCC, GATA3, JAK2, MITF, PDCD1LG2, RBM10, STAT4, ABL2, BRCA1, CHEK2, FANCD2, GATA4, JAK3, MLH1, PDGFRA, RET, STK11, ACVR1B, BRCA2, CIC, FANCE, GATA6, JUN, MPL, PDGFRB, RICTOR, SUFU, AKT1, BRD4, CREBBP, FANCF, GID4 (C17orf39), KAT6A (MYST3), MRE11A, PDK1, RNF43, SYK, AKT2, BRIP1, CRKL, FANCG, GLI1, KDM5A, MSH2, PIK3C2B, ROS1, TAF1, AKT3, BTG1, CRLF2, FANCL, GNA11, KDM5C, MSH6, PIK3CA, RPTOR, TBX3, ALK, BTK, CSF1R, FAS, GNA13, KDM6A, MTOR, PIK3CB, RUNX1, TERC, AMER1 (FAM123B), C11orf30 (EMSY), CTCF, FAT1, GNAQ, KDR, MUTYH, PIK3CG, RUNX1T1, TERT (promoter only), APC, CARD11, CTNNA1, FBXW7, GNAS, KEAP1, MYC, PIK3R1, SDHA, TET2, AR, CBFB, CTNNB1, FGF10, GPR124, KEL, MYCL (MYCL1), PIK3R2, SDHB, TGFBR2, ARAF, CBL, CUL3, FGF14, GRIN2A, KIT, MYCN, PLCG2, SDHC, TNFAIP3, ARFRP1, CCND1, CYLD, FGF19, GRM3, KLHL6, MYD88, PMS2, SDHD, TNFRSF14, ARID1A, CCND2, DAXX, FGF23, GSK3B, KMT2A (MLL), NF1, POLD1, SETD2, TOP1, ARID1B, CCND3, DDR2, FGF3, H3F3A, KMT2C (MLL3), NF2, POLE, SF3B1, TOP2A, ARID2, CCNE1, DICER1, FGF4, HGF, KMT2D (MLL2), NFE2L2, PPP2R1A, SLIT2, TP53, ASXL1, CD274, DNMT3A, FGF6, HNF1A, KRAS, NFKBIA, PRDM1, SMAD2, TSC1, ATM, CD79A, DOT1L, FGFR1, HRAS, LMO1, NKX2-1, PREX2, SMAD3, TSC2, ATR, CD79B, EGFR, FGFR2, HSD3B1, LRP1B, NOTCH1, PRKAR1A, SMAD4, TSHR, ATRX, CDC73, EP300, FGFR3, HSP90AA1, LYN, NOTCH2, PRKCI, SMARCA4, U2AF1, AURKA, CDH1, EPHA3, FGFR4, IDH1, LZTR1, NOTCH3, PRKDC, SMARCB1, VEGFA, AURKB, CDK12, EPHA5, FH, IDH2, MAGI2, NPM1, PRSS8, SMO, VHL, AXIN1, CDK4, EPHA7, FLCN, IGF1R, MAP2K1, NRAS, PTCH1, SNCAIP, WISP3, AXL, CDK6, EPHB1, FLT1, IGF2, MAP2K2, NSD1, PTEN, SOCS1, WT1, BAP1, CDK8, ERBB2, FLT3, IKBKE, MAP2K4, NTRK1, PTPN11, SOX10, XPO1, BARD1, CDKN1A, ERBB3, FLT4, IKZF1, MAP3K1, NTRK2, QKI, SOX2, ZBTB2, BCL2, CDKN1B, ERBB4, FOXL2, IL7R, MCL1, NTRK3, RAC1, SOX9, ZNF217, BCL2L1, CDKN2A, ERG, FOXP1, INHBA, MDM2, NUP93, RAD50, SPEN, ZNF703, BCL2L2, CDKN2B, ERRFI1, FRS2, INPP4B, MDM4, PAK3, RAD51, SPOP, BCL6, CDKN2C, ESR1, FUBP1, IRF2, MED12, PALB2, RAF1, SPTA1, BCOR, CEBPA, EZH2, GABRA6, IRF4, MEF2B, PARK2, RANBP2, SRC, BCORL1, CHD2, FAM46C, GATA1, IRS2, MEN1, PAX5, RARA, STAG2, BLM, CHD4, FANCA, GATA2, JAK1, MET, PBRM1, RB1, STAT3, and any combination thereof. In other embodiments, the TMB analysis further comprises identifying a genomic alteration in one or more of ETV4, TMPRSS2, ETV5, BCR, ETV1, ETV6, and MYB.

In another embodiment, the genomic profile comprises one or more genes selected from the group consisting of ABL1, 12B, ABL2, ACTB, ACVR1, ACVR1B, AGO2, AKT1, AKT2, AKT3, ALK, ALOX, ALOX12B, AMER1, AMER1 (FAM123B or WTX), AMER1 (FAM123B), ANKRD11, APC, APH1A, AR, ARAF, ARFRP1, ARHGAP26 (GRAF), ARID1A, ARID1B, ARID2, ARID5B, ARv7, ASMTL, ASXL1, ASXL2, ATM, ATR, ATRX AURKA, AURKB, AXIN1, AXIN2, AXL, B2M, BABAM1, BAP1, BARD1, BBC3, BCL10, BCL11B, BCL2, BCL2L1, BCL2L11, BCL2L2, BCL6, BCL7A, BCOR, BCORL1, BIRC3, BLM, BMPR1A, BRAF, BRCA1, BRCA2, BRD4, BRIP1, BRIP1 (BACH1), BRSK1, BTG1, BTG2, BTK, BTLA, C11orf 30 (EMSY), C11orf30, C11orf30 (EMSY), CAD, CALR, CARD11, CARMI, CASP8, CBFB, CBL, CCND1, CCND2, CCND3, CCNE1, CCT6B, CD22, CD274, CD274 (PD-L1), CD276, CD36, CD58, CD70, CD79A, CD79B, CDC42, CDC73, CDH1, CDK12, CDK4, CDK6, CDK8, CDKN1A, CDKN1B, CDKN2A, CDKN2Ap14ARF, CDKN2Ap16INK4A, CDKN2B, CDKN2C, CEBPA, CENPA, CHD2, CHD4, CHEK1, CHEK2, CIC, CIITA, CKS1B, CPS1, CREBBP, CRKL, CRLF2, CSDE1, CSF1R, CSF3R, CTCF, CTLA-4, CTNN B1, CTNNA1, CTNNB1, CUL3, CUL4A, CUX1, CXCR4, CYLD, CYP17A1, CYSLTR2, DAXX, DCUN1D1, DDR1, DDR2, DDX3X, DH2, DICER1, DIS3, DNAJB1, DNM2, DNMT1, DNMT3A, DNMT3B, DOT1L, DROSHA, DTX1, DUSP2, DUSP4, DUSP9, E2F3, EBF1, ECT2L, EED, EGFL7, EGFR, EIF1AX, EIF4A2, EIF4E, ELF3, ELP2, EML4, EML4-ALK, EP300, EPAS1, EPCAM, EPHA3, EPHA5, EPHA7, EPHB1, EPHB4, ERBB2, ERBB3, ERBB4, ERCC1, ERCC2, ERCC3, ERCC4, ERCC5, ERF, ERG, ERRFI1, ERRFl1, ESR1, ETS1, ETV1, ETV4, ETV5, ETV6, EWSR1, EXOSC6, EZH1, EZH2, FAF1, FAM175A, FAM46C, FAM58A, FANCA, FANCC, FANCD2, FANCE, FANCF, FANCG, FANCI, FANCL, FAS, FAS (TNFRSF6), FAT1, FBXO11, FBXO31, FBXW7, FGF1, FGF10, FGF12, FGF14, FGF19, FGF2, FGF23, FGF3, FGF4, FGF5, FGF6, FGF7, FGF8, FGF9, FGFR1, FGFR2, FGFR3, FGFR4, FH, FHIT, FLCN, FLI1, FLT1, FLT3, FLT4, FLYWCH1, FOXA1, FOXL2, FOXO1, FOXO3, FOXP1, FRS2, FUBP1, FYN, GABRA6, GADD45B, GATA1, GATA2, GATA3, GATA4, GATA6, GEN1, GID4 (C17orf 39), GID4 (C17orf39), GLI1, GLI1, GNA11, GNA12, GNA13, GNAQ, GNAS, GPR124, GPS2, GREM1, GRIN2A, GRM3, GSK3B, GTSE1, H3F3A, H3F3B, H3F3C, HDAC1, HDAC4, HDAC7, Hedgehog, HER-2/NEU, ERBB2, HGF, HIST1H1C, HIST1H1D, HIST1H1E, HIST1H2AC, HIST1H2AG, HIST1H2AL, HIST1H2AM HIST1H2BC, HIST1H2BD, HIST1H2BJ, HIST1H2BK, HIST1H2BO, HIST1H3A, HIST1H3B, HIST1H3C, HIST1H3D, HIST1H3E, HIST1H3F, HIST1H3G, HIST1H3H. HIST1H3I, HIST1H3J, HIST2H3C, HIST2H3D, HIST3H3, HLA-A, HLA-B, HNFA, HOXB13, HRAS, HSD3B1, HSP90AA1, ICK, ICOSLG, ID3, IDH1, IDH2, IFNGR1, IGF1, IGF1R, IGF2, IKBKE, IKZF1, IKZF2, IKZF3, IL10, IL7R, INHA, INHBA, INPP4A, INPP4B, INPP5D (SHIP), INPPL1, INSR, IRF1, IRF2, IRF4, IRF8, IRS1, IRS2, JAK1, JAK2, JAK3, JARID2, JUN, K14, KAT6A (MYST 3), KAT6A (MYST3), KDM2B, KDM4C, KDM5A, KDM5C, KDM6A, KDR, KEAP1, KEL, KIF5B, KIT, KLF4, KLHL6, KMT2A, KMT2A (MLL), KMT2B, KMT2C, KMT2C (MLL3), KMT2D, KMT2D (MLL2), KNSTRN, KRAS, LAMP1, LATS1, LATS2, LEF1, LMO1, LRP1B, LRRK2, LTK, LYN, LZTR1, MAF, MAFB, MAGED1, MAGI2, MALT1, MAP2K1, MAP2K1 (MEK1), MAP2K2, MAP2K2 (MEK2), MAP2K4, MAP3, MAP3K1, MAP3K13, MAP3K14, MAP3K6, MAP3K7, MAPK1, MAPK3, MAPKAP1, MAX, MCL1, MDC1, MDM2, MDM4, MED12, MEF2B, MEF2C, MEK1, MEN1, MERTK, MET, MGA, MIB1, MITF, MKI67, MKNK1, MLH1, MLLT3, MPL, MRE 11A, MRE11A, MSH2, MSH3, MSH6, MSI1, MSI2, MST1, MST1R, MTAP, MTOR, MUTYH, MYC, MYCL, MYCL (MYC L1), MYCL (MYCL1), MYCL1, MYCN, MYD88, MYO18A, MYOD1, NBN, NCOA3, NCOR1, NCOR2, NCSTN, NEGR1, NF1, NF2, NFE2L2, NFKBIA, NKX2-1, NKX3-1, NOD1, NOTCH1, NOTCH2, NOTCH3, NOTCH4, NPM1, NRAS, NRG1, NSD1, NT5C2, NTHL1, NTRK1, NTRK2, NTRK3, NUF2, NUP93, NUP98, P2RY8, PAG1, PAK1, PAK3, PAK7, PALB2, PARK2, PARP1, PARP2, PARP3, PASK, PAX3, PAX5, PAX7, PBRM1, PC, PCBP1, PCLO, PDCD1, PDCD1 (PD-1), PDCD11, PDCD1LG2, PDCD1LG2 (PD-L2), PDGFRA, PDGFRB, PDK1, PDPK1, PGR, PHF6, PHOX2B, PIK3C2B, PIK3C2G, PIK3C3, PIK3CA, PIK3CB, PIK3CD, PIK3CG, PIK3R1, PIK3R2, PIK3R3, PIM1, PLCG2, PLK2, PMAIP1, PMS1, PMS2, PNRC1, POLD1, POLE, POT1, PPARG, PPM1D, PPP2, PPP2R1A, PPP2R2A, PPP4R2, PPP6C, PRDM1, PRDM14, PREX2, PRKAR1A, PRKCI, PRKD1, PRKDC, PRSS8, PTCH1, PTEN, PTP4A1, PTPN11, PTPN2, PTPN6 (SHP-1), PTPRD, PTPRO, PTPRS, PTPRT, QKI, R1A, RAB35, RAC1, RAC2, RAD21, RAD50, RAD51, RAD51B, RAD51C, RAD51D, RAD52, RAD54L, RAF1, RANBP2, RARA, RASA1, RASGEF1A, RB1, RBM10, RECQL, RECQL4, REL, RELN, RET, RFWD2, RHEB, RHOA, RICTOR, RIT1, RNF43, ROS1, RPS6KA4, RPS6KBL, RPS6KB2, RPTOR, RRAGC, RRAS, RRAS2, RTEL1, RUNX1, RUNX1T1, RXRA, RYBP, S1PR2, SDHA, SDHAF2, SDHB, SDHC, SDHD, SERP2, SESN1, SESN2, SESN3, SETBP1, SETD2, SETD8, SF3B1, SGK1, SH2B3, SH2D1A, SHOC2, SHQ1, SLIT2, SLX4, SMAD2, SMAD3, SMAD4, SMARCA1, SMARCA4, SMARCB1, SMARCD1, SMC1A, SMC3, SMO, SMYD3, SNCAIP, SOCS1, SOCS2, SOCS3, SOS1, SOX10, SOX17, SOX2, SOX9, SPEN, SPOP, SPRED1, SPTA1, SRC, SRSF2, STAG2, STAT3, STAT4, STAT5A, STAT5B, STAT6, STK11, STK19, STK40, SUFU, SUZ12, SYK, TAF1, TAP1, TAP2, TBL1XR1, TBX3, TCEB1, TCF3, TCF3 (E2A), TCF7L2, TCL1A (TCL1), TEK, TERC, TERT, TERT Promoter, TET1, TET2, TFRC, TGFBR1, TGFBR2, TIPARP, TLL2, TMEM127, TMEM30A, TMPRSS2, TMSB4XP8 (TMSL3), TNFAIP3, TNFRSF11A, TNFRSF14, TNFRSF17, TOP1, TOP2A, TP53, TP53BP1, TP63, TRAF2, TRAF3, TRAF5, TRAF7. TSC1, TSC2, TSHR, TUSC3, TYK2, TYRO3, U2AF1, U2AF2, UPF1, VEGFA, VHL, VTCN1, WDR90, WHSC1, WHSC1 (MM-SET or NSD2), WHSC1L1, WISP3, WT1, WWTR1, XBP1, XIAP, XPO1, XRCC2, YAP1, YES1, YY1AP1, ZBTB2, ZFHX3, ZMYM3, ZNF217, ZNF24 (ZSCAN3), ZNF703, ZRSR2, and any combination thereof.

In another embodiment, the genomic profiling assay comprises at least about 20, at least about 30, at least about 40, at least about 50, at least about 60, at least about 70, at least about 80, at least about 90, at least about 100, at least about 110, at least about 120, at least about 130, at least about 140, at least about 150, at least about 160, at least about 170, at least about 180, at least about 190, at least about 200, at least about 210, at least about 220, at least about 230, at least about 240, at least about 250, at least about 260, at least about 270, at least about 280, at least about 290, or at least about 300 genes selected from the group consisting of ABL1, 12B, ABL2, ACTB, ACVR1, ACVR1B, AGO2, AKT1, AKT2, AKT3, ALK, ALOX, ALOX12B, AMER1, AMER1 (FAM123B or WTX), AMER1 (FAM123B), ANKRD11, APC, APH1A, AR, ARAF, ARFRP1, ARHGAP26 (GRAF), ARID1A, ARID1B, ARID2, ARID5B, ARv7, ASMTL, ASXL1, ASXL2, ATM, ATR, ATRX, AURKA, AURKB, AXIN1, AXIN2, AML, B2M, BABAM1, BAP1, BARD1, BBC3, BCL10, BCL11B, BCL2, BCL2L1, BCL2L11, BCL2L2, BCL6, BCL7A, BCOR, BCORL1, BIRC3, BLM, BMPR1A, BRAF, BRCA1, BRCA2, BRD4, BRIP1, BRIP1 (BACH1), BRSK1, BTG1, BTG2, BTK, BTLA, C11orf 30 (EMSY), C11orf30, C11orf30 (EMSY), CAD, CALR, CARD11, CARMI, CASP8, CBFB, CBL, CCND1, CCND2, CCND3, CCNE1, CCT6B, CD22, CD274, CD274 (PD-L1), CD276, CD36, CD58, CD70, CD79A, CD79B, CDC42, CDC73, CDH1, CDK12, CDK4, CDK6, CDK8, CDKN1A, CDKN1B, CDKN2A, CDKN2Ap14ARF, CDKN2Ap16INK4A, CDKN2B, CDKN2C, CEBPA, CENPA, CHD2, CHD4, CHEK1, CHEK2, CIC, CIITA, CKS1B, CPS1, CREBBP, CRKL, CRLF2, CSDE1, CSF1R, CSF3R, CTCF, CTLA-4, CTNN B1, CTNNA1, CTNNB1, CUL3, CUL4A, CUX1, CXCR4, CYLD, CYP17AL, CYSLTR2, DAXX, DCUN1D1, DDR1, DDR2, DDX3X DH2, DICER1, DIS3, DNAJB1, DNM2, DNMT1, DNMT3A, DNMT3B, DOT1L, DROSHA, DTX1, DUSP2, DUSP4, DUSP9, E2F3, EBF1, ECT2L, EED, EGFL7, EGFR, EIF1AX, EIF4A2, EIF4E, ELF3, ELP2, EML4, EML4-ALK, EP300, EPAS1, EPCAM EPHA3, EPHA5, EPHA7, EPHB1, EPHB4, ERBB2, ERBB3, ERBB4, ERCC1, ERCC2, ERCC3, ERCC4, ERCC5, ERF, ERG, ERRFI1, ERRFl1, ESR1, ETS1, ETV1, ETV4, ETV5, ETV6, EWSR1, EXOSC6, EZH1, EZH2, FAF1, FAM175A, FAM46C, FAM58A, FANCA, FANCC, FANCD2, FANCE, FANCF, FANCG, FANCI, FANCL, FAS, FAS (TNFRSF6), FAT1, FBXO11, FBXO31, FBXW7, FGF1, FGF10, FGF12, FGF14, FGF19, FGF2, FGF23, FGF3, FGF4, FGF5, FGF6, FGF7, FGF8, FGF9, FGFR1, FGFR2, FGFR3, FGFR4, FH, FHIT, FLCN, FLI1, FLT1, FLT3, FLT4, FLYWCH1, FOXA1, FOXL2, FOXO1, FOXO3, FOXP1, FRS2, FUBP1, FYN, GABRA6, GADD45B, GATA1, GATA2, GATA3, GATA4, GATA6, GEN1, GID4 (C17orf 39), GID4 (C17orf39), GLI1, GLl1, GNA11, GNA12, GNA13, GNAQ, GNAS, GPR124, GPS2, GREM1, GRIN2A, GRM3, GSK3B, GTSE1, H3F3A, H3F3B, H3F3C, HDAC1, HDAC4, HDAC7, Hedgehog, HER-2/NEU; ERBB2, HGF, HIST1H1C, HIST1H1D, HIST1H1E, HIST1H2AC, HIST1H2AG, HIST1H2AL, HIST1H2AM, HIST1H2BC, HIST1H2BD, HIST1H2BJ, HIST1H2BK, HIST1H2BO, HIST1H3A, HIST1H3B, HIST1H3C, HIST1H3D, HIST1H3E, HIST1H3F, HIST1H3G, HIST1H3H, HIST1H3I, HIST1H3J, HIST2H3C, HIST2H3D, HIST3H3, HLA-A, HLA-B, HNF1A, HOXB13, HRAS, HSD3B1, HSP90AA1, ICK, ICOSLG, ID3, IDH1, IDH2, IFNGR1, IGF1, IGF1R, IGF2, IKBKE, IKZF1, IKZF2, IKZF3, IL10, IL7R, INHA, INHBA, INPP4A, INPP4B, INPP5D (SHIP), INPPL1, INSR, IRF1, IRF2, IRF4, IRF8, IRS1, IRS2, JAK1, JAK2, JAK3, JARID2, JUN, K14, KAT6A (MYST 3), KAT6A (MYST3), KDM2B, KDM4C, KDM5A, KDM5C, KDM6A, KDR, KEAP1, KEL, KIF5B, KIT, KLF4, KLHL6, KMT2A, KMT2A (MLL), KMT2B, KMT2C, KMT2C (MLL3), KMT2D, KMT2D (MLL2), KNSTRN, KRAS, LAMP1, LATS1, LATS2, LEF1, LMO1, LRP1B, LRRK2, LTK, LYN, LZTR1, MAF, MAFB, MAGED1, MAGI2, MALT1, MAP2K1, MAP2K1 (MEK1), MAP2K2, MAP2K2 (MEK2), MAP2K4, MAP3, MAP3K1, MAP3K13, MAP3K14, MAP3K6, MAP3K7, MAPK1, MAPK3, MAPKAP1, MAX, MCL1, MDC1, MDM2, MDM4, MED12, MEF2B, MEF2C, MEK1, MEN1, MERTK, MET, MGA, MIB1, MITF, MKI67, MKNK1, MLH1, MLLT3, MPL, MRE HA, MRE11A, MSH2, MSH3, MSH6, MSI1, MSI2, MST1, MST1R, MTAP, MTOR, MUTYH, MYC, MYCL, MYCL (MYC L1), MYCL (MYCL1), MYCL1, MYCN, MYD88, MYO18A, MYOD1, NBN, NCOA3, NCOR1, NCOR2, NCSTN, NEGR1, NF1, NF2, NFE2L2, NFKBIA, NKX2-1, NKX3-1, NOD1, NOTCH1, NOTCH2, NOTCH3, NOTCH4, NPM1, NRAS, NRG1, NSD1, NT5C2, NTHL1, NTRK1, NTRK2, NTRK3, NUF2, NUP93, NUP98, P2RY8, PAG1, PAK1, PAK3, PAK7, PALB2, PARK2, PARP1, PARP2, PARP3, PASK, PAX3, PAX5, PAX7, PBRM1, PC, PCBP1, PCLO, PDCD1, PDCD1 (PD-1), PDCD11, PDCD1LG2, PDCD1LG2 (PD-L2), PDGFRA, PDGFRB, PDK1, PDPK1, PGR, PHF6, PHOX2B, PIK3C2B, PIK3C2G, PIK3C3, PIK3CA, PIK3CB, PIK3CD, PIK3CG, PIK3R1, PIK3R2, PIK3R3, PIM1, PLCG2, PLK2, PMAIP1, PMS1, PMS2, PNRC1, POLD1, POLE, POT1, PPARG, PPM1D, PPP2, PPP2R1A, PPP2R2A, PPP4R2, PPP6C, PRDM1, PRDM14, PREX2, PRKAR1A, PRKCI, PRKD1, PRKDC, PRSS8, PTCH1, PTEN, PTP4AL, PTPN11, PTPN2, PTPN6 (SHP-1), PTPRD, PTPRO, PTPRS, PTPRT, QKI, R1A, RAB35, RAC1, RAC2, RAD21, RAD50, RAD51, RAD51B, RAD51C, RAD51D, RAD52, RAD54L, RAF1, RANBP2, RARA, RASA1, RASGEF1A, RB1, RBM10, RECQL, RECQL4, REL, RELN, RET, RFWD2, RHEB, RHOA, RICTOR, RIT1, RNF43, ROS1, RPS6KA4, RPS6 KB1, RPS6KB2, RPTOR, RRAGC, RRAS, RRAS2, RTEL1, RUNX1, RUNX1T1, RXRA, RYBP, S1PR2, SDHA, SDHAF2, SDHB, SDHC, SDHD, SERP2, SESN1, SESN2, SESN3, SETBP1, SETD2, SETD8, SF3B1, SGK1, SH2B3, SH2D1A, SHOC2, SHQ1, SLIT2, SLX4, SMAD2, SMAD3, SMAD4, SMARCA1, SMARCA4, SMARCB1, SMARCD1, SMC1A, SMC3, SMO, SMYD3, SNCAIP, SOCS1, SOCS2, SOCS3, SOS1, SOX10, SOX17, SOX2, SOX9, SPEN, SPOP, SPRED1, SPTA1, SRC, SRSF2, STAG2, STAT3, STAT4, STAT5A, STAT5B, STAT6, STK11, STK19, STK40, SUFU, SUZ12, SYK, TAF1, TAP1, TAP2, TBL1XR1, TBX3, TCEB1, TCF3, TCF3 (E2A), TCF7L2, TCL1A (TCL1), TEK, TERC, TERT, TERT Promoter, TET1, TET2, TFRC, TGFBR1, TGFBR2, TIPARP, TLL2, TMEM127, TMEM30A, TMPRSS2, TMSB4XP8 (TMSL3), TNFAIP3, TNFRSF11A, TNFRSF4, TNFRSF7, TOP1, TOP2A, TP53, TP53BP1, TP63, TRAF2, TRAF3, TRAF5, TRAF7, TSC1, TSC2, TSHR, TUSC3, TYK2, TYRO3, U2AF1, U2AF2, UPF1, VEGFA, VHL, VTCN1, WDR90, WHSC1, WHSC1 (MM-SET or NSD2), WHSC1L1, WISP3, WT1, WWTR1, XBP1, XIAP, XPO1, XRCC2, YAP1, YES1, YY1AP1, ZBTB2, ZFHX3, ZMYM3, ZNF217, ZNF24 (ZSCAN3), ZNF703, ZRSR2, and any combination thereof.

In another embodiment, the genomic profile comprises one or more genes selected from the genes listed in Tables 2-14.

In one embodiment, TMB status based on genomic profiling is highly correlated with TMB status based on whole-exome or whole-genome sequencing. Evidence shows that the use of genomic profiling assays, such as the F1CDx assay, have concordance with whole-exome and/or whole genome sequencing assays. These data support the use of genomic profiling assays as a more efficient means of measuring TMB status, without forfeiting the prognostic qualities of TMB status.

TMB can be measured using a tissue biopsy sample or, alternatively, circulating tumor DNA (ctDNA), cfDNA (cell-free DNA), and/or a liquid biopsy sample. ctDNA can be used to measure TMB status according to whole-exome or whole-genome sequencing or genomic profiling using available methodologies, e.g., GRAIL, Inc.

A subject afflicted with a tumor derived from an SCLC is identified as suitable for a therapy with an anti-PD-1 antibody monotherapy or an anti-PD-1/anti-CTLA-4 combination therapy based on the measurement of TMB status and identification of a high TMB. In some embodiments, a TMB score is calculated as the total number of nonsynonymous missense mutations in a tumor, as measured by whole exome sequencing or whole genome sequencing. In one embodiment, the high TMB has a score of at least 210, at least 215, at least 220, at least 225, at least 230, at least 235, at least 240, at least 245, at least 250, at least 255, at least 260, at least 265, at least 270, at least 275, at least 280, at least 285, at least 290, at least 295, at least 300, at least 305, at least 310, at least 315, at least 320, at least 325, at least 330, at least 335, at least 340, at least 345, at least 350, at least 355, at least 360, at least 365, at least 370, at least 375, at least 380, at least 385, at least 390, at least 395, at least 400, at least 405, at least 410, at least 415, at least 420, at least 425, at least 430, at least 435, at least 440, at least 445, at least 450, at least 455, at least 460, at least 465, at least 470, at least 475, at least 480, at least 485, at least 490, at least 495, or at least 500. In another embodiment, the high TMB has a score of at least 215, at least 220, at least 221, at least 222, at least 223, at least 224, at least 225, at least 226, at least 227, at least 228, at least 229, at least 230, at least 231, at least 232, at least 233, at least 234, at least 235, at least 236, at least 237, at least 238, at least 239, at least 240, at least 241, at least 242, at least 243, at least 244, at least 245, at least 246, at least 247, at least 248, at least 249, or at least 250. In a particular embodiment, the high TMB has a score of at least 243. In other embodiments, the high TMB has a score of at least 244. In some embodiments, the high TMB has a score of at least 245. In other embodiments, the high TMB has a score of at least 246. In other embodiments, the high TMB has a score of at least 247. In other embodiments, the high TMB has a score of at least 248. In other embodiments, the high TMB has a score of at least 249. In other embodiments, the high TMB has a score of at least 250. In other embodiments, the high TMB has a score of any integer between 200 and 300 or higher. In other embodiments, the high TMB has a score of any integer between 210 and 290 or higher. In other embodiments, the high TMB has a score of any integer between 220 and 280 or higher. In other embodiments, the high TMB has a score of any integer between 230 and 270 or higher. In other embodiments, the high TMB has a score of any integer between 235 and 265 or higher.

Alternatively, the high TMB can be a relative value rather than an absolute value. In some embodiments, the subject's TMB status is compared to a reference TMB value. In one embodiment, the subject's TMB status is within the highest fractile of the reference TMB value. In another embodiment, the subject's TMB status is within the top tertile of the reference TMB value.

In some embodiments, TMB status is expressed as the number of mutations per sample, per cell, per exome, or per length of DNA (e.g., Mb). In some embodiments, a tumor has a high TMB status if the tumor has at least about 50 mutations/tumor, at least about 55 mutations/tumor, at least about 60 mutations/tumor, at least about 65 mutations/tumor, at least about 70 mutations/tumor, at least about 75 mutations/tumor, at least about 80 mutations/tumor, at least about 85 mutations/tumor, at least about 90 mutations/tumor, at least about 95 mutations/tumor, at least about 100 mutations/tumor, at least about 105 mutations/tumor, at least about 110 mutations/tumor, at least about 115 mutations/tumor, or at least about 120 mutations/tumor. In some embodiments, a tumor has a high TMB status if the tumor has at least about 125 mutations/tumor, at least about 150 mutations/tumor, at least about 175 mutations/tumor, at least about 200 mutations/tumor, at least about 225 mutations/tumor, at least about 250 mutations/tumor, at least about 275 mutations/tumor, at least about 300 mutations/tumor, at least about 350 mutations/tumor, at least about 400 mutations/tumor, or at least about 500 mutations/tumor. In one particular embodiment, a tumor has a high TMB status if the tumor has at least about 100 mutations/tumor.

In some embodiments, a tumor has a high TMB status if the tumor has at least about 5 mutations per megabase of genes, e.g., genome sequenced according to a TMB assay, e.g., genome sequenced according to a FOUNDATION-ONE® CDX™ assay, (mutations/Mb), at least about 6 mutations/Mb, at least about 7 mutations/Mb, at least about 8 mutations/Mb, at least about 9 mutations/Mb, at least about 10 mutations/Mb, at least about 11 mutations/Mb, at least about 12 mutations/Mb, at least about 13 mutations/Mb, at least about 14 mutations/Mb, at least about 15 mutations/Mb, at least about 20 mutations/Mb, at least about 25 mutations/Mb, at least about 30 mutations/Mb, at least about 35 mutations/Mb, at least about 40 mutations/Mb, at least about 45 mutations/Mb, at least about 50 mutations/Mb, at least about 75 mutations/Mb, or at least about 100 mutations/Mb. In certain embodiments, a tumor has a high TMB status if the tumor has at least about 5 mutations/Mb. In certain embodiments, a tumor has a high TMB status if the tumor has at least about 10 mutations/Mb. In some embodiments, a tumor has a high TMB status if the tumor has at least about 11 mutations/Mb. In some embodiments, a tumor has a high TMB status if the tumor has at least about 12 mutations/Mb. In some embodiments, a tumor has a high TMB status if the tumor has at least about 13 mutations/Mb. In some embodiments, a tumor has a high TMB status if the tumor has at least about 14 mutations/Mb. In certain embodiments, a tumor has a high TMB status if the tumor has at least about 15 mutations/Mb.

Because the number of mutations varies by tumor type and other ways (see Q4 and Q5), the values associated with "TMB high" and "TMB low" can differ across tumor types.

PD-L1 Status

TMB status can be used alone or in combination with other factors as a means to predict a tumor's response to therapy and, in particular, treatment with an immuno-oncology agent, such as an anti-PD-1 antibody or an anti-CTLA-4 antibody. In some embodiments, only the TMB status of a tumor is used to identify patients with a tumor more likely to respond to therapy with an anti-PD-1 antibody monotherapy or an anti-PD-1/anti-CTLA-4 antibody combination therapy. In other embodiments, the PD-L1 status and TMB status are used to identify patients with a tumor more likely to respond to therapy with an anti-PD-1 antibody monotherapy or an anti-PD-1/anti-CTLA-4 antibody combination therapy.

The PD-L1 status of a tumor in a subject can be measured prior to administering any composition or utilizing any method disclosed herein. PD-L1 expression can be determined by any methods known in the art.

In order to assess the PD-L1 expression, in one embodiment, a test tissue sample can be obtained from the patient who is in need of the therapy. In another embodiment, the assessment of PD-L1 expression can be achieved without obtaining a test tissue sample. In some embodiments, selecting a suitable patient includes (i) optionally providing a test tissue sample obtained from a patient with cancer of the tissue, the test tissue sample comprising tumor cells and/or tumor-infiltrating inflammatory cells; and (ii) assessing the proportion of cells in the test tissue sample that express PD-L1 on the surface of the cells based on an assessment that the proportion of cells in the test tissue sample that express PD-L1 on the cell surface is higher than a predetermined threshold level.

In any of the methods comprising the measurement of PD-L1 expression in a test tissue sample, however, it should be understood that the step comprising the provision of a test tissue sample obtained from a patient is an optional step. It should also be understood that in certain embodiments the "measuring" or "assessing" step to identify, or determine the number or proportion of, cells in the test tissue sample that express PD-L1 on the cell surface is performed by a transformative method of assaying for PD-L1 expression, for example by performing a reverse transcriptase-polymerase chain reaction (RT-PCR) assay or an IHC assay. In certain other embodiments, no transformative step is involved and PD-L1 expression is assessed by, for example, reviewing a report of test results from a laboratory. In certain embodiments, the steps of the methods up to, and including, assessing PD-L1 expression provides an intermediate result that can be provided to a physician or other healthcare provider for use in selecting a suitable candidate for the anti-PD-1 antibody or anti-PD-L1 antibody therapy. In certain embodiments, the steps that provide the intermediate result is performed by a medical practitioner or someone acting under the direction of a medical practitioner. In other embodiments, these steps are performed by an independent laboratory or by an independent person such as a laboratory technician.

In certain embodiments of any of the present methods, the proportion of cells that express PD-L1 is assessed by performing an assay to determine the presence of PD-L1 RNA. In further embodiments, the presence of PD-L1 RNA is determined by RT-PCR, in situ hybridization or RNase protection. In other embodiments, the proportion of cells that express PD-L1 is assessed by performing an assay to determine the presence of PD-L1 polypeptide. In further embodiments, the presence of PD-L1 polypeptide is determined by immunohistochemistry (IHC), enzyme-linked immunosorbent assay (ELISA), in vivo imaging, or flow cytometry. In some embodiments, PD-L1 expression is assayed by IHC. In other embodiments of all of these methods, cell surface expression of PD-L1 is assayed using, e.g., IHC or in vivo imaging.

Imaging techniques have provided important tools in cancer research and treatment. Recent developments in molecular imaging systems, including positron emission tomography (PET), single-photon emission computed tomography (SPECT), fluorescence reflectance imaging (FRI), fluorescence-mediated tomography (FMT), bioluminescence imaging (BLI), laser-scanning confocal microscopy (LSCM) and multiphoton microscopy (MPM), will likely herald even greater use of these techniques in cancer research. Some of these molecular imaging systems allow clinicians to not only see where a tumor is located in the body, but also to visualize the expression and activity of specific molecules, cells, and biological processes that influence tumor behavior and/or responsiveness to therapeutic drugs (Condeelis and Weissleder, "In vivo imaging in cancer," *Cold Spring Harb. Perspect. Biol.* 2(12):a003848 (2010)). Antibody specificity, coupled with the sensitivity and resolution of PET, makes immunoPET imaging particularly attractive for monitoring and assaying expression of antigens in tissue samples (McCabe and Wu, "Positive progress in immunoPET—not just a coincidence," *Cancer Biother. Radiopharm.* 25(3):253-61 (2010); Olafsen et al., "ImmunoPET imaging of B-cell lymphoma using 124I-anti-CD20 scFv dimers (diabodies)," *Protein Eng. Des. Sel.* 23(4):243-9 (2010)). In certain embodiments of any of the present methods, PD-L1 expression is assayed by immunoPET imaging. In certain embodiments of any of the present methods, the proportion of cells in a test tissue sample that express PD-L1 is assessed by performing an assay to determine the presence of PD-L1 polypeptide on the surface of cells in the test tissue sample. In certain embodiments, the test tissue sample is a FFPE tissue sample. In other embodiments, the presence of PD-L1 polypeptide is determined by IHC assay. In further embodiments, the IHC assay is performed using an automated process. In some embodiments, the IHC assay is performed using an anti-PD-L1 monoclonal antibody to bind to the PD-L1 polypeptide. In certain embodiments, the anti-PD-L1 monoclonal antibody is selected from the group consisting of 28-8, 28-1, 28-12, 29-8, 5H1, and any combination thereof. See WO/2013/173223, which is incorporated by reference herein in its entirety.

In one embodiment of the present methods, an automated IHC method is used to assay the expression of PD-L1 on the surface of cells in FFPE tissue specimens. The presence of human PD-L1 antigen can be measured in a test tissue sample by contacting the test sample, and a negative control sample (e.g., normal tissue), with a monoclonal antibody that specifically binds to human PD-L1, under conditions that allow for formation of a complex between the antibody or portion thereof and human PD-L1. In certain embodiments, the test and control tissue samples are FFPE samples. The formation of a complex is then detected, wherein a difference in complex formation between the test sample and the negative control sample is indicative of the presence of human PD-L1 antigen in the sample. Various methods are used to quantify PD-L1 expression.

In a particular embodiment, the automated IHC method comprises: (a) deparaffinizing and rehydrating mounted tissue sections in an autostainer; (b) retrieving antigen using a decloaking chamber and pH 6 buffer, heated to 110° C. for 10 min; (c) setting up reagents on an autostainer; and (d) running the autostainer to include steps of neutralizing endogenous peroxidase in the tissue specimen; blocking non-specific protein-binding sites on the slides; incubating the slides with primary antibody; incubating with a post primary blocking agent; incubating with NovoLink Polymer; adding a chromogen substrate and developing; and counterstaining with hematoxylin.

For assessing PD-L1 expression in tumor tissue samples, a pathologist examines the number of membrane PD-L1 tumor cells in each field under a microscope and mentally estimates the percentage of cells that are positive, then averages them to come to the final percentage. The different staining intensities are defined as 0/negative, 1+/weak, 2+/moderate, and 3+/strong. Typically, percentage values are first assigned to the 0 and 3+ buckets, and then the intermediate 1+ and 2+ intensities are considered. For highly heterogeneous tissues, the specimen is divided into zones, and each zone is scored separately and then combined into a single set of percentage values. The percentages of negative and positive cells for the different staining intensities are determined from each area and a median value is given to each zone. A final percentage value is given to the tissue for each staining intensity category: negative, 1+, 2+, and 3+. The sum of all staining intensities needs to be 100%. In one embodiment, the threshold number of cells that needs to be PD-L1 positive is at least about 100, at least about 125, at least about 150, at least about 175, or at least about 200 cells. In certain embodiments, the threshold number or cells that needs to be PD-L1 positive is at least about 100 cells.

Staining is also assessed in tumor-infiltrating inflammatory cells such as macrophages and lymphocytes. In most cases macrophages serve as an internal positive control since staining is observed in a large proportion of macrophages. While not required to stain with 3+ intensity, an absence of staining of macrophages should be taken into account to rule out any technical failure. Macrophages and lymphocytes are assessed for plasma membrane staining and only recorded for all samples as being positive or negative for each cell category. Staining is also characterized according to an outside/inside tumor immune cell designation. "Inside" means the immune cell is within the tumor tissue and/or on the boundaries of the tumor region without being physically intercalated among the tumor cells. "Outside" means that there is no physical association with the tumor, the immune cells being found in the periphery associated with connective or any associated adjacent tissue.

In certain embodiments of these scoring methods, the samples are scored by two pathologists operating independently, and the scores are subsequently consolidated. In certain other embodiments, the identification of positive and negative cells is scored using appropriate software.

A histoscore is used as a more quantitative measure of the IHC data. The histoscore is calculated as follows:

$$\text{Histoscore} = [(\% \text{ tumor} \times 1(\text{low intensity})) + (\% \text{ tumor} \times 2(\text{medium intensity})) + (\% \text{ tumor} \times 3(\text{high intensity}))]$$

To determine the histoscore, the pathologist estimates the percentage of stained cells in each intensity category within a specimen. Because expression of most biomarkers is heterogeneous the histoscore is a truer representation of the overall expression. The final histoscore range is 0 (no expression) to 300 (maximum expression).

An alternative means of quantifying PD-L1 expression in a test tissue sample IHC is to determine the adjusted inflammation score (AIS) score defined as the density of inflammation multiplied by the percent PD-L1 expression by tumor-infiltrating inflammatory cells (Taube et al., "Colocalization of inflammatory response with B7-h1 expression in human melanocytic lesions supports an adaptive resistance mechanism of immune escape," *Sci. Transl. Med.* 4(127):127ra37 (2012)).

In one embodiment, the PD-L1 expression level of a tumor is at least about 1%, at least about 2%, at least about 3%, at least about 4%, at least about 5%, at least about 6%, at least about 7%, at least about 8%, at least about 9%, at least about 10%, at least about 11%, at least about 12%, at least about 13%, at least about 14%, at least about 15%, at least about 20%, at least about 25%, at least about 30%, at least about 40%, at least about 50%, at least about 60%, at least about 70%, at least about 75%, at least about 80%, at least about 85%, at least about 90%, at least about 95%, or about 100%. In another embodiment, the PD-L1 status of a tumor is at least about 1%. In other embodiments, the PD-L1 status of the subject is at least about 5%. In a certain embodiment, the PD-L1 status of a tumor is at least about 10%. In one embodiment, the PD-L1 status of the tumor is at least about 25%. In a particular embodiment, the PD-L1 status of the tumor is at least about 50%.

"PD-L1 positive" as used herein can be interchangeably used with "PD-L1 expression of at least about 1%". In one embodiment, the PD-L1 positive tumors can thus have at least about 1%, at least about 2%, at least about 5%, at least about 10%, at least about 20%, at least about 25%, at least about 30%, at least about 40%, at least about 50%, at least about 60%, at least about 70%, at least about 75%, at least about 80%, at least about 85%, at least about 90%, at least about 95%, or about 100% of the tumor cells expressing PD-L1 as measured by an automated IHC. In certain embodiments, "PD-L1 positive" means that there are at least 100 cells that express PD-L1 on the surface of the cells.

In one embodiment, a PD-L1 positive tumor with high TMB has a greater likelihood of response to therapy with an anti-PD-1 antibody than a tumor with only high TMB, only PD-L1 positive expression, or neither. In one embodiment, the tumor has at least about 1%, about 5%, about 10%, about 15%, about 20%, about 25%, about 30%, about 35%, about 40%, about 45%, or about 50% PD-L1 expression. In a particular embodiment, a tumor with ≥50% PD-L1 expression and a high TMB status is more likely to respond to therapy with an anti-PD-1 antibody than a tumor with only high TMB, only ≥50% PD-L1 expression, or neither.

In certain embodiments, the tumor in the subject suitable for the immunotherapy, e.g., an anti-PD-1 antibody treatment, in this disclosure does not express PD-L1 (less than 1%, less than 2%, less than 3%, less than 4%, or less than 5% membranous PD-L1). In some embodiments, the methods of the present disclosure are irrelevant to the PD-L1 expression.

MSI Status

TMB status can be used alone or in combination with other factors, e.g., MSI status, as a means to predict a tumor's response to therapy and, in particular, treatment with an immuno-oncology agent, such as an anti-PD-1 antibody and/or an anti-CTLA-4 antibody. In one embodiment, the MSI status is part of the TMB status. In other embodiments, the MSI status is measured separately from the TMB status.

Microsatellite instability is the condition of genetic hypermutability that results from impaired DNA mismatch repair (MMR). The presence of MSI represents phenotypic evidence that MMR is not functioning normally. In most cases, the genetic basis for instability in MSI tumors is an inherited germline alteration in any one of the five human MMR genes: MSH2, MLH1, MSH6, PMS2, and PMS1. In certain embodiments, the subject receiving tumor (e.g., colon tumor) treatment has a high degree of microsatellite instability (MSI-H) and has at least one mutation in genes MSH2, MLH1, MSH6, PMS2, or PMS1. In other embodiments, subjects receiving tumor treatment within a control group have no microsatellite instability (MSS or MSI stable) and has no mutation in genes MSH2, MLH1, MSH6, PMS2, and PMS1.

In one embodiment, the subject suitable for the immunotherapy has a high TMB status and a MSI-H tumor. As used herein, MSI-H tumors mean tumors having greater than at least about 30% of unstable MSI biomarkers. In some embodiments, the tumor is derived from a colorectal cancer. In some embodiments, the tumor is a colorectal cancer with MSI-H when a germline alteration is detected in at least two, at least three, at least four, or at least five MMR genes. In other embodiments, the tumor is a colorectal cancer with MSI-H when a germline alteration is detected in at least 30% of five or more MMR genes. In some embodiments, a germline alternation in MMR genes is measured by a polymerase chain reaction. In other embodiments, the tumor is a colorectal cancer with MSI-H when at least one protein encoded by DNA MMR genes is not detected in the tumor. In some embodiments, the at least one protein encoded by DNA MMR genes is detected by an immunohistochemistry.

Treatment Methods of the Disclosure

Certain aspects of the present disclosure are directed to a method for treating a subject afflicted with a tumor derived from an SCLC having a high tumor mutational burden (TMB) status comprising administering to the subject an anti-PD-1 antibody or an anti-PD-L1 antibody. Other aspects of the present disclosure are directed to a method for treating a subject afflicted with a tumor derived from an SCLC comprising administering to the subject a therapeutically effective amount of an anti-PD-1 antibody (or an anti-PD-L1 antibody) and an antibody or antigen-binding portion thereof that binds specifically to CTLA-4 ("an anti-CTLA-4 antibody"), wherein the tumor has a TMB status that is a high TMB. The method can further comprise measuring the TMB status of a biological sample obtained from the subject. Additionally, the disclosure contemplates administering an anti-PD-1 or an anti-PD-L1 antibody to a subject identified as suitable for such therapy, e.g., based on measurement of a high TMB.

In one embodiment, the anti-PD-1 antibody cross-competes with nivolumab for binding to human PD-1. In another embodiment, the anti-PD-1 antibody thereof binds to the same epitope as nivolumab. In a particular embodiment, the anti-PD-1 antibody is nivolumab. In another particular embodiment, the anti-PD-1 antibody is pembrolizumab. Additional anti-PD-1 antibodies are described elsewhere herein. In other embodiments, an anti-PD-L1 antibody useful for the methods of the disclosure is described elsewhere herein.

In some embodiments, the anti-PD-1 antibody (or an anti-PD-L1 antibody) and/or the anti-CTLA-4 antibody is a chimeric antibody, a humanized antibody, a human monoclonal antibody, or an antigen-binding portion thereof. In other embodiments, the anti-PD-1 antibody (or an anti-PD-L1 antibody) and the anti-CTLA-4 antibody comprises a heavy chain constant region of a human IgG1 isotype or a human IgG4 isotype.

In some embodiments, the anti-PD-1 antibody thereof is administered at a dose ranging from 0.1 mg/kg to 10.0 mg/kg body weight once every 2, 3, or 4 weeks. In other embodiments, the anti-PD-1 antibody is administered at a dose of 5 mg/kg or 10 mg/kg body weight once every 3 weeks. In one embodiment, the anti-PD-1 antibody is administered at a dose of 5 mg/kg body weight once every 3 weeks. In another embodiment, the anti-PD-1 antibody is administered at a dose of 3 mg/kg body weight once every 2 weeks. In other embodiments, the anti-PD-1 antibody is administered at a dose of 2 mg/kg body weight once every 3 weeks.

In some embodiments, the anti-PD-1 antibody (or an anti-PD-L1 antibody) and/or the anti-CTLA-4 antibody is administered as a flat dose. In one embodiment, the anti-PD-1 antibody and/or the anti-CTLA-4 antibody is administered as a flat dose of at least about 200 mg, at least about 220 mg, at least about 240 mg, at least about 260 mg, at least about 280 mg, at least about 300 mg, at least about 320 mg, at least about 340 mg, at least about 360 mg, at least about 380 mg, at least about 400 mg, at least about 420 mg, at least about 440 mg, at least about 460 mg, at least about 480 mg, at least about 500 mg, or at least about 550 mg. In another embodiment, the anti-PD-1 antibody and/or the anti-CTLA-4 antibody is administered as a flat dose about once every 1, 2, 3, or 4 weeks.

In some embodiments, the anti-PD-1 antibody is administered at a dose of 1 mg/kg once every three weeks, and the anti-CTLA-4 antibody is administered at a dose of 3 mg/kg once every three weeks. In other embodiments, the 1 mg/kg dose of the anti-PD-1 antibody and the 3 mg/kg dose of the anti-CTLA-4 antibody are administered one dose for each, two doses for each, three doses for each, four doses for each, five doses for each, six doses for each, seven doses for each, eight doses for each, nine doses for each, or ten doses for each. In further embodiments, the combination therapy of the anti-PD-1 antibody and the anti-CTLA-4 antibody is followed by a monotherapy of an anti-PD-1 antibody, e.g., at a dose of 3 mg/kg once every two weeks.

In certain embodiments, the anti-PD-1 antibody is administered at a subtherapeutic dose. In certain other embodiments, the anti-CTLA-4 antibody is administered at a subtherapeutic dose. In further embodiments, both the anti-PD-1 antibody and the anti-CTLA-4 antibody are each administered at a subtherapeutic dose.

This disclosure provides a method of treating a subject afflicted with a tumor derived from an SCLC, which method comprises administering to the subject an anti-PD-1 antibody. This disclosure further provides a method of treating a subject afflicted with a tumor derived from an SCLC, which method comprises administering to the subject a combination of (a) an anti-PD-1 antibody; and (b) an anti-CTLA-4 antibody. In some embodiments, the subject is a human patient.

In certain embodiments, the subject is a chemotherapy-naïve patient (e.g., a patient who has not previously received any chemotherapy). In other embodiments, the subject has received another cancer therapy (e.g., a chemotherapy), but is resistant or refractory to such another cancer therapy. In one particular embodiment, the SCLC is a recurrent SCLC. In some embodiments, the subject received at least one, at least two, at least three, at least four, or at least five previous lines of therapy to treat the tumor. In one embodiment, the subject received one previous line of therapy to treat the tumor. In another embodiment, the subject received two previous lines of therapy to treat the tumor. In another embodiment, the subject received three previous lines of therapy to treat the tumor. In another embodiment, the subject received four previous lines of therapy to treat the tumor. In another embodiment, the subject received five previous lines of therapy to treat the tumor. In another embodiment, the subject received more than five previous lines of therapy to treat the tumor.

In certain embodiments, the previous line of therapy comprises a chemotherapy. In some embodiments, the chemotherapy comprises a platinum-based therapy. In certain embodiments, the platinum based therapy comprises a platinum-based antineoplastic selected from the group consisting of cisplatin, carboplatin, oxaliplatin, nedaplatin, triplatin tetranitrate, phenanthriplatin, picoplatin, satraplatin, and any combination thereof. In one particular embodiment, the platinum-based therapy comprises cisplatin (e.g., cisplatin in combination with etoposide). In some embodiments, the subject has received a previous radiotherapy. In other embodiments, the previous therapy comprises an antibody therapy.

In certain specific embodiments, the subject has cancer cells expressing mutated forms of the EGFR or KRAS gene. In certain embodiments, the subject has cancer cells that are PD-L1 positive. In certain embodiments, the subject has cancer cells that are PD-L1 negative. In some embodiments, the subject never smoked. In certain embodiments, the subject formerly smoked. In one embodiment, the subject currently smokes. In certain embodiments, the SCLC comprises a small cell carcinoma. In certain embodiments, the SCLC comprises a combined small cell carcinoma.

Certain cancer types have a higher frequency of mutations and, thus, have a high TMB. (Alexandrov et al., Nature (2013) 500:415-421.) Non-limiting examples of cancers with a high TMB include melanoma, lung, bladder, and gastrointestinal cancers. In some embodiments, the tumor is lung cancer. In one embodiment, the lung cancer is small cell lung cancer (SCLC). In one embodiment, the NSCLC has a squamous histology. In another embodiment, the NSCLC has a non-squamous histology. In other embodiments, the tumor is selected from renal cell carcinoma, ovarian cancer, colorectal cancer, gastrointestinal cancer, esophageal cancer, bladder cancer, lung cancer, and melanoma. It should be understood that the methods disclosed herein encompass solid tumors as well as blood cancers.

The methods of treatment disclosed herein can provide an improved clinical response and/or clinical benefit for subjects afflicted with a tumor and, in particular, subjects having a tumor with a high TMB. High TMB can be related to neoantigen burden, i.e., the number of neoantigens and T-cell reactivity and, thus, an immune-mediated anti-tumor response. Accordingly, high TMB is a factor that can be used, alone or in combination with other factors, to identity tumors (and patients having such tumors) more likely to benefit from therapy with an anti-PD-1 antibody and/or an anti-PD-L1 antibody, e.g., as compared to current standard of care therapies.

In one embodiment, the subject exhibits progression-free survival of at least about one month, at least about 2 months, at least about 3 months, at least about 4 months, at least about 5 months, at least about 6 months, at least about 7 months, at least about 8 months, at least about 9 months, at least about 10 months, at least about 11 months, at least about one year, at least about eighteen months, at least about two years, at least about three years, at least about four years, or at least about five years after the administration. In another embodiment, the subject exhibits an overall survival of at least about one month, at least about 2 months, at least about 3 months, at least about 4 months, at least about 5 months, at least about 6 months, at least about 7 months, at least about 8 months, at least about 9 months, at least about 10 months, at least about 11 months, at least about one year, at least about eighteen months, at least about two years, at least about three years, at least about four years, or at least about five years after the administration. In yet another embodiment, the subject exhibits an objective response rate of at least about 30%, about 35%, about 40%, about 45%, about 50%, about 55%, about 60%, about 65%, about 70%, about 75%, about 80%, about 85%, about 90%, about 95%, or about 100%.

Anti-PD-1 Treatment

Certain aspects of the present disclosure are directed to a method for treating a subject afflicted with a tumor derived from an SCLC having a high tumor mutation burden (TMB) status comprising administering to the subject an immunotherapy, wherein the immunotherapy comprises an anti-PD-1 antibody (or anti-PD-L1 antibody) alone or an anti-PD-1 antibody and an anti-CTLA-4 antibody.

In one embodiment, the anti-PD-1 antibody cross-competes with nivolumab for binding to human PD-1. In another embodiment, the anti-PD-1 antibody binds to the same epitope as nivolumab. In other embodiments, an anti-PD-1 antibody useful for the methods of the disclosure is described elsewhere herein. In other embodiments, an anti-PD-L1 antibody can be used instead of an anti-PD-1 antibody. Non-limiting examples of the anti-PD-L1 antibodies are disclosed elsewhere herein.

In some embodiments, the anti-PD-1 antibody or an anti-PD-L1 antibody is a chimeric antibody, a humanized antibody, a human antibody, or an antigen-binding portion thereof. In other embodiments, the anti-PD-1 antibody or an anti-PD-L1 antibody comprises a heavy chain constant region of a human IgG1 isotype or a human IgG4 isotype.

Anti-PD-1 Antibodies Useful for the Disclosure

Anti-PD-1 antibodies that are known in the art can be used in the presently described compositions and methods. Various human monoclonal antibodies that bind specifically to PD-1 with high affinity have been disclosed in U.S. Pat. No. 8,008,449. Anti-PD-1 human antibodies disclosed in U.S. Pat. No. 8,008,449 have been demonstrated to exhibit one or more of the following characteristics: (a) bind to human PD-1 with a $K_D$ of $1\times10^{-7}M$ or less, as determined by surface plasmon resonance using a Biacore biosensor system; (b) do not substantially bind to human CD28, CTLA-4 or ICOS; (c) increase T-cell proliferation in a Mixed Lymphocyte Reaction (MLR) assay; (d) increase interferon-γ production in an MLR assay; (e) increase IL-2 secretion in an MLR assay; (f) bind to human PD-1 and cynomolgus monkey PD-1; (g) inhibit the binding of PD-L1 and/or PD-L2 to PD-1; (h) stimulate antigen-specific memory responses; (i) stimulate antibody responses; and (j) inhibit tumor cell growth in vivo. Anti-PD-1 antibodies usable in the present disclosure include monoclonal antibodies that bind specifically to human PD-1 and exhibit at least one, in some embodiments, at least five, of the preceding characteristics.

Other anti-PD-1 monoclonal antibodies have been described in, for example, U.S. Pat. Nos. 6,808,710, 7,488,802, 8,168,757 and 8,354,509, US Publication No. 2016/0272708, and PCT Publication Nos. WO 2012/145493, WO 2008/156712, WO 2015/112900, WO 2012/145493, WO 2015/112800, WO 2014/206107, WO 2015/35606, WO 2015/085847, WO 2014/179664, WO 2017/020291, WO 2017/020858, WO 2016/197367, WO 2017/024515, WO 2017/025051, WO 2017/123557, WO 2016/106159, WO 2014/194302, WO 2017/040790, WO 2017/133540, WO 2017/132827, WO 2017/024465, WO 2017/025016, WO 2017/106061, WO 2017/19846, WO 2017/024465, WO 2017/025016, WO 2017/132825, and WO 2017/133540 each of which is incorporated by reference in its entirety.

In some embodiments, the anti-PD-1 antibody is selected from the group consisting of nivolumab (also known as OPDIVO®, 5C4, BMS-936558, MDX-1106, and ONO-4538), pembrolizumab (Merck; also known as KEYTRUDA®, lambrolizumab, and MK-3475; see WO2008/156712), PDR001 (Novartis; also known as spartalizumab; see WO 2015/112900), MEDI-0680 (AstraZeneca; also known as AMP-514; see WO 2012/145493), cemiplimab (Regeneron; also known as REGN-2810; see WO 2015/112800), JS001 (TAIZHOU JUNSHI PHARMA; see Si-Yang Liu et al., *J. Hematol. Oncol.* 10:136 (2017)), BGB-A317 ("Tislelizumab;" Beigene; see WO 2015/35606 and US 2015/0079109), INCSHR1210 (Jiangsu Hengrui Medicine; also known as SHR-1210; see WO 2015/085847; Si-Yang Liu et al., *J. Hematol. Oncol.* 10:136 (2017)), TSR-042 (Tesaro Biopharmaceutical; also known as ANB011; see WO2014/179664), GLS-010 (Wuxi/Harbin Gloria Pharmaceuticals; also known as WBP3055; see Si-Yang Liu et al., *J. Hematol. Oncol.* 10:136 (2017)), AM-0001 (Armo), STI-1110 (Sorrento Therapeutics; see WO 2014/194302), AGEN2034 (Agenus; see WO 2017/040790), MGA012 (Macrogenics, see WO 2017/19846), IBI308 (Innovent; see WO 2017/024465, WO 2017/025016, WO 2017/132825, and WO 2017/133540), and BCD-100 (Biocad).

In one embodiment, the anti-PD-1 antibody is nivolumab. Nivolumab is a fully human IgG4 (S228P) PD-1 immune checkpoint inhibitor antibody that selectively prevents interaction with PD-1 ligands (PD-L1 and PD-L2), thereby blocking the down-regulation of antitumor T-cell functions (U.S. Pat. No. 8,008,449; Wang et al., 2014 *Cancer Immunol Res.* 2(9):846-56).

In another embodiment, the anti-PD-1 antibody is pembrolizumab. Pembrolizumab is a humanized monoclonal IgG4 (S228P) antibody directed against human cell surface receptor PD-1 (programmed death-1 or programmed cell death-1). Pembrolizumab is described, for example, in U.S. Pat. Nos. 8,354,509 and 8,900,587.

Anti-PD-1 antibodies usable in the disclosed compositions and methods also include isolated antibodies that bind specifically to human PD-1 and cross-compete for binding to human PD-1 with any anti-PD-1 antibody disclosed herein, e.g., nivolumab (see, e.g., U.S. Pat. Nos. 8,008,449 and 8,779,105; WO 2013/173223). In some embodiments, the anti-PD-1 antibody binds the same epitope as any of the anti-PD-1 antibodies described herein, e.g., nivolumab. The ability of antibodies to cross-compete for binding to an antigen indicates that these monoclonal antibodies bind to the same epitope region of the antigen and sterically hinder the binding of other cross-competing antibodies to that particular epitope region. These cross-competing antibodies are expected to have functional properties very similar those of the reference antibody, e.g., nivolumab, by virtue of their binding to the same epitope region of PD-1. Cross-competing antibodies can be readily identified based on their ability to cross-compete with nivolumab in standard PD-1 binding assays such as Biacore analysis, ELISA assays or flow cytometry (see, e.g., WO 2013/173223).

In certain embodiments, the antibodies that cross-compete for binding to human PD-1 with, or bind to the same epitope region of human PD-1 antibody, nivolumab, are monoclonal antibodies. For administration to human subjects, these cross-competing antibodies are chimeric antibodies, engineered antibodies, or humanized or human antibodies. Such chimeric, engineered, humanized or human monoclonal antibodies can be prepared and isolated by methods well known in the art.

Anti-PD-1 antibodies usable in the compositions and methods of the disclosure also include antigen-binding portions of the above antibodies. It has been amply demonstrated that the antigen-binding function of an antibody can be performed by fragments of a full-length antibody.

Anti-PD-1 antibodies suitable for use in the disclosed compositions and methods are antibodies that bind to PD-1 with high specificity and affinity, block the binding of PD-L1 and or PD-L2, and inhibit the immunosuppressive effect of the PD-1 signaling pathway. In any of the compositions or methods disclosed herein, an anti-PD-1 "antibody" includes an antigen-binding portion or fragment that binds to the PD-1 receptor and exhibits the functional properties similar to those of whole antibodies in inhibiting ligand binding and up-regulating the immune system. In certain embodiments, the anti-PD-1 antibody or antigen-binding portion thereof cross-competes with nivolumab for binding to human PD-1.

In some embodiments, the anti-PD-1 antibody is administered at a dose ranging from 0.1 mg/kg to 20.0 mg/kg body weight once every 2, 3, 4, 5, 6, 7, or 8 weeks, e.g., 0.1 mg/kg to 10.0 mg/kg body weight once every 2, 3, or 4 weeks. In other embodiments, the anti-PD-1 antibody is administered at a dose of about 2 mg/kg, about 3 mg/kg, about 4 mg/kg, about 5 mg/kg, about 6 mg/kg, about 7 mg/kg, about 8 mg/kg, about 9 mg/kg, or 10 mg/kg body weight once every 2 weeks. In other embodiments, the anti-PD-1 antibody is administered at a dose of about 2 mg/kg, about 3 mg/kg, about 4 mg/kg, about 5 mg/kg, about 6 mg/kg, about 7 mg/kg, about 8 mg/kg, about 9 mg/kg, or 10 mg/kg body weight once every 3 weeks. In one embodiment, the anti-PD-1 antibody is administered at a dose of about 5 mg/kg body weight about once every 3 weeks. In another embodiment, the anti-PD-1 antibody, e.g., nivolumab, is administered at a dose of about 3 mg/kg body weight about once every 2 weeks. In other embodiments, the anti-PD-1 antibody, e.g., pembrolizumab, is administered at a dose of about 2 mg/kg body weight about once every 3 weeks.

The anti-PD-1 antibody useful for the present disclosure can be administered as a flat dose. In some embodiments, the anti-PD-1 antibody is administered at a flat dose of from about 100 to about 1000 mg, from about 100 mg to about 900 mg, from about 100 mg to about 800 mg, from about 100 mg to about 700 mg, from about 100 mg to about 600 mg, from about 100 mg to about 500 mg, from about 200 mg to about 1000 mg, from about 200 mg to about 900 mg, from about 200 mg to about 800 mg, from about 200 mg to about 700 mg, from about 200 mg to about 600 mg, from about 200 mg to about 500 mg, from about 200 mg to about 480 mg, or from about 240 mg to about 480 mg, In one embodiment, the anti-PD-1 antibody is administered as a flat dose of at least about 200 mg, at least about 220 mg, at least about 240 mg, at least about 260 mg, at least about 280 mg, at least about 300 mg, at least about 320 mg, at least about 340 mg, at least about 360 mg, at least about 380 mg, at least about 400 mg, at least about 420 mg, at least about 440 mg, at least about 460 mg, at least about 480 mg, at least about 500 mg, at least about 520 mg, at least about 540 mg, at least about 550 mg, at least about 560 mg, at least about 580 mg, at least about 600 mg, at least about 620 mg, at least about 640 mg, at least about 660 mg, at least about 680 mg, at least about 700 mg, or at least about 720 mg at a dosing interval of about 1, 2, 3, 4, 5, 6, 7, 8, 9, or 10 weeks. In another embodiments, the anti-PD-1 antibody is administered as a flat dose of about 200 mg to about 800 mg, about 200 mg to about 700 mg, about 200 mg to about 600 mg, about 200 mg to about 500 mg, at a dosing interval of about 1, 2, 3, or 4 weeks.

In some embodiments, the anti-PD-1 antibody is administered as a flat dose of about 200 mg at about once every 3 weeks. In other embodiments, the anti-PD-1 antibody is administered as a flat dose of about 200 mg at about once every 2 weeks. In other embodiments, the anti-PD-1 antibody is administered as a flat dose of about 240 mg at about once every 2 weeks. In certain embodiments, the anti-PD-1 antibody is administered as a flat dose of about 480 mg at about once every 4 weeks.

Anti-PD-L1 Antibodies Useful for the Disclosure

Because anti-PD-1 and anti-PD-L1 target the same signaling pathway and have been shown in clinical trials to exhibit similar levels of efficacy in a variety of cancers, including renal cell carcinoma (see Brahmer et al. (2012) *N Engl J Med* 366:2455-65; Topalian et al. (2012a) *N Engl J Med* 366:2443-54; WO 2013/173223), an anti-PD-L1 antibody may be substituted for the anti-PD-1 antibody in any of the therapeutic methods disclosed herein. Accordingly, certain aspects of the present disclosure are directed to methods for treating a subject afflicted with a tumor, e.g., SCLC, having a high TMB status comprising administering to the subject an anti-PD-L1 antibody alone ("monotherapy") or an anti-PD-L1 antibody in combination with an anti-CTLA-4 antibody. Anti-PD-L1 antibodies that are known in the art can be used in the compositions and methods of the present disclosure. Examples of anti-PD-L1 antibodies useful in the compositions and methods of the present disclosure include the antibodies disclosed in U.S. Pat. No. 9,580,507. Anti-PD-L1 human monoclonal antibodies disclosed in U.S. Pat. No. 9,580,507 have been demonstrated to exhibit one or more of the following characteristics: (a) bind to human PD-L1 with a $K_D$ of $1\times10^{-7}$M or less, as determined by surface plasmon resonance using a Biacore biosensor system; (b) increase T-cell proliferation in a Mixed Lymphocyte Reaction (MLR) assay; (c) increase interferon-γ production in an MLR assay; (d) increase IL-2 secretion in an MLR assay; (e) stimulate antibody responses; and (f) reverse the effect of T regulatory cells on T cell effector cells and/or dendritic cells. Anti-PD-L1 antibodies usable in the present disclosure include monoclonal antibodies that bind specifically to human PD-L1 and exhibit at least one, in some embodiments, at least five, of the preceding characteristics.

In certain embodiments, the anti-PD-L1 antibody is selected from the group consisting of BMS-936559 (also known as 12A4, MDX-1105; see, e.g., U.S. Pat. No. 7,943,743 and WO 2013/173223), atezolizumab (Roche; also known as TECENTRIQ®; MPDL3280A, RG7446; see U.S. Pat. No. 8,217,149; see, also, Herbst et al. (2013) *J Clin Oncol* 31(suppl):3000), durvalumab (AstraZeneca; also known as IMFINZI™, MEDI-4736; see WO 2011/066389), avelumab (Pfizer; also known as BAVENCIO®, MSB-0010718C; see WO 2013/079174), STI-1014 (Sorrento; see WO2013/181634), CX-072 (Cytomx; see WO2016/149201), KN035 (3D Med/Alphamab; see Zhang et al., *Cell Discov.* 7:3 (March 2017), LY3300054 (Eli Lilly Co.; see, e.g., WO 2017/034916), and CK-301 (Checkpoint Therapeutics; see Gorelik et al., AACR:Abstract 4606 (April 2016)).

In certain embodiments, the PD-L1 antibody is atezolizumab (TECENTRIQ®). Atezolizumab is a fully humanized IgG1 monoclonal anti-PD-L1 antibody.

In certain embodiments, the PD-L1 antibody is durvalumab (IMFINZI™) Durvalumab is a human IgG1 kappa monoclonal anti-PD-L1 antibody.

In certain embodiments, the PD-L1 antibody is avelumab (BAVENCIO®). Avelumab is a human IgG1 lambda monoclonal anti-PD-L1 antibody.

Anti-PD-L1 antibodies usable in the disclosed compositions and methods also include isolated antibodies that bind specifically to human PD-L1 and cross-compete for binding to human PD-L1 with any anti-PD-L1 antibody disclosed herein, e.g., atezolizumab, durvalumab, and/or avelumab. In some embodiments, the anti-PD-L1 antibody binds the same epitope as any of the anti-PD-L1 antibodies described herein, e.g., atezolizumab, durvalumab, and/or avelumab. The ability of antibodies to cross-compete for binding to an antigen indicates that these antibodies bind to the same epitope region of the antigen and sterically hinder the binding of other cross-competing antibodies to that particular epitope region. These cross-competing antibodies are expected to have functional properties very similar those of the reference antibody, e.g., atezolizumab and/or avelumab, by virtue of their binding to the same epitope region of PD-L1. Cross-competing antibodies can be readily identified based on their ability to cross-compete with atezolizumab and/or avelumab in standard PD-L1 binding assays such as Biacore analysis, ELISA assays or flow cytometry (see, e.g., WO 2013/173223).

In certain embodiments, the antibodies that cross-compete for binding to human PD-L1 with, or bind to the same epitope region of human PD-L1 antibody as, atezolizumab, durvalumab, and/or avelumab, are monoclonal antibodies. For administration to human subjects, these cross-competing antibodies are chimeric antibodies, engineered antibodies, or humanized or human antibodies. Such chimeric, engineered, humanized or human monoclonal antibodies can be prepared and isolated by methods well known in the art.

Anti-PD-L1 antibodies usable in the compositions and methods of the disclosed disclosure also include antigen-binding portions of the above antibodies. It has been amply demonstrated that the antigen-binding function of an antibody can be performed by fragments of a full-length antibody.

Anti-PD-L1 antibodies suitable for use in the disclosed compositions and methods are antibodies that bind to PD-L1 with high specificity and affinity, block the binding of PD-1, and inhibit the immunosuppressive effect of the PD-1 signaling pathway. In any of the compositions or methods disclosed herein, an anti-PD-L1 "antibody" includes an antigen-binding portion or fragment that binds to PD-L1 and exhibits the functional properties similar to those of whole antibodies in inhibiting receptor binding and up-regulating the immune system. In certain embodiments, the anti-PD-L1 antibody or antigen-binding portion thereof cross-competes with atezolizumab, durvalumab, and/or avelumab for binding to human PD-L1.

The anti-PD-L1 antibody useful for the present disclosure can be any PD-L1 antibody that specifically binds to PD-L1, e.g., antibodies that cross-compete with durvalumab, avelumab, or atezolizumab for binding to human PD-1, e.g., an antibody that binds to the same epitope as durvalumab, avelumab, or atezolizumab. In a particular embodiment, the anti-PD-L1 antibody is durvalumab. In other embodiments, the anti-PD-L1 antibody is avelumab. In some embodiments, the anti-PD-L1 antibody is atezolizumab.

In some embodiments, the anti-PD-L1 antibody is administered at a dose ranging from about 0.1 mg/kg to about 20.0 mg/kg body weight, about 2 mg/kg, about 3 mg/kg, about 4 mg/kg, about 5 mg/kg, about 6 mg/kg, about 7 mg/kg, about 8 mg/kg, about 9 mg/kg, about 10 mg/kg, about 11 mg/kg, about 12 mg/kg, about 13 mg/kg, about 14 mg/kg, about 15 mg/kg, about 16 mg/kg, about 17 mg/kg, about 18 mg/kg, about 19 mg/kg, or about 20 mg/kg, about once every 2, 3, 4, 5, 6, 7, or 8 weeks.

In some embodiments, the anti-PD-L1 antibody is administered at a dose of about 15 mg/kg body weight at about once every 3 weeks. In other embodiments, the anti-PD-L1 antibody is administered at a dose of about 10 mg/kg body weight at about once every 2 weeks.

In other embodiments, the anti-PD-L1 antibody useful for the present disclosure is a flat dose. In some embodiments, the anti-PD-L1 antibody is administered as a flat dose of from about 200 mg to about 1600 mg, about 200 mg to about 1500 mg, about 200 mg to about 1400 mg, about 200 mg to about 1300 mg, about 200 mg to about 1200 mg, about 200 mg to about 1100 mg, about 200 mg to about 1000 mg, about 200 mg to about 900 mg, about 200 mg to about 800 mg, about 200 mg to about 700 mg, about 200 mg to about 600 mg, about 700 mg to about 1300 mg, about 800 mg to about 1200 mg, about 700 mg to about 900 mg, or about 1100 mg to about 1300 mg. In some embodiments, the anti-PD-L1 antibody is administered as a flat dose of at least about 240 mg, at least about 300 mg, at least about 320 mg, at least about 400 mg, at least about 480 mg, at least about 500 mg, at least about 560 mg, at least about 600 mg, at least about 640 mg, at least about 700 mg, at least 720 mg, at least about 800 mg, at least about 880 mg, at least about 900 mg, at least 960 mg, at least about 1000 mg, at least about 1040 mg, at least about 1100 mg, at least about 1120 mg, at least about 1200 mg, at least about 1280 mg, at least about 1300 mg, at least about 1360 mg, or at least about 1400 mg, at a dosing interval of about 1, 2, 3, or 4 weeks. In some embodiments, the anti-PD-L1 antibody is administered at a flat dose of about 1000 mg. In some embodiments, the anti-PD-L1 antibody is administered at a flat dose of about 1100 mg. In some embodiments, the anti-PD-L1 antibody is administered at a flat dose of about 1200 mg. In some embodiments, the anti-PD-L1 antibody is administered at a flat dose of about 1300 mg. In some embodiments, the anti-PD-L1 antibody is administered at a flat dose of about 1400 mg. In some embodiments, the anti-PD-L1 antibody is administered at a flat dose of about 1500 mg. In some embodiments, the anti-PD-L1 antibody is administered as a flat dose of about 1200 mg at about once every 3 weeks. In other embodiments, the anti-PD-L1 antibody is administered as a flat dose of about 800 mg at about once every 2 weeks.

Anti-CTLA-4 Antibodies

Anti-CTLA-4 antibodies that are known in the art can be used in the compositions and methods of the present disclosure. Anti-CTLA-4 antibodies of the instant disclosure bind to human CTLA-4 so as to disrupt the interaction of CTLA-4 with a human B7 receptor. Because the interaction of CTLA-4 with B7 transduces a signal leading to inactivation of T-cells bearing the CTLA-4 receptor, disruption of the interaction effectively induces, enhances or prolongs the activation of such T cells, thereby inducing, enhancing or prolonging an immune response.

Human monoclonal antibodies that bind specifically to CTLA-4 with high affinity have been disclosed in U.S. Pat. No. 6,984,720. Other anti-CTLA-4 monoclonal antibodies have been described in, for example, U.S. Pat. Nos. 5,977,318, 6,051,227, 6,682,736, and 7,034,121 and International Publication Nos. WO 2012/122444, WO 2007/113648, WO 2016/196237, and WO 2000/037504, each of which is incorporated by reference herein in its entirety. The anti-CTLA-4 human monoclonal antibodies disclosed in U.S. Pat. No. 6,984,720 have been demonstrated to exhibit one or more of the following characteristics: (a) binds specifically to human CTLA-4 with a binding affinity reflected by an equilibrium association constant ($K_a$) of at least about $10^7 M^{-1}$, or about $10^9 M^{-1}$, or about $10^{10} M^{-1}$ to $10^{11} M^{-1}$ or higher, as determined by Biacore analysis; (b) a kinetic association constant ($k_a$) of at least about $10^3$, about $10^4$, or about $10^5$ m$^{-1}$ s$^{-1}$; (c) a kinetic disassociation constant ($k_d$) of at least about $10^3$, about $10^4$, or about $10^5$ m$^{-1}$ s$^{-1}$; and (d) inhibits the binding of CTLA-4 to B7-1 (CD80) and B7-2 (CD86). Anti-CTLA-4 antibodies useful for the present disclosure include monoclonal antibodies that bind specifically to human CTLA-4 and exhibit at least one, at least two, or at least three of the preceding characteristics.

In certain embodiments, the CTLA-4 antibody is selected from the group consisting of ipilimumab (also known as YERVOY®, MDX-010, 10D1; see U.S. Pat. No. 6,984,720), MK-1308 (Merck), AGEN-1884 (Agenus Inc.; see WO 2016/196237), and tremelimumab (AstraZeneca; also known as ticilimumab, CP-675,206; see WO 2000/037504 and Ribas, *Update Cancer Ther.* 2(3): 133-39 (2007)). In particular embodiments, the anti-CTLA-4 antibody is ipilimumab.

In particular embodiments, the CTLA-4 antibody is ipilimumab for use in the compositions and methods disclosed herein. Ipilimumab is a fully human, IgG1 monoclonal antibody that blocks the binding of CTLA-4 to its B7 ligands, thereby stimulating T cell activation and improving overall survival (OS) in patients with advanced melanoma.

In particular embodiments, the CTLA-4 antibody is tremelimumab.

In particular embodiments, the CTLA-4 antibody is MK-1308.

In particular embodiments, the CTLA-4 antibody is AGEN-1884.

Anti-CTLA-4 antibodies usable in the disclosed compositions and methods also include isolated antibodies that bind specifically to human CTLA-4 and cross-compete for binding to human CTLA-4 with any anti-CTLA-4 antibody disclosed herein, e.g., ipilimumab and/or tremelimumab. In some embodiments, the anti-CTLA-4 antibody binds the same epitope as any of the anti-CTLA-4 antibodies described herein, e.g., ipilimumab and/or tremelimumab. The ability of antibodies to cross-compete for binding to an antigen indicates that these antibodies bind to the same epitope region of the antigen and sterically hinder the binding of other cross-competing antibodies to that particular epitope region. These cross-competing antibodies are expected to have functional properties very similar those of the reference antibody, e.g., ipilimumab and/or tremelimumab, by virtue of their binding to the same epitope region of CTLA-4. Cross-competing antibodies can be readily identified based on their ability to cross-compete with ipilimumab and/or tremelimumab in standard CTLA-4 binding assays such as Biacore analysis, ELISA assays or flow cytometry (see, e.g., WO 2013/173223).

In certain embodiments, the antibodies that cross-compete for binding to human CTLA-4 with, or bind to the same epitope region of human CTLA-4 antibody as, ipilimumab and/or tremelimumab, are monoclonal antibodies. For administration to human subjects, these cross-competing antibodies are chimeric antibodies, engineered antibodies, or humanized or human antibodies. Such chimeric, engineered, humanized or human monoclonal antibodies can be prepared and isolated by methods well known in the art.

Anti-CTLA-4 antibodies usable in the compositions and methods of the disclosed disclosure also include antigen-binding portions of the above antibodies. It has been amply demonstrated that the antigen-binding function of an antibody can be performed by fragments of a full-length antibody.

Anti-CTLA-4 antibodies suitable for use in the disclosed methods or compositions are antibodies that bind to CTLA-4 with high specificity and affinity, block the activity of CTLA-4, and disrupt the interaction of CTLA-4 with a human B7 receptor. In any of the compositions or methods disclosed herein, an anti-CTLA-4 "antibody" includes an antigen-binding portion or fragment that binds to CTLA-4 and exhibits the functional properties similar to those of whole antibodies in inhibiting the interaction of CTLA-4 with a human B7 receptor and up-regulating the immune system. In certain embodiments, the anti-CTLA-4 antibody or antigen-binding portion thereof cross-competes with ipilimumab and/or tremelimumab for binding to human CTLA-4.

In some embodiments, the anti-CTLA-4 antibody or antigen-binding portion thereof is administered at a dose ranging from 0.1 mg/kg to 10.0 mg/kg body weight once every 2, 3, 4, 5, 6, 7, or 8 weeks. In some embodiments, the anti-CTLA-4 antibody or antigen-binding portion thereof is administered at a dose of 1 mg/kg or 3 mg/kg body weight once every 3, 4, 5, or 6 weeks. In one embodiment, the anti-CTLA-4 antibody or antigen-binding portion thereof is administered at a dose of 3 mg/kg body weight once every 2 weeks. In another embodiment, the anti-PD-1 antibody or antigen-binding portion thereof is administered at a dose of 1 mg/kg body weight once every 6 weeks.

In some embodiments, the anti-CTLA-4 antibody or antigen-binding portion thereof is administered as a flat dose. In some embodiments, the anti-CTLA-4 antibody is administered at a flat dose of from about 10 to about 1000 mg, from about 10 mg to about 900 mg, from about 10 mg to about 800 mg, from about 10 mg to about 700 mg, from about 10 mg to about 600 mg, from about 10 mg to about 500 mg, from about 100 mg to about 1000 mg, from about 100 mg to about 900 mg, from about 100 mg to about 800 mg, from about 100 mg to about 700 mg, from about 100 mg to about 100 mg, from about 100 mg to about 500 mg, from about 100 mg to about 480 mg, or from about 240 mg to about 480 mg. In one embodiment, the anti-CTLA-4 antibody or antigen-binding portion thereof is administered as a flat dose of at least about 60 mg, at least about 80 mg, at least about 100 mg, at least about 120 mg, at least about 140 mg, at least about 160 mg, at least about 180 mg, at least about 200 mg, at least about 220 mg, at least about 240 mg, at least about 260 mg, at least about 280 mg, at least about 300 mg, at least about 320 mg, at least about 340 mg, at least about 360 mg, at least about 380 mg, at least about 400 mg, at least about 420 mg, at least about 440 mg, at least about 460 mg, at least about 480 mg, at least about 500 mg, at least about 520 mg at least about 540 mg, at least about 550 mg, at least about 560 mg, at least about 580 mg, at least about 600 mg, at least about 620 mg, at least about 640 mg, at least about 660 mg, at least about 680 mg, at least about 700 mg, or at least about 720 mg. In another embodiment, the anti-CTLA-4 antibody or antigen-binding portion thereof is administered as a flat dose about once every 1, 2, 3, 4, 5, 6, 7, or 8 weeks.

Cytokines

In some embodiments, the method comprises administering a combination therapy comprising (a) an anti-PD-1 antibody and a cytokine or (b) an anti-PD-1 antibody, an anti-CTLA-4 antibody, and a cytokine. The cytokine can be any cytokine or variant thereof known in the art. In some embodiments, the cytokine is selected from the group consisting of interleukin-2 (IL-2), IL-1β, IL-6, TNF-α, RANTES, monocyte chemoattractant protein (MCP-1), monocyte inflammatory protein (MIP-1α and MIP-1β), IL-8, lymphotactin, fractalkine, IL-1, IL-4, IL-10, IL-11, IL-13, LIF, interferon-alpha, TGF-beta, and any combination thereof. In some embodiments, the cytokine is a CD122 agonist. In certain embodiments, the cytokine comprises IL-2 or a variant thereof.

In some embodiments, the cytokine comprises one or more amino acid substitution, deletion, or insertion relative to the wild-type cytokine amino acid sequence. In some embodiments, the cytokine comprises an amino acid sequence having at least 1, at least 2, at least 3, at least 4, at least 5, at least 6, at least 7, at least 8, at least 9, or at least 10 amino acids substituted relative to the amino acid sequence of the wild-type cytokine.

In some embodiments, the cytokine is modified, e.g., to increase activity and/or half-life. In certain embodiments, the cytokine is modified through fusion of a heterologous moiety to the cytokine. The heterologous moiety can be any structure including a polypeptide, a polymer, a small molecule, a nucleotide, or a fragment or analog thereof. In certain embodiments, the heterologous moiety comprises a polypeptide. In some embodiments, the heterologous moiety comprises albumin or a fragment thereof, albumin-binding polypeptide (ABP), XTEN, Fc, PAS, the C-terminal peptide (CTP) of the β subunit of human chorionic gonadotropin, or any combination thereof.

In certain embodiments, the cytokine is modified through fusion of the cytokine with a polymer. In some embodiments, the polymer comprises polyethylene glycol (PEG), polypropylene glycol (PPG), hydroxyethyl starch (HES), or any combination thereof. "PEG" or "polyethylene glycol," as used herein, is meant to encompass any water-soluble poly(ethylene oxide). Unless otherwise indicated, a "PEG polymer" or a polyethylene glycol is one in which substantially all (preferably all) monomeric subunits are ethylene oxide subunits, though, the polymer may contain distinct end capping moieties or functional groups, e.g., for conjugation. PEG polymers for use in the present disclosure will comprise one of the two following structures: "—$(CH_2CH_2O)_{n-n}$—" or "—$(CH_2CH_2O)_{n-1}CH_2CH_2$—," depending upon whether or not the terminal oxygen(s) has been displaced, e.g., during a synthetic transformation. As stated above, for the PEG polymers, the variable (n) ranges from about 3 to 4000, and the terminal groups and architecture of the overall PEG can vary.

In some embodiments, the methods of the present disclosure comprising administering to a subject having a high TMB status (a) an anti-PD-1 antibody and a CD122 agonist or (b) an anti-PD-1 antibody, an anti-CTLA-4 antibody, and a CD122 agonist. In some embodiments, the immunotherapy comprises administering (1) an anti-PD-1 antibody, an anti-PD-L1 antibody, an anti-CTLA-4 antibody, or any combination thereof and (2) a CD122 agonist. In some embodiments, the CD122 agonist comprises IL-2 or a variant thereof. In some embodiments, the CD122 agonist comprises an IL-2 variant having at least 1 amino acid substitution relative to wild-type IL-2. In some embodiments, the CD122 agonist comprises an IL-2 fused to a PEG. In some embodiments, the CD122 agonist comprises an IL-2 variant having at least 1 amino acid substitution relative to wild-type IL-2, wherein the IL-2 variant is fused to a PEG.

Other Immunotherapies

In some aspects of the present disclosure, the methods disclosed herein further comprise administering an additional anticancer therapy. In some embodiment, the additional anticancer therapy comprises an immunotherapy. In some embodiments, the additional anticancer therapy comprises administration of an antibody or antigen-binding portion thereof that specifically binds LAG3, TIGIT, TIM3, NKG2a, OX40, ICOS, MICA, CD137, KIR, TGFβ, IL-10, IL-8, B7-H4, Fas ligand, CXCR4, mesothelin, CD27, GITR, or any combination thereof.

Anti-LAG-3 Antibodies

Certain aspects of the present disclosure are directed to a method for treating a subject afflicted with a tumor having a high TMB status comprising administering to the subject immunotherapy, wherein the immunotherapy comprises an anti-LAG-3 antibody or antigen-binding portion thereof. The method can further comprise measuring the TMB status of a biological sample obtained from the subject. Additionally, the disclosure contemplates administering an anti-LAG-3 antibody or antigen-binding portion thereof to a subject identified as suitable for such therapy, e.g., based on measurement of a high TMB.

Anti-LAG-3 antibodies of the instant disclosure bind to human LAG-3. Antibodies that bind to LAG-3 have been disclosed in Int'l Publ. No. WO/2015/042246 and U.S. Publ. Nos. 2014/0093511 and 2011/0150892. An exemplary LAG-3 antibody useful in the present disclosure is 25F7 (described in U.S. Publ. No. 2011/0150892). An additional exemplary LAG-3 antibody useful in the present disclosure is BMS-986016. In one embodiment, an anti-LAG-3 antibody useful for the composition cross-competes with 25F7 or BMS-986016. In another embodiment, an anti-LAG-3 antibody useful for the composition binds to the same epitope as 25F7 or BMS-986016. In other embodiments, an anti-LAG-3 antibody comprises six CDRs of 25F7 or BMS-986016.

Anti-CD137 Antibodies

Certain aspects of the present disclosure are directed to a method for treating a subject afflicted with a tumor having a high TMB status comprising administering to the subject immunotherapy, wherein the immunotherapy comprises an anti-CD137 antibody or antigen-binding portion thereof. The method can further comprise measuring the TMB status of a biological sample obtained from the subject. Additionally, the disclosure contemplates administering an anti-CD137 antibody or antigen-binding portion thereof to a subject identified as suitable for such therapy, e.g., based on measurement of a high TMB Anti-CD137 antibodies specifically bind to and activate CD137-expressing immune cells, stimulating an immune response, in particular a cytotoxic T cell response, against tumor cells. Antibodies that bind to CD137 have been disclosed in U.S. Publ. No. 2005/0095244 and U.S. Pat. Nos. 7,288,638, 6,887,673, 7,214,493, 6,303,121, 6,569,997, 6,905,685, 6,355,476, 6,362,325, 6,974,863, and 6,210,669.

In some embodiments, the anti-CD137 antibody is urelumab (BMS-663513), described in U.S. Pat. No. 7,288,638 (20H4.9-IgG4 [10C7 or BMS-663513]). In some embodiments, the anti-CD137 antibody is BMS-663031 (20H4.9-IgG1), described in U.S. Pat. No. 7,288,638. In some embodiments, the anti-CD137 antibody is 4E9 or BMS-554271, described in U.S. Pat. No. 6,887,673. In some embodiments, the anti-CD137 antibody is an antibody disclosed in U.S. Pat. Nos. 7,214,493; 6,303,121; 6,569,997; 6,905,685; or 6,355,476. In some embodiments, the anti-CD137 antibody is 1D8 or BMS-469492; 3H3 or BMS-469497; or 3E1, described in U.S. Pat. No. 6,362,325. In some embodiments, the anti-CD137 antibody is an antibody disclosed in issued U.S. Pat. No. 6,974,863 (such as 53A2). In some embodiments, the anti-CD137 antibody is an antibody disclosed in issued U.S. Pat. No. 6,210,669 (such as 1D8, 3B8, or 3E1). In some embodiments, the antibody is Pfizer's PF-05082566 (PF-2566). In other embodiments, an anti-CD137 antibody useful for the disclosure cross-competes with the anti-CD137 antibodies disclosed herein. In some embodiments, an anti-CD137 antibody binds to the same epitope as the anti-CD137 antibody disclosed herein. In other embodiments, an anti-CD137 antibody useful in the disclosure comprises six CDRs of the anti-CD137 antibodies disclosed herein.

Anti-KIR Antibodies

Certain aspects of the present disclosure are directed to a method for treating a subject afflicted with a tumor having a high TMB status comprising administering to the subject immunotherapy, wherein the immunotherapy comprises an anti-KIR antibody or antigen-binding portion thereof. The method can further comprise measuring the TMB status of a biological sample obtained from the subject. Additionally, the disclosure contemplates administering an anti-KIR antibody or antigen-binding portion thereof to a subject identified as suitable for such therapy, e.g., based on measurement of a high TMB.

Antibodies that bind specifically to KIR block the interaction between Killer-cell immunoglobulin-like receptors (KIR) on NK cells with their ligands. Blocking these receptors facilitates activation of NK cells and, potentially, destruction of tumor cells by the latter. Examples of anti-KIR antibodies have been disclosed in Int'l Publ. Nos. WO/2014/055648, WO 2005/003168, WO 2005/009465, WO 2006/072625, WO 2006/072626, WO 2007/042573, WO 2008/084106, WO 2010/065939, WO 2012/071411 and WO/2012/160448.

One anti-KIR antibody useful in the present disclosure is lirilumab (also referred to as BMS-986015, IPH2102, or the S241P variant of 1-7F9), first described in Int'l Publ. No. WO 2008/084106. An additional anti-KIR antibody useful in the present disclosure is 1-7F9 (also referred to as IPH2101), described in Int'l Publ. No. WO 2006/003179. In one embodiment, an anti-KIR antibody for the present composition cross competes for binding to KIR with lirilumab or I-7F9. In another embodiment, an anti-KIR antibody binds to the same epitope as lirilumab or I-7F9. In other embodiments, an anti-KIR antibody comprises six CDRs of lirilumab or I-7F9.

Anti-GITR Antibodies

Certain aspects of the present disclosure are directed to a method for treating a subject afflicted with a tumor having a high TMB status comprising administering to the subject immunotherapy, wherein the immunotherapy comprises an anti-GITR antibody or antigen-binding portion thereof. The method can further comprise measuring the TMB status of a biological sample obtained from the subject. Additionally, the disclosure contemplates administering an anti-GITR antibody or antigen-binding portion thereof to a subject identified as suitable for such therapy, e.g., based on measurement of a high TMB.

Anti-GITR antibodies can be any anti-GITR antibody that binds specifically to human GITR target and activates the glucocorticoid-induced tumor necrosis factor receptor (GITR). GITR is a member of the TNF receptor superfamily that is expressed on the surface of multiple types of immune cells, including regulatory T cells, effector T cells, B cells, natural killer (NK) cells, and activated dendritic cells ("anti-GITR agonist antibodies"). Specifically, GITR activation increases the proliferation and function of effector T cells, as well as abrogating the suppression induced by activated T regulatory cells. In addition, GITR stimulation promotes anti-tumor immunity by increasing the activity of other immune cells such as NK cells, antigen presenting cells, and B cells. Examples of anti-GITR antibodies have been disclosed in Int'l Publ. Nos. WO/2015/031667, WO2015/184, 099, WO2015/026,684, WO11/028683 and WO/2006/105021, U.S. Pat. Nos. 7,812,135 and 8,388,967 and U.S. Publ. Nos. 2009/0136494, 2014/0220002, 2013/0183321 and 2014/0348841.

In one embodiment, an anti-GITR antibody useful in the present disclosure is TRX518 (described in, for example, Schaer et al. *Curr Opin Immunol.* (2012) April; 24(2): 217-224, and WO/2006/105021). In another embodiment, the anti-GITR antibody is selected from MK4166, MK1248, and antibodies described in WO 11/028683 and U.S. Pat. No. 8,709,424, and comprising, e.g., a VH chain comprising SEQ ID NO: 104 and a VL chain comprising SEQ ID NO: 105 (wherein the SEQ ID NOs are from WO11/028683 or U.S. Pat. No. 8,709,424). In certain embodiments, an anti-GITR antibody is an anti-GITR antibody that is disclosed in WO2015/031667, e.g., an antibody comprising VH CDRs 1-3 comprising SEQ ID NOs: 31, 71 and 63 of WO2015/031667, respectively, and VL CDRs 1-3 comprising SEQ ID NOs: 5, 14 and 30 of WO2015/031667. In certain embodiments, an anti-GITR antibody is an anti-GITR antibody that is disclosed in WO2015/184099, e.g., antibody Hum231 #1 or Hum231 #2, or the CDRs thereof, or a derivative thereof (e.g., pab1967, pab1975 or pab1979). In certain embodiments, an anti-GITR antibody is an anti-GITR antibody that is disclosed in JP2008278814, WO09/009116, WO2013/039954, US20140072566, US20140072565, US20140065152, or WO2015/026684, or is INBRX-110 (INHIBRx), LKZ-145 (Novartis), or MEDI-1873 (MedImmune). In certain embodiments, an anti-GITR antibody is an anti-GITR antibody that is described in PCT/US2015/033991 (e.g., an antibody comprising the variable regions of 28F3, 18E10 or 19D3). For example, an anti-GITR antibody may be an antibody comprising the following VH and VL chains or the CDRs thereof.

```
VH:
                                           (SEQ ID NO: 1)
QVQLVESGGGVVQPGRSLRLSCAASGFTFSSYGMHWVRQAPGKGLEWVAV

IWYEGSNKYYADSVKGRFTISRDNSKNTLYLQMNSLRAEDTAVYYCARGG

SMVRGDYYYGMDVWGQGTTVTVS,
and

VL:
                                           (SEQ ID NO: 2)
AIQLTQSPSSLSASVGDRVTITCRASQGISSALAWYQQKPGKAPKLLIYD

ASSLESGVPSRFSGSGSGTDFTLTISSLQPEDFATYYCQQFNSYPYTFGQ

GTKLEIK;
or

VH:
                                           (SEQ ID NO: 3)
QVQLVESGGGVVQPGRSLRLSCAASGFTFSSYGFHWVRQAPGKGLEWVAV

IWYAGSNKFYADSVKGRFTISRDNSKNTLYLQMNSLRAEDTAVYYCARGG

QLDYYYYYVMDVWGQGTTVTVSS,
and

VL:
                                           (SEQ ID NO: 4)
DIQMTQSPSSLSASVGDRVTITCRASQGISSWLAWYQQKPEKAPKSLIYA

ASSLQSGVPSRFSGSGSGTDFTLTISSLQPEDFATYYCQQYNSYPYTFGQ

GTKLEIK;
or

VH:
                                           (SEQ ID NO: 5)
VQLVESGGGVVQPGRSLRLSCAASGFTFSSYGMHWVRQAPGKGLEWVAVI

WYAGSNKYYADSVKGRFTISRDNSKNTLYLQMNSLRAEDTAVYYCARGGR

IAVAFYYSMDVWGQGTTVTVSS,
and

VL:
                                           (SEQ ID NO: 6)
DIQMTQSPSSLSASVGDRVTITCRASQGISSWLAWYQQKPEKAPKSLIYA

ASSLQSGVPSRFSGSGSGTDFTLTISSLQPEDFATYYCQQYNSYPYTFGQ

GTKLEIK.
```

In certain embodiments, an antibody comprising a pair of the above VH and VL light chains, or their CDRs, comprises a heavy chain constant region of an IgG1 isotype, either wild type or mutated, e.g., to be effectorless. In one embodiment, an anti-GITR antibody comprises the following heavy and light chains amino acid sequences:

```
heavy chain:
                                           (SEQ ID NO: 7)
QVQLVESGGGVVQPGRSLRLSCAASGFTFSSYGMHWVRQAPGKGLEWVAV

IWYEGSNKYYADSVKGRFTISRDNSKNTLYLQMNSLRAEDTAVYYCARGG

SMVRGDYYYGMDVWGQGTTVTVSSASTKGPSVFPLAPCSRSTSESTAALG

CLVKDYFPEPVTVSWNSGALTSGVHTFPAVLQSSGLYSLSSVVTVPSSNF

GTQTYTCNVDHKPSNTKVDKTVERKCCVECPPCPAPPVAGPSVFLFPPKP

KDTLMISRTPEVTCVVVDVSHEDPEVQFNWYVDGVEVHNAKTKPREEQFN

STFRVVSVLTVVHQDWLNGKEYKCKVSNKGLPAPIEKTISKTKGQPREPQ

VYTLPPSREEMTKNQVSLTCLVKGFYPSDIAVEWESNGQPENNYKTTPPM

LDSDGSFFLYSKLTVDKSRWQQGNVFSCSVMHEALHNHYTQKSLSLSPG,
and light chain:
                                           (SEQ ID NO: 8)
AIQLTQSPSSLSASVGDRVTITCRASQGISSALAWYQQKPGKAPKLLIYD

ASSLESGVPSRFSGSGSGTDFTLTISSLQPEDFATYYCQQFNSYPYTFGQ

GTKLEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC,
or
```

-continued heavy chain:
(SEQ ID NO: 9)
qvqlvesgggvvqpgrslrlscaasgftfssygmhwvrqapgkglewvav iwyegsnkyyadsvkgrftisrdnskntlylqmnslraedtavyycargg smvrgdyyygmdvwgqgttvtvssastkgpsvfplapsskstsggtaalg clvkdyfpepvtvswnsgaltsgvhtfpavlqssglyslssvvtvpsssl gtqtyicnvnhkpsntkvdkrvepkscdkthtcppcpapeaegapsvflf ppkpkdtlmisrtpevtcvvvdvshedpevkfnwyvdgvevhnaktkpre eqynstyrvvsvltvlhqdwlngkeykckvsnkalpssiektiskakgqp repqvytlppsreemtknqvsltclvkgfypsdiavewesngqpennykt tppvldsdgefflyskltvdksrwqqgnvfscsvmhealhnhytqkslsl spg,
and light chain:
(SEQ ID NO: 10)
AIQLTQSPSSLSASVGDRVTITCRASQGISSALAWYQQKPGKAPKLLIYD

ASSLESGVPSRFSGSGSGTDFTLTISSLQPEDFATYYCQQFNSYPYTFGQ

GTKLEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC.

In certain embodiments, the anti-GITR antibody cross-competes with an anti-GITR antibody described herein, e.g., TRX518, MK4166 or an antibody comprising a VH domain and a VL domain amino acid sequence described herein. In some embodiments, the anti-GITR antibody binds the same epitope as that of an anti-GITR antibody described herein, e.g., TRX518, MK4166 or an antibody comprising a VH domain and a VL domain amino acid sequence described herein. In certain embodiments, the anti-GITR antibody comprises the six CDRs of TRX518, MK4166 or those of an antibody comprising a VH domain and a VL domain amino acid sequence described herein.

Additional Antibodies

In some embodiments, the immunotherapy comprises an anti-TGFβ antibody. In certain embodiments, the anti-TGFβ antibody is an anti-TGFβ antibody disclosed in Int'l Publ. No. WO/2009/073533.

In some embodiments, the immunotherapy comprises an anti-IL-10 antibody. In certain embodiments, the anti-IL-10 antibody is an anti-IL-10 antibody disclosed in Int'l Publ. No. WO/2009/073533.

In some other embodiments, the immunotherapy comprises an anti-B7-H4 antibody. In certain embodiments, the anti-B7-H4 antibody is an anti-B7-H4 antibody disclosed in Int'l Publ. No. WO/2009/073533.

In certain embodiments, the immunotherapy comprises an anti-Fas ligand antibody. In certain embodiments, the anti-Fas ligand antibody is an anti-Fas ligand antibody disclosed in Int'l Publ. No. WO/2009/073533.

In some embodiments, the immunotherapy comprises an anti-CXCR4 antibody. In certain embodiments, the anti-CXCR4 antibody is an anti-CXCR4 antibody disclosed in U.S. Publ. No. 2014/0322208 (e.g., Ulocuplumab (BMS-936564)).

In some embodiments is the immunotherapy comprises an anti-mesothelin antibody. In certain embodiments, the anti-mesothelin antibody is an anti-mesothelin antibody disclosed in U.S. Pat. No. 8,399,623.

In some embodiments, the immunotherapy comprises an anti-HER2 antibody. In certain embodiments, the anti-HER2 antibody is Herceptin (U.S. Pat. No. 5,821,337), trastuzumab, or ado-trastuzumab emtansine (Kadcyla, e.g., WO/2001/000244).

In embodiments, the immunotherapy comprises an anti-CD27 antibody. In embodiments, the anti-CD-27 antibody is Varlilumab (also known as "CDX-1127" and "1F5"), which is a human IgG1 antibody that is an agonist for human CD27, as disclosed in, for example, U.S. Pat. No. 9,169,325.

In some embodiments, the immunotherapy comprises an anti-CD73 antibody. In certain embodiments, the anti-CD73 antibody is CD73.4.IgG2C219S.IgG1.1f.

In some embodiments, the immunotherapy comprises an anti-MICA antibody. As used herein, an anti-MICA antibody is an antibody or an antigen binding fragment thereof that specifically binds MHC class I polypeptide-related sequence A. In some embodiments, the anti-MICA antibody binds MICB in addition to MICA. In some embodiments, the anti-MICA antibody inhibits cleavage of membrane bound MICA and release of soluble MICA. In certain embodiments, the anti-MICA antibody is an anti-MICA antibody disclosed in U.S. Publ. No. 2014/004112 A1, U.S. Publ. No. 2016/046716 A1, or U.S. Publ. No. 2017/022275 A1.

In some embodiments, the immunotherapy comprises an anti-TIM3 antibody. As used herein, an anti-TIM3 antibody is an antibody or an antigen binding fragment thereof that specifically binds T-cell immunoglobulin and mucin-domain containing-3 (TIM3), also known as hepatitis A virus cellular receptor 2 (HAVCR2). In some embodiments, the anti-TIM3 antibody is capable of stimulating an immune response, e.g., an antigen-specific T cell response. In some embodiments, the anti-TIM3 antibody binds to soluble or membrane bound human or cyno TIM3. In certain embodiments, the anti-TIM3 antibody is an anti-TIM3 antibody disclosed in International Publication No. WO/2018/013818, which is incorporated by reference herein in its entirety.

Standard-of-Care Therapies for SCLC

In some embodiments, the subject has been previously treated with one or more standard-care-therapy for SCLC. In some embodiments, the subject is refractory to one or more standard-of-care therapy for SCLC. In some embodiments, the subject has showed progressive disease after one or more standard-of-care therapy for SCLC. In some embodiments, the subject has showed stable disease after one or more standard-of-care therapy for SCLC. In some embodiments, the subject is not refractory to one or more standard-of-care therapy for SCLC. In some embodiments, the subject has relapsed following one or more standard of care therapy for SCLC.

Standard-of-care therapies for different types of cancer are well known by persons of skill in the art. For example, the National Comprehensive Cancer Network (NCCN), an alliance of 21 major cancer centers in the USA, publishes the NCCN Clinical Practice Guidelines in Oncology (NCCN GUIDELINES®) that provide detailed up-to-date information on the standard-of-care treatments for a wide variety of cancers (see NCCN GUIDELINES® (2014), available at: http://www.nccn.org/professionals/physician_gls/f_guidelines.asp, last accessed Jun. 2, 2016).

Surgery, radiation therapy (RT), and chemotherapy are the three modalities commonly used to treat SCLC patients. The most commonly used initial chemotherapy regimen is etoposide (TOPOSAR® or VEPESID®) plus cisplatin (PLATINOL®), known as EP. For people with extensive-stage small cell lung cancer, chemotherapy alone using the EP regimen is the standard treatment. However, another regimen that may be used is carboplatin (PARAPLATIN®) plus irinotecan (CAMPTOSAR®).

Although SCLC is highly sensitive to initial treatments, including chemotherapy and/or radiotherapy, most patients ultimately die due to recurrence of the SCLC. Therefore, there is a particular unmet need among patients who have recurrent SCLC as there is a lack of an effective treatment after first line therapy.

Pharmaceutical Compositions and Dosages

Therapeutic agents of the present disclosure can be constituted in a composition, e.g., a pharmaceutical composition containing an antibody and/or a cytokine and a pharmaceutically acceptable carrier. As used herein, a "pharmaceutically acceptable carrier" includes any and all solvents, dispersion media, coatings, antibacterial and antifungal agents, isotonic and absorption delaying agents, and the like that are physiologically compatible. In one embodiment, the carrier for a composition containing an antibody is suitable for intravenous, intramuscular, subcutaneous, parenteral, spinal or epidermal administration (e.g., by injection or infusion), whereas the carrier for a composition containing an antibody and/or a cytokine is suitable for non-parenteral, e.g., oral, administration. In some embodiments, the subcutaneous injection is based on Halozyme Therapeutics' ENHANZE® drug-delivery technology (see U.S. Pat. No. 7,767,429, which is incorporated by reference herein in its entirety). ENHANZE® uses a co-formulation of an antibody with recombinant human hyaluronidase enzyme (rHuPH20), which removes traditional limitations on the volume of biologics and drugs that can be delivered subcutaneously due to the extracellular matrix (see U.S. Pat. No. 7,767,429). A pharmaceutical composition of the disclosure can include one or more pharmaceutically acceptable salts, anti-oxidant, aqueous and non-aqueous carriers, and/or adjuvants such as preservatives, wetting agents, emulsifying agents and dispersing agents. Therefore, in some embodiments, the pharmaceutical composition for the present disclosure can further comprise recombinant human hyaluronidase enzyme, e.g., rHuPH20.

Dosage regimens are adjusted to provide the optimum desired response, e.g., a maximal therapeutic response and/or minimal adverse effects. In some embodiments, the anti-PD-1 antibody, the anti-PD-L1 antibody, and/or the anti-CTLA-4 antibody is administered at a weight-based dose. For administration of an anti-PD-1 antibody, as a monotherapy or in combination with another anti-cancer agent (e.g., in combination with an anti-CTLA-4 antibody), the dosage can range from about 0.01 to about 20 mg/kg, from about 0.1 to about 10 mg/kg, from about 0.1 to about 5 mg/kg, from about 0.01 mg/kg to about 5 mg/kg, from about 1 to about 5 mg/kg, from about 2 to about 5 mg/kg, from about 1 to about 3 mg/kg, from about 7.5 to about 12.5 mg/kg, or from about 0.1 to about 30 mg/kg of the subject's body weight. For example, dosages can be about 0.1, about 0.3, about 1, about 2, about 3, about 5, or about 10 mg/kg body weight, and more preferably, 0.3, 1, 2, 3, or 5 mg/kg body weight. In certain embodiments, the dosage of the anti-PD-1 antibody is 3 mg/kg body weight. The dosing schedule is typically designed to achieve exposures that result in sustained receptor occupancy (RO) based on typical pharmacokinetic properties of an antibody An exemplary treatment regime entails administration about once per week, once about every 2 weeks, once about every 3 weeks, once about every 4 weeks, once about a month, once about every 3-6 months or longer. In certain embodiments, an anti-PD-1 antibody such as nivolumab is administered to the subject once about every 2 weeks. In other embodiments, the antibody is administered once about every 3 weeks. The dosage and scheduling can change during a course of treatment. For example, a dosing schedule for anti-PD-1 monotherapy can comprise administering the antibody: (i) about every 2 weeks in about 6-week cycles; (ii) about every 4 weeks for about six dosages, then about every three months; (iii) about every 3 weeks; (iv) about 3 mg/kg to about 10 mg/kg once followed by about 1 mg/kg every about 2-3 weeks. Considering that an IgG4 antibody typically has a half-life of 2-3 weeks In one embodiment, a dosage regimen for an anti-PD-1 antibody or an anti-PD-L1 antibody of the disclosure comprises about 0.3-1 mg/kg body weight, about 5 mg/kg body weight, 1-5 mg/kg body weight, or about 1-about 3 mg/kg body weight via intravenous administration, with the antibody being given every about 14-21 days in up to about 6-week or about 12-week cycles until complete response or confirmed progressive disease. In certain embodiments, an anti-PD-1 antibody monotherapy is administered at 3 mg/kg every 2 weeks until progressive disease or unacceptable toxicity. In some embodiments, the antibody treatment, or any combination treatment disclosed herein, is continued for at least about 1 month, at least about 3 months, at least about 6 months, at least about 9 months, at least about 1 year, at least about 18 months, at least about 24 months, at least about 3 years, at least about 5 years, or at least about 10 years.

When used in combinations with other cancer agents (e.g., in combination with an anti-CTLA-4 antibody), the dosage of an anti-PD-1 antibody can be lowered compared to the monotherapy dose. Dosages of nivolumab that are lower than the typical 3 mg/kg, but not less than 0.001 mg/kg, are subtherapeutic dosages. The subtherapeutic doses of an anti-PD-1 antibody used in the methods herein are higher than 0.001 mg/kg and lower than 3 mg/kg. In some embodiments, a subtherapeutic dose is about 0.001 mg/kg to about 1 mg/kg, about 0.01 mg/kg to about 1 mg/kg, about 0.1 mg/kg to about 1 mg/kg, or about 0.001 mg/kg to about 0.1 mg/kg body weight. In some embodiments, the subtherapeutic dose is at least about 0.001 mg/kg, at least about 0.005 mg/kg, at least about 0.01 mg/kg, at least about 0.05 mg/kg, at least about 0.1 mg/kg, at least about 0.5 mg/kg, or at least about 1.0 mg/kg body weight. Receptor-occupancy data from 15 subjects who received 0.3 mg/kg to 10 mg/kg dosing with nivolumab indicate that PD-1 occupancy appears to be dose-independent in this dose range. Across all doses, the mean occupancy rate was 85% (range, 70% to 97%), with a mean plateau occupancy of 72% (range, 59% to 81%). In some embodiments, 0.3 mg/kg dosing can allow for sufficient exposure to lead to maximal biologic activity. Receptor-occupancy data from 15 subjects who received 0.3 mg/kg to 10 mg/kg dosing with nivolumab indicate that PD-1 occupancy appears to be dose-independent in this dose range. Across all doses, the mean occupancy rate was 85% (range, 70% to 97%), with a mean plateau occupancy of 72% (range, 59% to 81%) (Brahmer et al., J Clin Oncol 28:3167-75 2010). Thus, 0.3 mg/kg dosing can allow for sufficient exposure to lead to maximal biologic activity.

Although higher nivolumab monotherapy dosing up to 10 mg/kg every two weeks has been achieved without reaching the maximum tolerated does (MTD), the significant toxicities reported in other trials of checkpoint inhibitors plus anti-angiogenic therapy (see, e.g., Johnson et al. (2013)

*Cancer Immunol Res* 1:373-77; Rini et al. (2011) *Cancer* 117:758-67) support the selection of a nivolumab dose lower than 10 mg/kg.

In certain embodiments, the dose of an anti-PD-1 antibody (or an anti-PD-L1 antibody) is a fixed dose in a pharmaceutical composition. In other embodiments, the method of the present disclosure can be used with a flat dose (a dose given to a patient irrespective of the body weight of the patient). For example, a flat dose of nivolumab can be about 240 mg. For example, a flat dose of pembrolizumab can be about 200 mg. In embodiments, the anti-PD-1 antibody is administered at a dose of about 240 mg. In embodiments, the anti-PD-1 antibody is administered at a dose of about 360 mg. In embodiments, the anti-PD-1 antibody is administered at a dose of about 480 mg. In one embodiment, 360 mg of the anti-PD-1 antibody is administered once every 3 weeks. In another embodiment, 480 mg of the anti-PD-1 antibody is administered once every 4 weeks.

Ipilimumab (YERVOY®) is approved for the treatment of melanoma at 3 mg/kg given intravenously once every 3 weeks for 4 doses. Thus, in some embodiments, about 3 mg/kg is the highest dosage of ipilimumab used in combination with the anti-PD-1 antibody though, in certain embodiments, an anti-CTLA-4 antibody such as ipilimumab can be dosed within the range of about 0.3 to about 10 mg/kg, about 0.5 to about 10 mg/kg, about 0.5 to about 5 mg/kg, or about 1 to about 5 mg/kg body weight about every two or three weeks when combined with nivolumab. In other embodiments, ipilimumab is administered on a different dosage schedule from nivolumab. In some embodiments, ipilimumab is administered about every week, about every two weeks, about every three weeks, about every 4 weeks, about every five weeks, about every six weeks, about every seven weeks, about every eight weeks, about every nine weeks, about every ten weeks, about every eleven weeks, about every twelve weeks or about every fifteen weeks. Dosages of ipilimumab that are lower than the typical 3 mg/kg every 3 weeks, but not less than 0.001 mg/kg, are subtherapeutic dosages. The subtherapeutic doses of an anti-CTLA-4 antibody used in the methods herein are higher than 0.001 mg/kg and lower than 3 mg/kg. In some embodiments, a subtherapeutic dose is about 0.001 mg/kg to about 1 mg/kg, about 0.01 mg/kg to about 1 mg/kg, about 0.1 mg/kg to about 1 mg/kg, or about 0.001 mg/kg to about 0.1 mg/kg body weight. In some embodiments, the subtherapeutic dose is at least about 0.001 mg/kg, at least about 0.005 mg/kg, at least about 0.01 mg/kg, at least about 0.05 mg/kg, at least about 0.1 mg/kg, at least about 0.5 mg/kg, or at least about 1.0 mg/kg body weight. It has been shown that combination dosing of nivolumab at 3 mg/kg and ipilimumab at 3 mg/kg exceeded the MTD in a melanoma population, whereas a combination of nivolumab at 1 mg/kg plus ipilimumab at 3 mg/kg or nivolumab at 3 mg/kg plus ipilimumab at 1 mg/kg was found to be tolerable in melanoma patients (Wolchok et al., *N Engl J Med* 369(2):122-33(2013)). Accordingly, although nivolumab is tolerated up to 10 mg/kg given intravenously every 2 weeks, in certain embodiments doses of the anti-PD-1 antibody do not exceed about 3 mg/kg when combined with ipilimumab. In certain embodiments, based on risk-benefit and PK-PD assessments, the dosage used comprises a combination of nivolumab at about 1 mg/kg plus ipilimumab at about 3 mg/kg, nivolumab at about 3 mg/kg plus ipilimumab at about 1 mg/kg, or nivolumab at about 3 mg/kg plus ipilimumab at about 3 mg/kg is used, each administered at a dosing frequency of once about every 2-4 weeks, in certain embodiments, once about every 2 weeks or once about every 3 weeks. In certain other embodiments, nivolumab is administered at a dosage of about 0.1 mg/kg, about 0.3 mg/kg, about 1 mg/kg, about 2 mg/kg, about 3 mg/kg, or about 5 mg/kg in combination with ipilimumab administered at a dosage of about 0.1 mg/kg, about 0.3 mg/kg, about 1 mg/kg, about 2 mg/kg, about 3 mg/kg, or about 5 mg/kg, once about every 2 weeks, once about every 3 weeks, or once about every 4 weeks.

In certain embodiments, the combination of an anti-PD-1 antibody and an anti-CTLA-4 antibody is administered intravenously to the subject in an induction phase about every 2 or 3 weeks for 1, 2, 3 or 4 administrations. In certain embodiments, the combination of nivolumab and ipilimumab is administered intravenously in the induction phase about every 2 weeks or about every 3 weeks for about 4 administrations. The induction phase is followed by a maintenance phase during which only the anti-PD-1 antibody is administered to the subject at a dosage of about 0.1 mg/kg, about 0.3 mg/kg, about 1 mg/kg, about 2 mg/kg, about 3 mg/kg, about 5 mg/kg, or about 10 mg/kg about every two or three weeks for as long as the treatment proves efficacious or until unmanageable toxicity or disease progression occurs. In certain embodiments, nivolumab is administered during the maintenance phase at a dose of about 3 mg/kg body about every 2 weeks. In some embodiments, the anti-PD-1 antibody is administered at a dose of about 3 mg/kg (or at a flat dose of 240 mg) once about every two weeks, and the anti-CTLA-4 antibody is administered at a dose of 1 mg/kg once about every 6 weeks. In some embodiments, the anti-PD-1 antibody is administered at a flat dose (e.g., 240 mg or 480 mg) and the anti-CTLA-4 antibody is administered at a weight based dose (e.g., 1 mg/kg or 3 mg/kg).

The antibodies disclosed herein can be administered according to a "treatment cycle" or a "cycle" (which terms are used interchangeably herein). As used herein, the term "cycle" refers to a course of treatment that is repeated on a regular schedule with periods of rest in between. For example, treatment given for one week followed by three weeks of rest is a treatment cycle. In one embodiment, the anti-PD-1 antibody and/or anti-CTLA-4 antibody is administered for at least 1, 2, 3, 4, 5, 6, 7, 8, 9, or 10 cycles. In a particular embodiment, the administration of the anti-PD-1 antibody and the anti-CTLA-4 antibody was repeated four times (4 cycles).

In certain embodiments, the anti-PD-1 antibody (or the anti-CTLA-4 antibody) and the anti-CTLA-4 antibody is formulated as a single composition, wherein the dose of the anti-PD1 antibody and the dose of the anti-CTLA-4 antibody are combined at a ratio of 1:50, 1:40, 1:30, 1:20, 1:10. 1:5, 1:3, 1:1, 3:1, 5:1, 10:1, 20:1, 30:1, 40:1, or 50:1. In other embodiments, the dose of the anti-CTLA-4 antibody is a fixed dose. In some embodiments, the ratio of the anti-PD-1 antibody or the anti-PD-L1 antibody to the anti-CTLA-4 antibody is at least about 1:1, about 1:2, about 1:3, about 1:4, about 1:5, about 1:6, about 1:7, about 1:8, about 1:9, about 1:10, about 1:15, about 1:20, about 1:30, about 1:40, about 1:50, about 1:60, about 1:70, about 1:80, about 1:90, about 1:100, about 1:120, about 1:140, about 1:160, about 1:180, about 1:200, about 200:1, about 180:1, about 160:1, about 140:1, about 120:1, about 100:1, about 90:1, about 80:1, about 70:1, about 60:1, about 50:1, about 40:1, about 30:1, about 20:1, about 15:1, about 10:1, about 9:1, about 8:1, about 7:1, about 6:1, about 5:1, about 4:1, about 3:1, or about 2:1 mg.

In certain embodiments, the dose of the anti-CTLA-4 antibody is a flat dose, which is given to a patient irrespective of the body weight. In a specific embodiment, the flat dose of the anti-CTLA-4 antibody is about 80 mg. In some embodiments, the anti-PD-1 antibody, or an anti-PD-L1 antibody is administered at a flat dose as a monotherapy. In embodiments, the anti-PD-1 antibody or an anti-PD-L1 antibody is administered as a flat dose in combination with an anti-CTLA-4 antibody. In embodiments, the flat dose of the anti-PD-1 antibody or an anti-PD-L1 antibody is a dose of at least about 100-600 mg, such as, at least about 200-300 mg, at least about 400-500 mg, or at least about 240 mg or at least about 480 mg, such as at least about 60 mg, at least about 80 mg, at least about 100 mg, at least about 120 mg, at least about 140 mg, at least about 160 mg, at least about 180 mg, at least about 200 mg, at least about 220 mg, at least about 240 mg, at least about 260 mg, at least about 280 mg, at least about 320 mg, at least about 360 mg, at least about 400 mg, at least about 440 mg, at least about 480 mg, at least about 520 mg, at least bout 560 mg, at least about 600 mg, or at least about 660 mg, or at least about 720 mg. In some embodiments, the flat dose of the anti-PD-1 antibody or an anti-PD-L1 antibody is a dose of at least about 600-1200 mg. In some embodiments, flat dose of the anti-PD-1 antibody or an anti-PD-L1 antibody is a dose of at least about 600 mg, at least about 640 mg, at least about 680 mg, at least about 720 mg, at least about 760 mg, at least about 800 mg, at least about 840 mg, at least about 880 mg, at least about 920 mg, at least about 960 mg, at least about 1000 mg, at least about 1040 mg, at least about 1080 mg, at least about 1120 mg, at least about 1160 mg, or at least about 1200 mg. In some embodiments, the anti-PD-1 antibody or antigen-binding portion thereof is administered at a dose of at least about 240 mg or at least about 480 mg once about every 2 or 4 weeks. In some embodiments, the anti-PD-L1 antibody or antigen-binding portion thereof is administered at a dose of at least about 240 mg or at least about 480 mg once about every 2 or 4 weeks. In some embodiments, the anti-PD-1 antibody or the anti-PD-L1 antibody is administered at a dose of at least about 720 mg. In some embodiments, the anti-PD-1 antibody or the anti-PD-L1 antibody is administered at a dose of at least about 960 mg. In some embodiments, the anti-PD-1 antibody or the anti-PD-L1 antibody is administered at a dose of at least about 1200 mg.

In other embodiments, the anti-PD-1 antibody or antigen-binding portion thereof is administered at a dose higher than, i.e., at least about, 240 mg. When used in combinations with other cancer agents, the dosage of an anti-PD-1 antibody can be lowered compared to the monotherapy dose. For example, a dosage of nivolumab that is significantly lower than the typical 3 mg/kg every 3 weeks, for instance 0.1 mg/kg or less every 3 or 4 weeks, is regarded as a subtherapeutic dosage.

In some embodiments, the flat doses of an anti-PD-1 antibody and an anti-CTLA-4 antibody in combination are about 60 mg to about 80 mg, e.g., about 60 mg, about 65 mg, about 70 mg, about 75 mg, or about 80 mg, for anti-PD-1 antibody and about 180 mg to about 240 mg, e.g., about 180 mg, about 190 mg, about 200 mg, about 210 mg, about 220 mg, about 230 mg, or about 240 mg for anti-CTLA-4 antibody. In other embodiments, the flat doses of an anti-PD-1 antibody and an anti-CTLA-4 antibody in combination are about 80 mg, for anti-PD-1 and about 240 mg for anti-CTLA-4 antibody. The anti-PD-1 antibody and the anti-CTLA-4 antibody can be in the same formulation or in separate formulations.

For combination of nivolumab with other anti-cancer agents, these agents are preferably administered at their approved dosages. Treatment is continued as long as clinical benefit is observed or until unacceptable toxicity or disease progression occurs. Nevertheless, in certain embodiments, the dosages of these anti-cancer agents administered are significantly lower than the approved dosage, i.e., a sub-therapeutic dosage, of the agent is administered in combination with the anti-PD-1 antibody or an anti-PD-L1 antibody. The anti-PD-1 antibody or anti-PD-L1 antibody can be administered at the dosage that has been shown to produce the highest efficacy as monotherapy in clinical trials, e.g., about 3 mg/kg of nivolumab administered once every three weeks (Topalian et al., *N Engl J Med* 366:2443-54 (2012a); Topalian et al., *Curr Opin Immunol* 24:207-12 (2012b)), or at a significantly lower dose, i.e., at a subtherapeutic dose. In certain embodiments, the anti-PD-1 antibody is administered at about 3 mg/kg once about every three weeks.

Dosage and frequency vary depending on the half-life of the antibody in the subject. In general, human antibodies show the longest half-life, followed by humanized antibodies, chimeric antibodies, and non-human antibodies. The dosage and frequency of administration can vary depending on whether the treatment is prophylactic or therapeutic. In prophylactic applications, a relatively low dosage is typically administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patient can be administered a prophylactic regime.

In one embodiment, a subject treated with an anti-PD-1 antibody and an anti-CTLA-4 antibody in combination can be further treated with an anti-PD-1 antibody monotherapy. In some embodiments, a subject is treated with the flat doses of an anti-PD-1 antibody and an anti-CTLA-4 antibody in combination that are about 60 mg to about 80 mg, e.g., about 60 mg, about 65 mg, about 70 mg, about 75 mg, or about 80 mg, for anti-PD-1 antibody and about 180 mg to about 240 mg, e.g., about 180 mg, about 190 mg, about 200 mg, about 210 mg, about 220 mg, about 230 mg, or about 240 mg for anti-CTLA-4 antibody, followed by an anti-PD-1 monotherapy, e.g., about 3 mg/kg or about 60 to about 80 mg, e.g., about 60 mg, about 65 mg, about 70 mg, about 75 mg, or about 80 mg. In other embodiments, a subject is administered with the flat doses of an anti-PD-1 antibody and an anti-CTLA-4 antibody in combination that are about 80 mg, for anti-PD-1 and about 240 mg for anti-CTLA-4 antibody, followed by an anti-PD-1 antibody monotherapy, about 3 mg/kg or about 60 mg to about 80 mg, e.g., about 60 mg, about 65 mg, about 70 mg, about 75 mg, or about 80 mg.

Actual dosage levels of the active ingredients in the pharmaceutical compositions of the present disclosure can be varied so as to obtain an amount of the active ingredient which is effective to achieve the desired therapeutic response for a particular patient, composition, and mode of administration, without being unduly toxic to the patient. The selected dosage level will depend upon a variety of pharmacokinetic factors including the activity of the particular compositions of the present disclosure employed, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts. A composition of the present disclosure can be administered via one or more routes of administration using one or more of a variety of methods well known in the art. As will be appreciated by the skilled artisan, the route and/or mode of administration will vary depending upon the desired results.

Kits

Also within the scope of the present disclosure are kits comprising an anti-PD-1 antibody and/or an anti-CTLA-4 antibody for therapeutic uses. Kits typically include a label indicating the intended use of the contents of the kit and instructions for use. The term label includes any writing, or recorded material supplied on or with the kit, or which otherwise accompanies the kit. Accordingly, this disclosure provides a kit for treating a subject afflicted with a tumor, the kit comprising: (a) a dosage ranging from 0.1 to 10 mg/kg body weight of an antibody or an antigen-binding portion thereof that specifically binds to the PD-1 receptor and inhibits PD-1 activity ("an anti-PD-1 antibody"); and (b) instructions for using the anti-PD-1 antibody in the methods disclosed herein. The disclosure further provides a kit for treating a subject afflicted with a tumor derived from an SCLC, the kit comprising: (a) a dosage ranging from 0.1 to 10 mg/kg body weight of an anti-PD-1 antibody, (b) a dosage ranging from 0.1 to 10 mg/kg body weight of an anti-CTLA-4 antibody, and (c) instructions for using the anti-PD-1 antibody and the anti-CTLA-4 antibody in the methods disclosed herein. In some embodiments, this disclosure provides a kit for treating a subject afflicted with a tumor derived from an SCLC, the kit comprising: (a) a dosage ranging from 200 mg to 800 mg of an anti-PD-1 antibody or a dosage ranging from 200 mg to 1800 mg of an anti-PD-L1 antibody; (b) instructions for using the anti-PD-1 antibody or the anti-PD-L1 antibody in the methods disclosed herein. In some embodiments, this disclosure provides a kit for treating a subject afflicted with a tumor derived from an SCLC, the kit comprising: (a) a dosage ranging from 200 mg to 800 mg of an anti-PD-1 antibody or a dosage ranging from 200 mg to 1800 mg of an anti-PD-L1 antibody; (b) a dosage ranging from 80 mg to 800 mg of an anti-CTLA-4 antibody; (c) instructions for using (a) the anti-PD-1 antibody or the anti-PD-L1 antibody and (b) the anti-CTLA-4 antibody in the methods disclosed herein. In certain embodiments, the tumor is lung cancer, e.g., SCLC.

In certain preferred embodiments for treating human patients, the kit comprises an anti-human PD-1 antibody disclosed herein, e.g., nivolumab or pembrolizumab. In certain preferred embodiments for treating human patients, the kit comprises an anti-human PD-L1 antibody disclosed herein, e.g., atezolizumab, durvalumab, or avelumab. In certain preferred embodiments for treating human patients, the kit comprises an anti-human CTLA-4 antibody disclosed herein, e.g., ipilimumab, tremelimumab, MK-1308, or AGEN-1884.

In some embodiments, the kit further comprises a cytokine or a variant thereof. In certain embodiments the kit comprises (a) an anti-PD-1 antibody or an anti-PD-L1 antibody, (b) an anti-CTLA-4 antibody, and (c) a CD122 agonist.

In some embodiments, the kit further includes a comprehensive genomic profiling assay disclosed herein. In some embodiments, the kit includes a FOUNDATIONONE® CDX™ genomic profiling assay. In some embodiments, the kit further includes instructions to administer the immunotherapy, e.g., the anti-PD-1 antibody, the anti-PD-L1 antibody, the anti-CTLA-4 antibody, and/or the cytokine, to a subject identified as having a high TMB status, according to the methods disclosed herein. In other embodiments, the kit further includes instructions to administer (a) the anti-PD-1 antibody or the anti-PD-L1 antibody, (b) the anti-CTLA-4 antibody, and (c) the cytokine, e.g., the CD122 agonist, to a subject identified as having a high TMB status, according to the methods disclosed herein.

All of the references cited above, as well as all references cited herein, are incorporated herein by reference in their entireties.

The following examples are offered by way of illustration and not by way of limitation.

EXAMPLES

Example 1

Patients with recurrent SCLC have limited treatment options and poor survival. Initial results from a clinical trial of patients with SCLC showed durable responses and encouraging survival with nivolumab alone or in combination with ipilimumab. Twenty-six percent of patients receiving a combination of nivolumab and ipilimumab had overall survival rates over 2 years, as compared to 14% of patients receiving nivolumab monotherapy. These data supported inclusion of nivolumab with or without ipilimumab in NCCN guidelines for treatment of SCLC.

Tumor PD-L1 expression is uncommon in SCLC, and responses have been observed regardless of PD-L1 status. Improved biomarkers are needed for immunotherapy in SCLC. Previously, subjects having a high TMB were found to have higher rates of progression free survival (PFS) following treatment with nivolumab monotherapy as compared to subjects having low or medium TMB. SCLC is almost exclusively found in patients with history of smoking and is characterized by high TMB. An association between TMB and efficacy has been seen with nivolumab in NSCLC and bladder cancer, and with ipilimumab in melanoma. High TMB may be associated with enhanced benefit from nivolumab±ipilimumab in SCLC. The present study explores the use of tumor mutation burden (TMB) as a predictive biomarker for nivolumab with or without ipilimumab in SCLC.

Study Design

Subjects were selects who had previously been diagnosed with SCLC, and who had previously received at least one prior platinum-containing regimen (FIG. 23). Non-randomized and randomized (3:2) patients received either (1) a nivolumab monotherapy comprising 3 mg/kg nivolumab administered by IV every two weeks until disease progression or unacceptable toxicity; or (2) nivolumab/ipilimumab combination therapy comprising 1 mg/kg nivolumab and 3 mg/kg ipilimumab administered by IV every three weeks for four cycles, followed by nivolumab monotherapy of 3 mg/kg nivolumab administered by IV every two weeks until disease progression or unacceptable toxicity.

The primary objective was to measure the objective response rate (ORR) by per RECIST v1.1. Secondary objectives included monitoring safety, overall survival (OS), progression free survival (PFS), and duration of response (DOR). Prespecified exploratory objectives included biomarker analysis and health status using the EQ-5D instrument.

TMB was determined by whole exome sequencing, using an Illumina HiSeq 2500 using 2×100-bp paired-end reads, and calculated as the total number of nonsynonymous missense mutations in the tumor. For exploratory analyses, patients were divided into 3 subgroups based on TMB tertile.

Baseline

Figure 2:
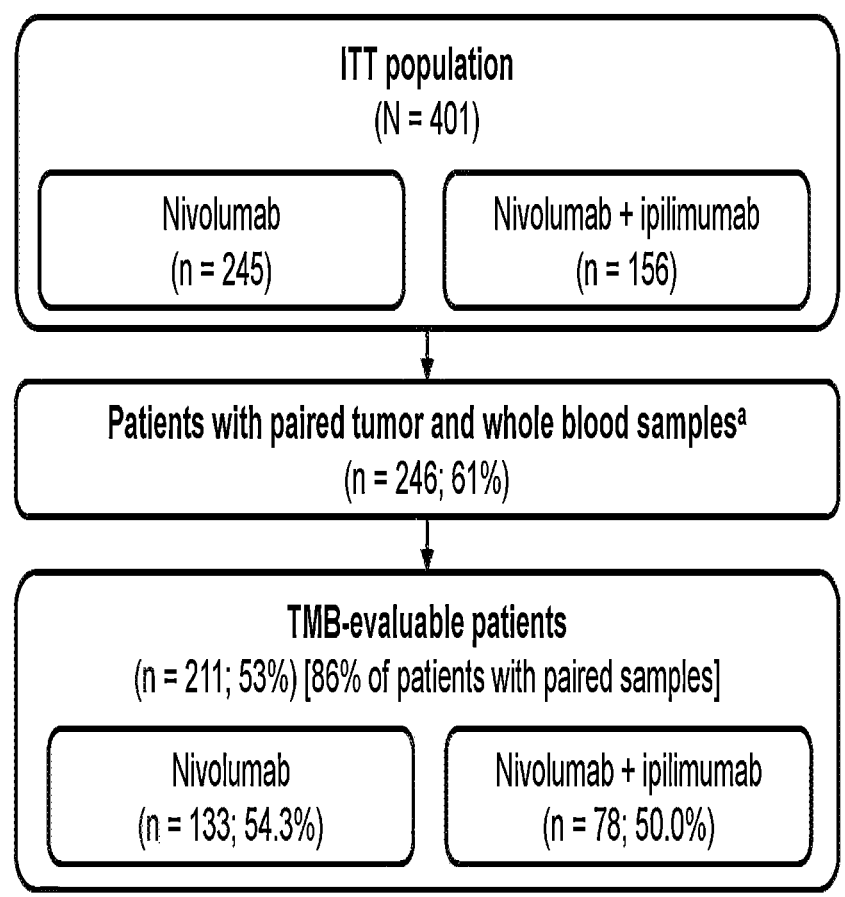
FIG. 2 is a schematic representation illustrating the methods and sample flow for exploratory TMB analysis. $^a$For germline sequencing.

A total of 245 subjects were included (ITT) for nivolumab monotherapy, of which 133 were TMB evaluable (Table 15 and FIG. 2). A total of 156 subjects were included (ITT) for nivolumab/ipilimumab combination therapy, of which 78 were TMB evaluable (Table 15 and FIG. 2).

TABLE 15

Baseline Characteristics

| | Nivolumab | | Nivolumab + ipilimumab | |
|---|---|---|---|---|
| | ITT (n = 245) | TMB-evaluable (n = 133) | ITT (n = 156) | TMB-evaluable (n = 78) |
| Age, median (range), years | 63 (29-83) | 63 (29-83) | 65 (37-91) | 65 (37-80) |
| Male, n (%) | 60 | 59 | 61 | 67 |
| Smoking status, % | | | | |
| Current/former smoker | 94 | 95 | 94 | 94 |
| Never smoker | 5 | 5 | 5 | 6 |
| ECOG PS, % | | | | |
| 0 | 30 | 32 | 31 | 30 |
| 1 | 70 | 68 | 68 | 69 |
| Tumor PD-L1 expression, % | | | | |
| ≥1% | 10 | 13 | 12 | 10 |
| <1% | 61 | 67 | 58 | 65 |
| Unknown | 29 | 20 | 30 | 24 |
| Study cohort, % | | | | |
| Non-randomized | 40 | 38 | 39 | 32 |
| Randomized | 60 | 62 | 61 | 68 |

Results

Progression free survival (PFS; FIGS. 3A and 3C) and overall survival (OS; FIGS. 3B and 3D) were comparable between the ITT patients and the subset that was TMB-evaluable for nivolumab monotherapy (FIGS. 3A and 3B) and nivolumab/ipilimumab combination therapy (FIGS. 3C and 3D). ORR in ITT and TMB-evaluable patients, respectively, was 11.4% and 11.3% with nivolumab monotherapy and 21.8% and 28.2% with nivolumab/ipilimumab combination therapy. TMB distribution for patients receiving nivolumab monotherapy or nivolumab/ipilimumab combination therapy are shown in FIG. 4A. When pooled (FIG. 4B), the distribution of the total missense mutations in the SCLC cohort was comparable to the distribution of total missense mutations in a recent non-small cell lung cancer (NSCLC) study (FIG. 4C).

Figure 5:
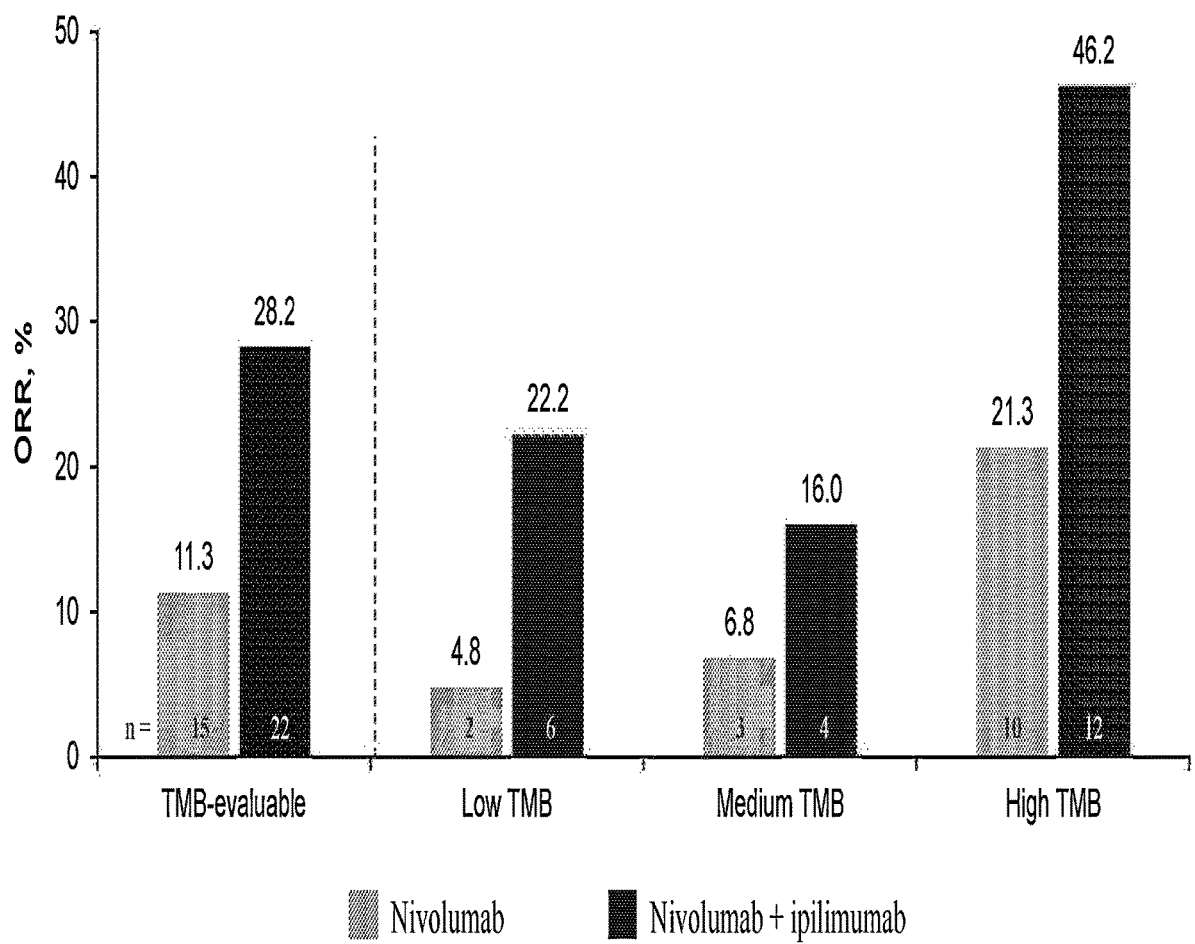
FIG. 5 is a bar graph showing the overall response rate (ORR) for all TMB-evaluable subjects treated with an anti-PD-1 antibody, e.g., nivolumab or an anti-PD-1 antibody, e.g., nivolumab and an anti-CTLA-4 antibody, e.g., ipilimumab and for the same subjects stratified by TMB status (low, medium, or high).

Overall response rate (ORR) was higher in TMB-evaluable subjects administered the nivolumab/ipilimumab combination therapy (28.2%) than in subjects administered nivolumab monotherapy (11.3%) (FIG. 5). When stratified by TMB, the greatest effect was observed for subjects having a high TMB. Subjects with a low TMB treated with nivolumab monotherapy or ipilimumab monotherapy showed ORRs of about 4.8% and 22.2%, respectively. Subjects with a medium TMB treated with nivolumab monotherapy or ipilimumab monotherapy showed ORRs of about 6.8% and 16.0%, respectively. Subjects with a high TMB treated with nivolumab monotherapy or ipilimumab monotherapy showed ORRs of about 21.3% and 46.2%, respectively.

Figure 6A:
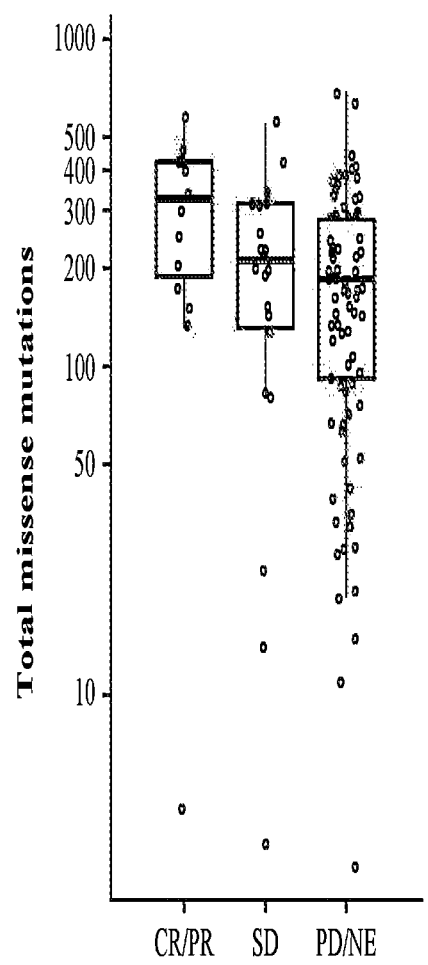
FIGS. 6A-6B are graphical representations of the TMB distribution for subjects treated with either an anti-PD-1 antibody, e.g., nivolumab monotherapy (FIG. 6A) or a combination therapy comprising an anti-PD-1 antibody, e.g., nivolumab and an anti-CTLA-4 antibody, e.g., ipilimumab (FIG. 6B), wherein the subjects are stratified by best overall response. CR=complete response; PR=partial response; SD=stable disease; PD=progressive disease; NE=not evaluated.
Figure 6B:
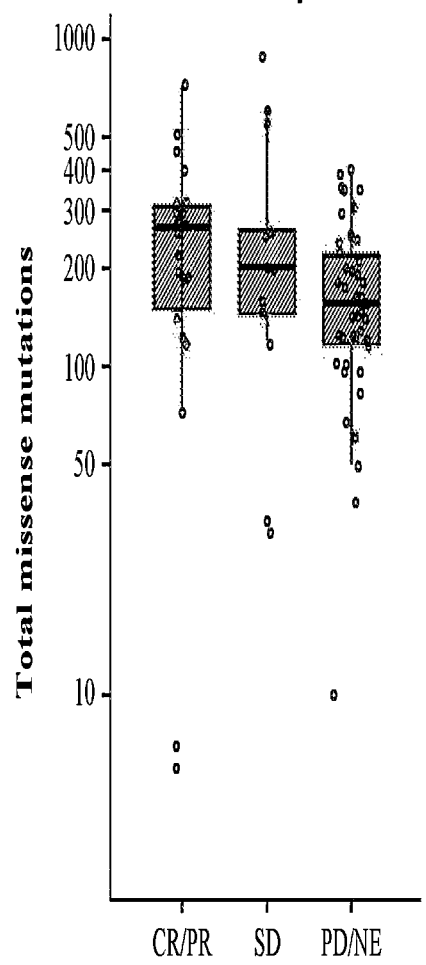

In general, subjects experiencing a better response had a higher number of missense tumor mutations. Subjects administered nivolumab monotherapy experiencing a complete response (CR) or a partial response (PR) had an average of 325 missense mutations, those experiencing stable disease had an average of 211.5 missense mutations, and those experiencing stable disease had an average of 185.5 missense mutations (FIG. 6A). Subjects administered nivolumab/ipilimumab combination therapy experiencing a complete response (CR) or a partial response (PR) had an average of 266 missense mutations, those experiencing stable disease had an average of 202 missense mutations, and those experiencing stable disease had an average of 156 missense mutations (FIG. 6B).

Figure 7B:
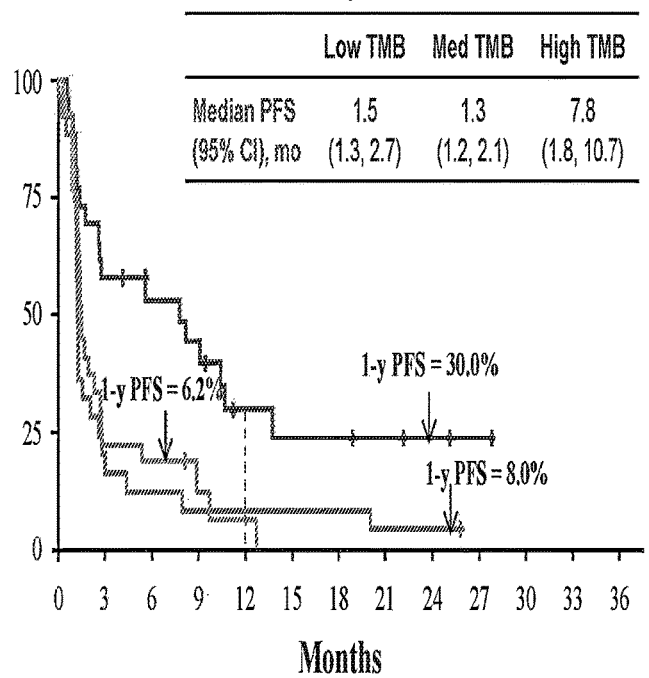

In addition, subjects with a high TMB showed increased PFS following treatment with nivolumab monotherapy (FIG. 7A) or nivolumab/ipilimumab combination therapy (FIG. 7B) as compared to subjects having a low or medium TMB. For nivolumab monotherapy, the average PFS was about 1.3% for low TMB and medium TMB subjects and about 1.4% for high TMB subjects, and the PFS at 1 year was 21.2% for high TMB subjects compared to only 3.15 for medium TMB (FIG. 7A). For nivolumab/ipilimumab combination therapy, the average PFS was about 1.5% for low TMB subjects, 1.3% for medium TMB subjects, and about 7.8% for high TMB subjects, and the PFS at 1 year was about 30% for high TMB subjects compared to about 8.0% and 6.2% for medium and low TMB subjects, respectively (FIG. 7B).

Figure 8B:
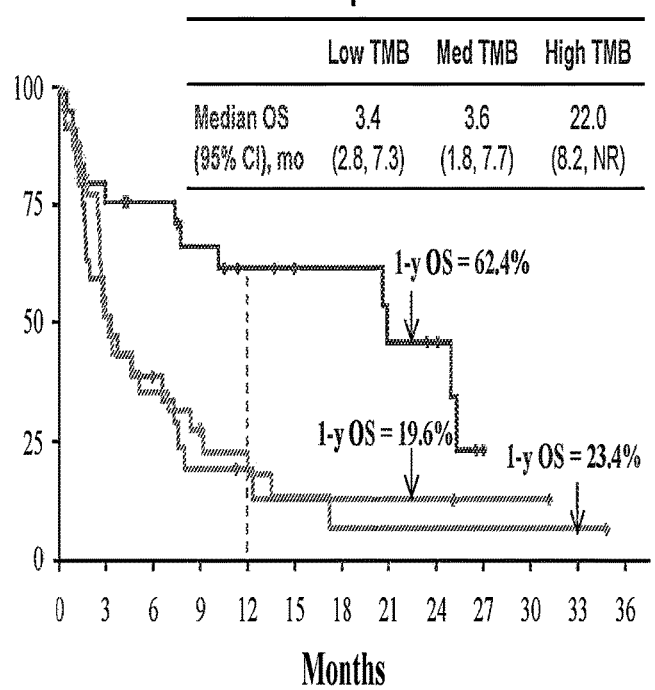

Similarly, subjects with a high TMB showed increased OS following treatment with nivolumab monotherapy (FIG. 8A) or nivolumab/ipilimumab combination therapy (FIG. 8B) as compared to subjects having a low or medium TMB. For nivolumab monotherapy, the median OS was about 3.1% for low TMB subjects, about 3.9% for medium TMB subjects, and about 5.4% for high TMB subjects, and the OS at 1 year was 35.2% for high TMB subjects compared to about 26.0% for medium TMB and 22.1% for low TMB subjects (FIG. 8A). For nivolumab/ipilimumab combination therapy, the median OS was about 3.4% for low TMB subjects, 3.6% for medium TMB subjects, and about 22% for high TMB subjects, and the OS at 1 year was about 62.4% for high TMB subjects compared to about 19.6% and 23.4% for medium and low TMB subjects, respectively (FIG. 8B).

All publications, patents, and patent applications disclosed herein are incorporated by reference to the same extent as if each individual publication, patent or patent application was specifically and individually indicated to be incorporated by reference.

This application claims the benefit of U.S. Provisional Application Nos. 62/572,514, filed Oct. 15, 2017, and 62/650,654, filed Mar. 30, 2018, which are incorporated by reference herein in their entireties.

What is claimed is:

1. A method for treating a subject afflicted with a tumor derived from a small cell lung cancer (SCLC) comprising administering to the subject a therapeutically effective amount of an antibody or antigen-binding portion thereof that specifically binds to a Programmed Death-1 (PD-1) receptor and inhibits PD-1 activity ("an anti-PD-1 antibody"), wherein the tumor has a high tumor mutational burden (TMB) status; wherein the high TMB status is characterized by at least 210 genomic alterations as measured by a genomic profiling assay comprising that detects alterations in ABL1 BRAF, CHEK1, FANCC, GATA3, JAK2, MITF, PDCDILG2, RBM10, STAT4, ABL2, BRCA1, CHEK2, FANCD2, GATA4, JAK3, MLH1, PDGFRA, RET, STK11, ACVR1B, BRCA2, C1C, FANCE, GATA6, JUN, MPL, PDGFRB, RICTOR, SUFU, AKT1, BRD4, CREBBP, FANCF, GID4 (C17orf39), KAT6A (MYST3), MRE11A, PDK1, RNF43, SYK, AKT2, BRIP1, CRKL, FANCG, GUI, KDM5A, MSH2, PIK3C2B, ROS1, TAF1, AKT3, BTG1, CRLF2, FANCL, GNA11, KDM5C, MSH6, PIK3CA, RPTOR, TBX3, ALK, BTK, CSF1R, FAS, GNA13, KDM6A, MTOR, PIK3CB, RUNX1, TERC, AMER1 (FAM123B), C11or/30 (EMSY), CTCF, FAT1, GNAQ, KDR, MUTYH, PIK3CG, RUNX1T1, TERT (promoter only), AFC, CARD11, CTNNA1, FBXW7, GNAS, KEAP1, MYC, PIK3R1, SDHA, TET2, AR, CBFB, CTNNB1, FGF10, GPR124, KEL, MYCL (MYCL1), PIK3R2, SDHB, TGFBR2, ARAF, CBL, CUL3, FGF14, GRIN2A, KIT, MYCN, PLCG2, SDHC, TNFAIP3, ARFRP1, CCND1, CYLD, FGF19, GM113, KLHL6, MYD88, PMS2, SDHD, TNFRSF14, ARIDIA, CCND2, DAXX, FGF23, GSK3B, KMT2A (MLL), NF1, POLD1, SETD2, TOP1, ARIDIB, CCND3, DDR2, FGF3, H3F3A, KMT2C (MLL3), NF2, POLE, SF3B1, TOP2A, ARID2, CCNE1, DICER1, FGF4, HGF, KMT2D (MLL2), NFE2L2, PPP2RIA, SLIT2, TP53, ASXL1, CD274, DNMT3A, FGF6, HNF1A, KRAS, NFKBIA, PRDM1, SMAD2, TSC1, ATM, CD79A, DOTIL, FGFR1, HRAS, LMO1, NKX2-1, PREX2, SMAD3, TSC2, ATR, CD79B, EGFR, FGFR2, HSD3B1, LRPIB, NOTCH 1, PRKARIA, SMAD4, TSHR, ATRX, CDC73, EP300, FGFR3, HSP90AA1, LYN, NOTCH2, PRKCI, SMARCA4, U2AF1, AURKA, CDH1, EPHA3, FGFR4, IDH1, LZTR1, NOTCH3, PRKDC, SMARCB1, VEGFA, AURKB, CDK12, EPHA5, FH, IDH2, MAGI2, NPM1, PRSS8, SMO, VHL, AXLN1, CDK4, EPHA 7, FLCN, IGF1R, MAP2K1, NRAS, PTCH1, SNCAIP, WISP3, AXL, CDK6, EPHB1, FLT1, IGF2, MAP2K2, NSD1, PTEN, SOCS1, WT1, BAP1, CDK8, ERBB2, FLT3, IKBKE, MAP2K4, NTRK1, PTPN11, SOX10, XPO1, BARD1, CDKN1A, ERBB3, FLT4, IKZF1, MAP3K1, NTRK2, QKI, SOX2, ZBTB2, BCL2, CDK1N1B, ERBB4, FOXL2, IL7R, MCL1, NTRK3, RAC1, SOX9, ZNF217, BCL2L1, CDKN2A, ERG, FOXP1, INHBA, MDM2, NUP93, RAD50, SPEN, ZNF703, BCL2L2, CDKN2B, ERRF11, FRS2, INPP4B, MDM4, PAK3, RADS1, SPOP, BCL6, CDKN2C, ESR1, FUBP1, IRF2, MED12, PALB2, RAF1, SPTA1, BCOR, CEBPA, EZH2, GABRA6, IRF4, MEF2B, PARK2, RANBP2, SRC, BCORL1, CHD2, FAM46C, GATA1, IRS2, MEN1, FAX5, RARA, STAG2, BLM, CHD4, FANCA, GATA2, JAK1, MET, PBRM1, RB1, and STAT3.

2. A method for treating a subject afflicted with a tumor derived from an SCLC comprising administering to the subject a therapeutically effective amount an antibody or antigen-binding portion thereof that specifically binds to a Programmed Death-1 (PD-1) receptor and inhibits PD-1 activity ("an anti-PD-1 antibody") and an antibody or antigen-binding portion thereof that specifically binds to CTLA-4 ("an anti-CTLA-4 antibody"), wherein the tumor has a high TMB status; and wherein the high TMB status is characterized by at least 210 genomic alterations as measured by a genomic profiling assay comprising that detects alterations in ABL1 BRAF, CHEK1, FANCC, GATA3, JAK2, MITF, PDCDILG2, RBM10, STAT4, ABL2, BRCA1, CHEK2, FANCD2, GATA4, JAK3, MLH1, PDGFRA, RET, STK11, ACVR1B, BRCA2, C1C, FANCE, GATA6, JUN, MPL, PDGFRB, RICTOR, SUFU, AKT1, BRD4, CREBBP, FANCF, GID4 (C17or f39), KAT6A (MYST3), MRE11A, PDK1, RNF43, SYK, AKT2, BRIP1, CRKL, FANCG, GUI, KDM5A, MSH2, PIK3C2B, ROS1, TAF1, AKT3, BTG1, CRLF2, FANCL, GNA11, KDM5C, MSH6, PIK3CA, RPTOR, TBX3, ALK, BTK, CSF1R, FAS, GNA13, KDM6A, MTOR, PIK3CB, RUNX1, TERC, AMER1 (FAM123B), Cll or/30 (EMSY), CTCF, FAT1, GNAQ, KDR, MUTYH, PIK3CG, RUNX1T1, TERT (promoter only), AFC, CARD11, CTNNA1, FBXW7, GNAS, KEAP1, MYC, PIK3R1, SDHA, TET2, AR, CBFB, CTNNB1, FGF10, GPR124, KEL, MYCL (MYCL1), PIK3R2, SDHB, TGFBR2, ARAF, CBL, CUL3, FGF14, GRIN2A, KIT, MYCN, PLCG2, SDHC, TNFAIP3, ARFRP1, CCND1, CYLD, FGF19, GRM3, KLHL6, MYD88, PMS2, SDHD, TNFRSF14, ARID1A, CCND2, DAXX, FGF23, GSK3B, KMT2A (MLL), NF1, POLD1, SETD2, TOP1, ARID1B, CCND3, DDR2, FGF3, H3F3A, KMT2C (MLL3), NF2, POLE, SF3B1, TOP2A, ARID2, CCNE1, DICER1, FGF4, HGF, KMT2D (MLL2), NFE2L2, PPP2R1A, SLIT2, TP53, ASXL1, CD274, DNMT3A, FGF6, HNF1A, KRAS, NFKBIA, PRDM1, SMAD2, TSC1, ATM, CD79A, DOT1L, FGFR1, HRAS, LMO1, NKX2-1, PREX2, SMAD3, TSC2, ATR, CD79B, EGFR, FGFR2, HSD3B1, LRPIB, NOTCH 1, PRKARIA, SMAD4, TSHR, ATRX, CDC73, EP300, FGFR3, HSP90AA1, LYN, NOTCH2, PRKCI, SMARCA4, U2AF1, AURKA, CDHJ, EPHA3, FGFR4, IDH1, LZTR1, NOTCH3, PRKDC, SMARCB1, VEGFA, AURKB, CDK12, EPHA5, FH, IDH2, MAGI2, NPM1, PRSS8, SMO, VHL, AXLN1, CDK4, EPHA 7, FLCN, IGF1R, MAP2K1, NRAS, PTCH1, SNCAIP, WISP3, AXL, CDK6, EPHB1, FLT1, IGF2, MAP2K2, NSDJ, PTEN, SOCS1, WT1, BAP1, CDK8, ERBB2, FLT3, IKBKE, MAP2K4, NTRK1, PTPN11, SOX10, XPO1, BARD1, CDK1VIA, ERBB3, FLT4, IKZF1, MAP3K1, NTRK2, QKI, SOX2, ZBTB2, BCL2, CDKN1B, ERBB4, FOXL2, IL7R, MCL1, NTRK3, RAC1, SOX9, ZNF217, BCL2L1, CDKN2A, ERG, FOXP1, INHBA, MDM2, NUP93, RAD50, SPEN, ZNF703, BCL2L2, CDKN2B, ERRF11, FRS2, INPP4B, MDM4, PAK3, RAD51, SPOP, BCL6, CDKN2C, ESR1, FUBP1, IRF2, MED12, PALB2, RAF1, SPTA1, BCOR, CEBPA, EZH2, GABRA6, IRF4, MEF2B, PARK2, RANBP2, SRC, BCORL1, CHD2, FAM46C, GATA1, IRS2, MEN1, FAX5, RARA, STAG2, BLM, CHD4, FANCA, GATA2, JAK1, MET, PBRM1, RB1, and STAT3.

3. The method of claim 1, wherein the TMB status is determined by sequencing nucleic acids in a biological sample obtained from the subject and identifying a genomic alteration in the sequenced nucleic acids.

4. The method of claim 1, wherein the genomic alteration comprises:
one or more somatic mutations;
(ii) one or more nonsynonymous mutations;
(iii) one or more missense mutations;
(iv) one or more alterations selected from the group consisting of a base pair substitution, a base pair insertion, a base pair deletion, a copy number alteration (CNAs), a gene rearrangement, and any combination thereof; or
(v) any combination of (i)-(iv).

5. The method of claim 3, wherein the biological sample comprises a tumor tissue biopsy, a liquid biopsy, blood, serum, plasma, exoRNA, circulating tumor cells, ctDNA, cfDNA, or any combination thereof.

6. The method of claim 1, wherein:
the SCLC comprises a small cell carcinoma, (ii) the SCLC comprises a combined small cell carcinoma, (iii) the SCLC is recurrent or refractory following at least one previous line of therapy to treat the tumor, or (iv) any combination of (i)-(iii).

7. The method of claim 1, wherein the anti-PD-1 antibody is administered at a weight based dose ranging from 0.1 mg/kg to 10.0 mg/kg body weight or at a flat dose of about 200 mg, about 220 mg, about 240 mg, about 260 mg, about 280 mg, about 300 mg, about 320 mg, about 340 mg, about 360 mg, about 380 mg, about 400 mg, at least about 420 mg, about 440 mg, about 460 mg, about 480 mg, about 500 mg, or about 550 mg once every 2, 3, or 4 weeks.

8. The method of claim 1, wherein the anti-PD-1 antibody is administered:
at a weight based dose of 3 mg/kg body weight once every 2 weeks;
(ii) at a weight based dose of 5 mg/kg body weight once every 3 weeks;
(iii) at a weight based dose of 10 mg/kg body weight once every 3 weeks;
(iv) at a flat dose of about 240 mg once every 2 weeks;
(v) at a flat dose of about 360 mg once every 3 weeks; or
(vi) at a flat dose of about 480 mg once every 4 weeks.

9. The method of claim 2, wherein
(a) the anti-CTLA-4 antibody is administered at a dose ranging from at least about 0.1 mg/kg to at least about 10.0 mg/kg body weight once about every 1, 2, 3, or 4 weeks
(b) the anti-PD-1 antibody is administered:
(i) at a weight based dose of 3 mg/kg body weight once every 2 weeks;
(ii) at a weight based dose of 5 mg/kg body weight once every 3 weeks;
(iii) at a weight based dose of 10 mg/kg body weight once every 3 weeks;
(iv) at a flat dose of about 240 mg once every 2 weeks;
(v) at a flat dose of about 360 mg once every 3 weeks; or
(vi) at a flat dose of about 480 mg once every 4 weeks; or
(c) any combination of (a) and (b).

10. The method of claim 2, wherein the TMB status is determined by sequencing nucleic acids in a biological sample of the subject and identifying the genomic alteration in the sequenced nucleic acids.

11. The method of claim 10, wherein the genomic alteration comprises:
   one or more somatic mutations;
   (ii) one or more nonsynonymous mutations;
   (iii) one or more missense mutations;
   (iv) one or more alterations selected from the group consisting of a base pair substitution, a base pair insertion, a base pair deletion, a copy number alteration (CNAs), a gene rearrangement, and any combination thereof; or
   (v) any combination of (i)-(iv).

12. The method of claim 10, wherein the biological sample comprises a tumor tissue biopsy, a liquid biopsy, blood, serum, plasma, exoRNA, circulating tumor cells, ctDNA, cfDNA, or any combination thereof.

13. The method of claim 2, wherein:
   (i) the SCLC comprises a small cell carcinoma,
   (ii) the SCLC comprises a combined small cell carcinoma,
   (iii) the SCLC is recurrent or refractory following at least one previous line of therapy to treat the tumor, or
   (iv) any combination of (i)-(iii).

* * * * *